(12) United States Patent
Monpoeho et al.

(10) Patent No.: US 11,549,154 B2
(45) Date of Patent: Jan. 10, 2023

(54) COMPOSITIONS AND METHODS FOR DETECTING A BIOLOGICAL CONTAMINANT

(71) Applicant: Regeneron Pharmaceuticals, Inc., Tarrytown, NY (US)

(72) Inventors: Serge Monpoeho, East Greenbush, NY (US); Sheldon Mink, Rensselaer, NY (US); Paul Vescio, Malta, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 275 days.

(21) Appl. No.: 16/855,217

(22) Filed: Apr. 22, 2020

(65) Prior Publication Data
US 2020/0248278 A1    Aug. 6, 2020

Related U.S. Application Data

(62) Division of application No. 15/080,859, filed on Mar. 25, 2016, now Pat. No. 10,669,594.

(60) Provisional application No. 62/139,321, filed on Mar. 27, 2015.

(51) Int. Cl.
*C12Q 1/70* (2006.01)
*C12Q 1/68* (2018.01)
*C12Q 1/6876* (2018.01)

(52) U.S. Cl.
CPC ........... *C12Q 1/701* (2013.01); *C12Q 1/6876* (2013.01); *C12Q 2600/158* (2013.01); *C12Q 2600/166* (2013.01)

(58) Field of Classification Search
CPC .............. C12Q 1/701; C12Q 1/6876; C12Q 2600/158; C12Q 2600/166
See application file for complete search history.

(56) References Cited

U.S. PATENT DOCUMENTS

| | | | |
|---|---|---|---|
| 5,585,254 A * | 12/1996 | Maxwell | C07K 14/005 435/235.1 |
| 9,834,815 B2 | 12/2017 | Brewer et al. | |
| 10,669,594 B2 | 6/2020 | Monpoeho et al. | |
| 2002/0177222 A1 * | 11/2002 | Li | C12N 7/00 435/235.1 |
| 2003/0170612 A1 * | 9/2003 | Pichuantes | C12Q 1/701 435/5 |
| 2006/0166232 A1 | 7/2006 | Vickery et al. | |
| 2015/0093749 A1 | 4/2015 | Ling | |

FOREIGN PATENT DOCUMENTS

| | | | |
|---|---|---|---|
| CN | 102206713 A | 10/2011 | |
| DE | 102006034844 B3 | 12/2007 | |
| EP | 1 077 260 A1 | 2/2001 | |
| EP | 2 098 599 A1 | 9/2009 | |
| GB | 2525024 A | 10/2015 | |
| JP | 2014513921 A | 6/2014 | |
| WO | WO 01/46463 A2 | 6/2001 | |
| WO | WO 2004/044247 A2 | 5/2004 | |
| WO | WO 03/002753 A2 | 1/2009 | |
| WO | WO 2012/052158 A2 | 4/2012 | |
| WO | WO 2014/006432 A2 | 1/2014 | |
| WO | WO-2014055515 A1 * | 4/2014 | ........... A61K 38/162 |

OTHER PUBLICATIONS

Jones, M.D., Brand, N.J. and Fersht, A.R., 1986. Single-stranded M13 DNA: use as a cloning vector. Nucleic acids research, 14(24), p. 10116. (Year: 1986).*
Ninove et al., 2011. RNA and DNA bacteriophages as molecular diagnosis controls in clinical virology: a comprehensive study of more than 45,000 routine PCR tests. PloS one, 6(2), p. e16142. (Year: 2011).*
Sambrook, J. and Russell, D.W., 2006. Cloning into Bacteriophage M13 Vectors. Cold Spring Harbor Protocols, 2006(1), pdb-prot4018, pp. 1-3. (Year: 2006).*
Shien et al., 2008. Identification of sequence changes in live attenuated goose parvovirus vaccine strains developed in Asia and Europe. Avian Pathology, 37(5), pp. 499-505. (Year: 2008).*
Yu, Q., 1996. Cloning into M13 bacteriophage vectors. In Basic DNA and RNA Protocols (pp. 343-348). Humana Press. (Year: 1996).*
Vieira, J. and Messing, J., 1982. The pUC plasmids, an M13mp7-derived system for insertion mutagenesis and sequencing with synthetic universal primers. Gene, 19(3), pp. 259-268. (Year: 1982).*
Atkinson, B et al., "Development of a real-time RT-PCR assay for the detection of Crimean-Congo hemorrhagic fever virus," Vector Borne Zoonotic Dis., Sep. 2012; 12(9):786-93.
Berting et al., "Virus Susceptibility of Chinese Hamster Ovary (CHO) Cells and Detection of Viral Contaminations by Adventitious Agent Testing," Biotechnology and Bioengineering, (2010) 106(4): 598-607.
Besselsen, D.G., "Identification of Novel Murine Parvovirus Strains by Epidemiological Analysis of Naturally Infected Mice," Journal of General Virology, vol. 87, No. 6, Jun. 1, 2006, pp. 1543-1556.
Cotmore, et al., "Replication Initiator Protein NS1 of the parvovirus Minute Virus of Mice Binds to Modular Divergent Sites Distributed throughout Duplex Viral DNA," J. Virol., Dec. 2007; 81(23):13015-13027.
Cotmore et al., "The Autonomously Replicating Parvoviruses of Vertebrates," Advances in Virus Research, 33: 91-174 (1987).

(Continued)

*Primary Examiner* — Teresa E Strzelecka
*Assistant Examiner* — Olayinka A Oyeyemi
(74) *Attorney, Agent, or Firm* — Cooley LLP; Matthew Pavao; Ivor R. Elrifi

(57) ABSTRACT

Provided are compositions and methods useful to the determination of whether a microbial contaminant is present in a biological therapeutic production process. Specifically, an artificial positive amplification control plasmid and unique quantitative PCR detection probe are provided, which enables the rapid and real-time detection of a false positive result.

14 Claims, No Drawings

Specification includes a Sequence Listing.

(56) References Cited

OTHER PUBLICATIONS

Database Embl [Online] "Sequence 3 from Patent EP1077260" Retrieved from EBI Accession No. EM_PAT: AX137738, Database Accession No. AX137738 The Whole Document & EP 1 077 260 A1 (Deutsches Krebsforsch [DE]; Feb. 21, 2001.
Decaro et al., "A real-time PCR assay for rapid detection and quantitation of canine parvovirus type 2 in the feces of dogs," Veterinary Microbiology (2005) 105:19-28.
Diez-Valcarce et al., "Construction and Analytical Application of Internal Amplification Controls (IAC) for Detection of Food Supply Chain-Relevant Viruses by Real-Time PCR-Based Assays," Food Anal. Methods (2011) 4:437-445.
Drosten, C. et al., "Evaluation of a New PCR Assay with Competitive Internal Control Sequence for Blood Donor Screening," Transfusion, American Association of Blood Banks, Bethesda, MD, US, vol. 40. No. 6, Jun. 1, 2000, pp. 718-724.
European Office Action for European Application No. 16734060.3, dated Nov. 11, 2018.
Gerriets, JE et al., "Implementation of a T4 extraction control for molecular assays of cerebrospinal fluid and stool specimens," J Mol Diagn., Jan. 2008; 10(1):28-32.
Gonçalves-de-Albuquerque et al., "Tracking false-negative results in molecular diagnosis: proposal of a triplex-PCR based method for leishmaniasis diagnosis," Journal of Venomous Animals and Toxins including Tropical Diseases, 2014, 20:16, 6 pages.
International Search Report and Written Opinion for PCT/US2016/024216, dated Aug. 12, 2016.
Jacoby et al., "Rodent Parvovirus Infections," Laboratory Animinal Science, (1996) 46(4): 370-80.
Kerr and Nims, "Adventitious Viruses Detected in Biopharmaceutical Bulk Harvest Samples over a 10 Year Period," PDA Journal of Pharmaceutical Science & Technology, (2010) 64(5): 481-485.
Kothapalli et al., "Problems associated with product enhancement reverse transcriptase assay using bacteriophage MS2 RNA as a template," J. Virol. Methods, (2003) 109(2): 203-207.
Ninove, Laetitia et al., "RNA and DNA Bacteriophages as Molecular Diagnosis Controls in Clinical Virology: A Comprehensive Study of More Than 45,000 Routine PCR Tests", PLoS One, Feb. 9, 2011, vol. 6, No. 2, e16142, 7 pages.
Lee et al., "Comparative evaluation of the QIAGEN QIAsymphony® SP system and bioMérieux NucliSens easyMAG Automated extraction platforms in a clinical virology laboratory," J. Clin. Virol., (2011) 52(4): 339-43.
Liu et al., "Recovery and Purification Process Development for Monoclonal Antibody production," mAbs, (2010) 2(5): 480-499.
MacKay et al., "Survey and Summary: Real-Time PCR in Virology," Nucleic Acids Research, (2002) 30(6): 1292-1305.
Marras et al., "Efficiencies of Fluorescence Resonance Energy Transfer and Contact-Mediated Quenching in Oligonucleotide Probes," Nucleic Acids Research, (2002) 30(21): e122, 8 pages.
Marras, S., "Interactive Fluorophore and Quencher Pairs for Labeling Fluorescent Nucleic Acid Hybridization Probes," Mol Biotechnol, (2008) 38:247-255.
Marras, S., "Selection of Fluorophore and Quencher Pairs for Fluorescent Nucleic Acid Hybridization Probes," Methods Mol. Biol. 2006; 335:3-16.
Merten, O.W., "Virus Contaminations of Cell Cultures—A Biotechnological View," Cytotechnology, 2002, 39(2):91-116.
Miesegaes et al., "Analysis of Viral Clearance Unit Operations for Monoclonal Antibodies," Biotechnology and Bioengineering, (2010) 106(2): 238-246.
Moody et al., "Mouse Minute Virus (MMV) Contamination—A Case Study: Detection, Root Cause Determination, and Corrective Actions," PDA Journal of Pharmaceutical Science and Technology, (2011) 65(6): 580-288.
Muller, J., et al., "Development and Validation of a Real-Time PCR Assay for Routine Testing of Blood Donations for Parvovirus B19 DNA," Infusion Therapy and Transfusion Medicine—Infusionstherapieund Transfusionmedizin, 2002, vol. 29, No. 5, pp. 254-258.
Redig and Besselsen, "Detection of Rodent Parvoviruses by Use of Fluorogenic Nuclease Polymerase Chain Reaction Assays," Comparative Medicine, Aug. 2001, vol. 51, No. 4, pp. 326-331.
Sachsenröder et al., "Simultaneous Identification of DNA and RNA Viruses Present in Pig Faeces Using Process-Controlled Deep Seguencing," PLoS ONE, Apr. 2012, 7(4): e34631, 11 pages.
Skiadopoulos et al., "Characterization of Linker Insertion and Point Mutations in the NS-1 Gene of Minute Virus of Mice: Effects on DNA Replication and Transcriptional Activation Functions of NS-1," Virology (1992) 188:122-134.
Van Wezenbeek et al., "Nucleotide Seguence of the Filamentous Bacteriophage M13 DNA Genome: Comparison with phage fd," Gene, (1980) 11:129-148.
Zhan et al., "Detection of Minute Virus of Mice Using Real Time Quantitative PCR in Assessment of Virus Clearance during the Purification of Mammalian Cell Substrate Derived Biotherapeutics," Biologicals, (2002) 30: 259-270.
Zhong et al., "A preliminary analysis of antineoplastic activity of parvovirus MVMp NS-1 proteins," Cell Research (1997) 7:217-227.
Moniwa, M. et al., "Performance of a foot-and-mouth disease virus reverse transcription-polymerase chain reaction with amplification controls between three realtime instruments," J Vet Diagn Invest (2007) 19:9-20.

* cited by examiner

COMPOSITIONS AND METHODS FOR DETECTING A BIOLOGICAL CONTAMINANT

CROSS-REFERENCE TO RELATED APPLICATIONS

This application is a Divisional of U.S. patent application Ser. No. 15/080,859, filed Mar. 25, 2016 which claims the benefit of priority under 35 USC § 119(e) of U.S. Provisional Patent Application No. 62/139,321, filed 27 Mar. 2015. The contents of each of these applications is herein incorporated by reference in their entirety.

INCORPORATION BY REFERENCE OF SEQUENCE LISTING

The contents of the text file submitted electronically herewith are incorporated herein by reference in their entirety: a computer readable format copy of the Sequence Listing (filename: REGE-008D01US_SeqList, date recorded: Apr. 21, 2020, file size: 83 KB).

FIELD OF THE INVENTION

The present invention relates generally to the process of manufacturing biological molecules via cell culture. The present invention relates more specifically, but not exclusively, to compositions and methods for detecting biological contaminants in cell culture.

BACKGROUND OF THE INVENTION

Biopharmaceutical drugs, especially therapeutic antibodies, are produced by mammalian cell culture. Chinese hamster ovary (CHO) cells are the most commonly used host cell. These production systems are prone to adventitious and endogenous virus infection, which presents a potential safety problem for the biopharmaceutical drug. Viral clearance procedures and viral load measurements are therefore used to promote the safety of the drug. Steps employed to reduce viral load include nanofiltration, virus inactivation by heat or pH hold, and chromatography. Viral load and the effectiveness of virus removal can be monitored by time consuming infectivity assays or by fast quantitative assays such as real-time PCR or quantitative polymerase chain reaction (Q-PCR).

Q-PCR requires the proper negative and positive controls to be reliable. Nucleic acid extraction controls are added to test samples to control for proper nucleic acid extraction. If the nucleic acid extraction control is negative or outside of the expected recovery range during Q-PCR, then the sample is rejected. Conversely, if the nucleic acid extraction control is positive or within the expected recovery range during Q-PCR, nucleic acid extraction from the test sample is deemed reliable. A negative control is usually included in the Q-PCR assay, such as a sample-free buffer. The presence of a positive signal in the negative control might signify the contamination of the Q-PCR or nucleic acid extraction reagents with virus material.

A positive amplification control may also be included in a Q-PCR viral load assay. Such a positive control may include conserved viral nucleic acid sequences that are amplified using primers that amplify genuine viral contaminants. The failure of the Q-PCR to detect the positive control may indicate that the amplification procedure would have failed to detect a viral contaminant if one were present in the test sample.

The use of positive amplification controls, which emulate the target contaminant, creates its own problems. If the test sample is contaminated with even a slight amount of positive control, given the exquisite sensitivity of Q-PCR, the test sample may show a false positive. False positives can be mitigated to some extent by using a low level of positive amplification control, using segregated rooms for positive control work, using the UNG/dUTP system to selectively degrade PCR products containing dUTP, using single-use containers and displacement pipettes, and by thoroughly cleaning work areas and equipment. Regardless of the fastidious use of those mitigators, false positive results still occur during PCR testing.

In biopharmaceutical manufacturing, the risk of getting a false positive for a biological contaminant is non-negligible and may result in costly corrective actions. There is a great need for systems and methods to determine whether a given positive PCR result is a true positive or a false positive resulting from cross-contamination of the positive control. Applicants have developed and now disclose positive control compositions, systems and methods that permit the real-time determination of false positive Q-PCR signals.

SUMMARY OF THE INVENTION

Applicant has solved the problem of identifying in real-time whether a positive Q-PCR signal for a target contaminant in a test sample is a true positive or a false positive due to cross-contamination. Applicant has created a positive amplification control (PAC) plasmid that includes a biological contaminant target sequence (i.e., the positive control sequence) and a unique artificial plasmid-specific sequence. This unique artificial plasmid-specific sequence enables the assay technician to specifically identify the plasmid when it is in a sample. Thus, when a positive contaminant signal is detected and the artificial plasmid-specific sequence is determined not to be present, the technician can be confident that the result is a true positive result. Conversely, in the event of a false positive, the presence of the unique artificial plasmid-sequence allows the technician to quickly rule out the ostensible positive result as a false positive.

In some embodiments, the positive control unique artificial plasmid-specific sequence ("unique sequence"; a.k.a. PACP or positive amplification control polynucleotide) is detected using a fluorescently labeled artificial oligonucleotide detection probe ("unique detection probe" or "UDP") included in the Q-PCR reaction mix. The unique detection probe comprises a nucleic acid polymer covalently bound to a fluorophore and a quencher. The "unique" nucleic acid polymer is designed to specifically anneal to the unique sequence and incorporate into amplicon copies of the unique sequence during PCR. The "unique" nucleic acid polymer is designed to not recognize or anneal to any naturally occurring parvovirus under hybridization conditions employed in the operation of the subject assay. In one embodiment, the "unique" nucleic acid polymer comprises from 17 to 20 nucleotides, wherein no more than seven (7) to 10 internal consecutive nucleotides and no more than six (6) consecutive three-prime nucleotides are identical to any parvovirus sequence. In one embodiment, the "unique" nucleotide polymer comprises from 17 to 20 nucleotides, wherein no more than 7 to 10 consecutive nucleotides and no more than six (6) consecutive three-prime nucleotides are identical to any parvovirus sequence set forth in SEQ ID NOs: 9 and 12-37. When the nucleic acid polymer of the unique detection probe is not incorporated into amplicon copies, the quencher remains in close proximity to the fluorophore. If the fluorophore is excited, then the quencher absorbs the emitted light and prevents that light from being detected (by FRET or contact quenching). When the nucleic acid polymer is incorporated into the amplicon copies (i.e., when the unique sequence is present in the sample), the fluorophore and the quencher are released from the unique detection probe and are therefore spatially separated. In that case, when the fluorophore is excited, the quencher is sufficiently far away that it cannot efficiently quench the emitted light. The emitted light can therefore be detected. Thus, when the unique sequence is present in the sample, the detectable emission wavelength increases in intensity as the PCR proceeds. When the unique sequence is absent, the quencher does its work and no emission wavelength is detected as the PCR advances. In one embodiment, the fluorophore is attached at or near the 5-prime end of the nucleic acid polymer, and the quencher at or near the 3-prime end. In an alternative embodiment, the fluorophore is attached at or near the 3-prime end of the nucleic acid polymer, and the quencher at or near the 5-prime end.

Any fluorophore-quencher pair now known or later discovered may be used in the practice of this invention. (See for example S. A. Marras, "Selection of fluorophore and quencher pairs for fluorescent nucleic acid hybridization probes," Methods Mol. Biol. 2006; 335:3-16.) In some embodiments, the fluorophore has an excitation wavelength of 495 nm, 538 nm, or 646 nm and an emission wavelength of 520 nm, 554 nm, or 669 nm, respectively. In some embodiments, the quencher is a dye with an absorbance peak of 430 nm to 672 nm. In some embodiments, the quencher is selected from the group consisting of DDQ-I, Dabcyl, Eclipse, Iowa Black FQ, BHQ-1, QSY-7, BHQ-2, DDQ-II, Iowa Black RQ, QSY-21, and DHQ-3. In one embodiment, the fluorophore has an excitation wavelength of 495 nm and an emission wavelength of 520 nm, for example FAM, and the quencher is BHQ-1. In one embodiment, the nucleic acid polymer comprises the nucleic acid sequence of SEQ ID NO:3 (5'-TGTCGATGGCGAATGGCTA-3').

One aspect of the invention is the unique detection probe itself, as described above, containing the nucleic acid polymer and the linked fluorophore and quencher. Other aspects of the invention include the positive amplification control (PAC) plasmid itself, which contains a biological contaminant target sequence and the unique artificial plasmid-specific sequence, and the use of that plasmid as a positive control to assess the presence of a target biological contaminant in a cell culture. The PAC plasmid is used to control for the successful PCR amplification reaction designed to amplify target biological contaminant sequences. For example, a separate and parallel PCR reaction, which contains the identical components and is run under identical parameters as the test sample, but containing the positive control plasmid in lieu of a test sample, is run. If the positive control plasmid-containing sample yields a positive "contaminant" signal, but the test sample does not, then one might conclude that the test sample is devoid of the target biological contaminant. In some embodiments, the test sample is obtained from a mammalian cell culture, such as a bioreactor culture containing CHO cells engineered to produce a therapeutic protein of interest.

In one embodiment, the PAC plasmid contains (a) a target amplification polynucleotide (TAP) sequence, such as for example a parvovirus nucleic acid sequence or sequence of another target contaminant, and (b) a plasmid amplification control polynucleotide (PACP) sequence. The PACP sequence (sense or Crick strand) is complementary to the nucleic acid polymer of the unique sequence probe (antisense or Watson strand).

In one embodiment, the PAC plasmid is deployed in a separate Q-PCR reaction in parallel with a Q-PCR reaction containing a test sample. The TAP sequence is designed to be representative of the target biological contaminant. For example, if the test sample Q-PCR reaction fails to produce TAP amplicons, and the positive control (i.e., PAC plasmid-containing sample) Q-PCR fails to produce TAP amplicons, then one may assume that the Q-PCR reaction failed. In one embodiment, the target biological contaminant is a rodent parvovirus and the TAP sequence comprises a rodent parvovirus sequence. In one embodiment, the TAP sequence comprises all or part of the parvovirus NS1 sequence, which is conserved across several rodent parvovirus strains. See Cotmore, et al., "Replication Initiator Protein NS1 of the parvovirus Minute Virus of Mice Binds to Modular Divergent Sites Distributed throughout Duplex Viral DNA," J. Virol. 2007 December; 81(23):13015-13027. In some embodiments, the several rodent parvovirus strains include minute virus of mice prototype strain (MVMp), minute virus of mice immunosuppressive strain (MVMi), minute virus of mice Cutter strain (MVMc), mouse parvovirus 1b (MPV-1b), mouse parvovirus 1a (MPV-1a), mouse parvovirus 1c (MVP-1c), hamster parvovirus (HaPV), Toolan's parvovirus (H-1), Kilham rat virus (KRV), Rat parvovirus 1a (RPV-1a), rat minute virus (RMV), and University of Massachusetts strain of rat virus L (RV-Umass). See O.-W. Merten, "Virus Contaminations of Cell Cultures—A Biotechnological View," Cytotechnology. 2002 July; 39(2):91-116. In one embodiment, the TAP sequence comprises the nucleic acid sequence of SEQ ID NO:1, SEQ ID NO:2, and the complement of SEQ ID NO:4.

In other aspects, the invention is directed to a PCR cocktail composition and method of using the PCR cocktail to detecting a target contaminant in a test sample and ruling out a false positive due to contamination of the test sample with the PAC.

In one embodiment, the PCR cocktail contains inter alia a target contaminant specific forward oligonucleotide primer, target contaminant specific oligonucleotide detection probe, an artificial oligonucleotide detection probe, such as the unique detection probe (UDP) described above, and a target contaminant specific reverse oligonucleotide primer. In an embodiment in which the target contaminant is a rodent parvovirus, the PCR cocktail contains inter alia a rodent parvovirus specific forward oligonucleotide primer, a rodent parvovirus specific oligonucleotide detection probe, an artificial oligonucleotide detection probe, such as the unique detection probe (UDP) described above, and a rodent parvovirus specific reverse oligonucleotide primer. Each detection probe (i.e., target contaminant specific oligonucleotide detection probe, such as rodent parvovirus specific oligonucleotide detection probe, and artificial oligonucleotide detection probe) contains a nucleic acid sequence linked to a fluorophore at one end (either 5-prime or 3-prime) and a quencher at the other end (either 3-prime or 5-prime, respectively).

Here, the rodent parvovirus specific forward oligonucleotide primer and the nucleic acid sequence of the rodent parvovirus specific oligonucleotide detection probe hybridize to the antisense strand of the parvovirus. The rodent parvovirus specific reverse oligonucleotide primer hybridizes to the sense strand of the parvovirus. In one embodiment, the parvovirus sequence to which the primers and parvovirus specific oligonucleotide probe hybridize is a conserved rodent parvovirus sequence. In one case, the conserved parvovirus sequence is a parvovirus NS1 sequence, such as for example the nucleic acid sequence described in SEQ ID NO:9. By using a conserved sequence, a single probe will be effective to detect multiple strains of rodent parvovirus.

In one embodiment, the artificial oligonucleotide detection probe does not hybridize to a parvovirus nucleic acid or any biological contaminant sequence. The nucleic acid of the artificial oligonucleotide detection probe is synthetic and will not hybridize with any stringency to any biological contaminants nucleic acid sequence. In one embodiment, the nucleic acid of the artificial oligonucleotide detection probe (a.k.a. "unique" nucleic acid polymer or unique sequence) is designed to not recognize or anneal to any naturally occurring parvovirus under hybridization conditions employed in the operation of the subject assay. In one embodiment, the "unique" nucleic acid polymer comprises from 17 to 20 nucleotides, wherein no more than seven (7) to 10 internal consecutive nucleotides and no more than six (6) consecutive three-prime nucleotides are identical to any parvovirus sequence. In one embodiment, the "unique" nucleotide polymer comprises from 17 to 20 nucleotides, wherein no more than 7 to 10 consecutive nucleotides and no more than six (6) consecutive three-prime nucleotides are identical to any parvovirus sequence set forth in SEQ ID NOs: 9 and 12-37. However, the nucleic acid of the artificial oligonucleotide detection probe (i.e., the unique sequence) hybridizes to the PACP sequence of the PAC plasmid. Thus, the artificial oligonucleotide detection probe detects the PAC plasmid, but not a parvovirus or other biological contaminant sequence.

In one embodiment, the PCR cocktail can be used to determine whether the PAC plasmid is present in the test biological sample, rendering a false positive result. Here, if the test sample shows a positive Q-PCR signal for the parvovirus specific oligonucleotide probe, and a negative Q-PCR signal for the artificial oligonucleotide detection probe, then the test sample is presumed to be free of PAC contamination (i.e., true positive).

In one embodiment, the target contaminant specific forward oligonucleotide primer comprises the sequence of SEQ ID NO:1; the target contaminant specific oligonucleotide detection probe nucleic acid comprises the sequence of SEQ ID NO:2; the artificial oligonucleotide detection probe nucleic acid (i.e., the UDP) comprises the sequence of SEQ ID NO:3; and the target contaminant specific reverse oligonucleotide primer comprises the sequence of SEQ ID NO:4.

In other aspects, the invention provides a system and method for detecting a biological contaminant in a test sample. Here, the test sample is a cell culture, such as for example an industrial scale mammalian cell culture for the production of a therapeutic protein. Mammalian cells useful in the practice of this invention include, but are not limited to CHO cells, CHO-K1 cells, and EESYR cells (see U.S. Pat. No. 7,771,997). The system and method include—in addition to the primers, probes, cocktails and PAC plasmid used as described above—the use of a nucleic acid extraction control (NEC). In one embodiment, the NEC is an M13K07 phage, which is included in the test sample prior to nucleic acid extraction. If the nucleic acid extraction is adequate for the purposes of detecting contaminant DNA or RNA, then the NEC nucleic acid (e.g., M13K07 nucleic acid) is detected via Q-PCR in the "spiked" test sample. In a particular embodiment, the Q-PCR reaction admixture contains a target contaminant specific forward oligonucleotide primer, target contaminant specific oligonucleotide detection probe, an artificial oligonucleotide detection probe, such as the unique detection probe (UDP) described above, a target contaminant specific reverse oligonucleotide primer, an NEC specific forward oligonucleotide primer, an NEC specific oligonucleotide detection probe, and an NEC specific reverse oligonucleotide primer. In one embodiment, the test sample is taken from a therapeutic protein production cell culture, which is spiked with an NEC (e.g., an M13K07 phage) prior to nucleic acid extraction and subsequent Q-PCR analysis.

In a specific embodiment, the target contaminant is a rodent parvovirus, in which case (1) the target contaminant specific forward oligonucleotide primer is a rodent parvovirus specific forward oligonucleotide primer, more specifically comprising the sequence of SEQ ID NO:1; (2) the target contaminant specific oligonucleotide detection probe is a rodent parvovirus specific oligonucleotide detection probe, more specifically comprising the nucleic acid sequence of SEQ ID NO:2; (3) the artificial oligonucleotide detection probe is the unique detection probe (UDP), more specifically comprising the nucleic acid sequence of SEQ ID NO:3; (4) the target contaminant specific reverse oligonucleotide primer is a rodent parvovirus specific reverse oligonucleotide primer, more specifically comprising the nucleic acid sequence of SEQ ID NO:4; (5) the NEC specific forward oligonucleotide primer is an M13 forward oligonucleotide primer, more specifically comprising the nucleic acid sequence of SEQ ID NO:5; (6) the NEC specific oligonucleotide detection probe is an M13 detection probe, more specifically comprising the nucleic acid sequence of SEQ ID NO:6; and (7) the NEC specific reverse oligonucleotide primer is an M13 reverse oligonucleotide primer, more specifically comprising the nucleic acid of SEQ ID NO:8. In one embodiment of the method, if an NEC Q-PCR signal is detected (i.e, the signal is within the expected recovery range), then one can assume that the nucleic acid extraction of the test sample was successful. On the other hand, if no NEC signal is detected (i.e., the signal is outside the expected recovery range), then one can assume that the nucleic acid extraction of the test sample failed, and any negative Q-PCR target contaminant signal is considered invalid (i.e., false negative).

DETAILED DESCRIPTION OF THE INVENTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated by reference in their entirety. Other embodiments will become apparent from a review of the ensuing detailed description.

In order that the invention herein described may be fully understood, the following detailed description is set forth.

The invention relates to improved materials and methods for detecting any biological contaminant in any cell culture that produces a therapeutic protein. Specifically, the invention relates to quantitative polymerase chain reaction (Q-PCR) materials and methods that incorporate a positive amplification control element or step that is easily detected to eliminate false positives.

PCR and Quantitative PCR

As used herein, the phrase "polymerase chain reaction" ("PCR") means a method for making copies of a nucleic acid (e.g., DNA) by employing multiple cycles of denaturation (the separation of template DNA strands), annealing (the hybridization of single stranded oligonucleotides to the single stranded template DNA strands), and DNA synthesis (DNA polymerase catalyzes the synthesis of a new DNA strand primed from the 3-prime end of the hybridized oligonucleotide, using the template DNA strand as a template). For amplification to occur, at least two different oligonucleotide primers (known as "primer" for short) are used in the PCR reaction. One primer, which is generally called the forward primer, hybridizes to the antisense strand of the template DNA and forms the 5-prime end of the newly synthesized sense strand. The other primer, which is generally called the reverse primer, hybridizes to the sense strand of the template DNA and forms the 5-prime end of the newly synthesized antisense strand. At each cycle, each template strand is copied to form a new double stranded DNA molecule, which is also known as an "amplicon". Thus, with non-limiting amounts of oligonucleotide primers, DNA polymerase (i.e., Taq polymerase or other thermostable DNA polymerase; see Innis et al., DNA sequencing with Thermus aquaticus DNA polymerase and direct sequencing of polymerase chain reaction-amplified DNA, 85(24) Proc. Natl. Acad. Sci. USA. 9436-40 (1988)), and nucleotide triphosphates, the number of DNA molecules (templates and amplicons) doubles at each cycle. PCR is described in U.S. Pat. No. 4,683,202 (issued Jul. 28, 1987). See also PCR Primer: A Laboratory Manual (Carl W. Dieffenbach & Gabriela S. Dveksler eds., 1995).

As used herein, the term "cycle" means a single round of (1) DNA strand melting called "denaturation", followed by (2) hybridizing of oligonucleotide primers to the resultant single-stranded DNA by the rules of base-pairing, a process called "annealing", and (3) polymerization of a new strand of DNA starting at the 3-prime end of the oligonucleotide primer and moving in a 5-prime to 3-primer direction, a process called "amplification" or "extension". Generally, polymerization uses a DNA polymerase enzyme, such as Taq polymerase, to catalyze the formation of phosphodiester bonds between adjacent deoxynucleotide triphosphates ("dNTPs"), which are laid down along the exposed single-stranded template DNA by hydrogen bonding according to the rules of base pairing. Denaturation, annealing, and amplification are performed at certain temperatures based in part upon the GC content of the DNA template and the oligonucleotide primers, and the length of the DNA strand to be copied. The temperature of denaturation and annealing, as well as the ionic strength of the reaction buffer controls the stringency of hybridization and the fidelity of DNA copying.

"Quantitative PCR" or "qPCR" or "Q-PCR" (also known as "real time PCR") is a type of PCR that enables the monitoring of amplicon formation during the PCR cycling process. Q-PCR can be used to quantify the amount of a specific template DNA in a sample. Q-PCR incorporates at least one oligonucleotide detection probe in the reaction mix in addition to the forward oligonucleotide primer and the reverse oligonucleotide primer. The detection probe is a single-stranded oligonucleotide that hybridizes to the sense or antisense strand of the target template DNA somewhere between the forward primer binding site and the reverse primer binding site. During the annealing step, the oligonucleotide detection probe anneals to the single-stranded template. As polymerization occurs, the probe is cleaved and degraded by the 5-prime nuclease activity of the DNA polymerase. Thus, as amplification of the specific template sequence occurs, detection probes are degraded at an exponential rate.

Q-PCR oligonucleotide detection probes are generally constructed with an attached fluorophore (also known as a reporter fluorescent dye, or simply "reporter") and an attached quencher. In most cases, the fluorophore is attached at or near the 5-prime end of the oligonucleotide and the quencher is attached at or near the 3-prime end of the oligonucleotide. However, any workable architecture may be used in the practice of this invention. When the oligonucleotide detection probe is intact, the fluorophore and the quencher are proximal such that the quencher absorbs light emitted by the excited fluorophore, thereby significantly reducing detectable fluorophore emission. When the oligonucleotide detection probe is cleaved or degraded, the fluorophore and quencher are released and consequently separated in space. The quencher is no longer close enough to quench the fluorophore emission. As more specific amplicons are formed, more oligonucleotide detection probes are cleaved, more fluorophores and quenchers are released such that more fluorophore/quencher pairs are separated, and the fluorescence emission amplitude increases. In other words, an increasing fluorophore emission signal correlates to the amount of specific target DNA in the sample. For a review of Q-PCR, see Ian M. Mackay et al., Survey and Summary: Real-Time PCR in Virology, 30(6) Nucleic Acids Research 1292-1305 (2002).

Fluorescence quenching can occur by direct contact between reporter and quencher (also known as static quenching) or by fluorescence resonance energy transfer (FRET) between the reporter and quencher when the reporter and quencher are both within the Förster radius of each other. A specific fluorophore can be excited by one or more specific wavelengths of light, or a range of wavelengths with a maximum. This is called the excitation wavelength. After a fluorophore is excited, it returns to a ground state and emits light at a longer wavelength than the excitation wavelength. This is called the emission wavelength. During FRET, a second fluorophore, dye, lanthanide series molecule, or the like, which has an absorbance spectrum that matches or overlaps the emission spectrum of the fluorophore, absorbs the light emitted by the excited fluorophore within the Förster radius, thereby quenching or reducing the wavelength of the fluorophore emission. Contact or static quenching results when the reporter and quencher form a ternary complex at the ground state of the fluorophore. This ternary complex is non-fluorescent, i.e., essentially non-excitable and therefore does not emit light at an expected emission wavelength.

For a review on static quenching and FRET, see Salvatore A. E. Marras et al., Efficiencies of Fluorescence Resonance Energy Transfer and Contact-Mediated Quenching in Oligonucleotide Probes, 30(21) Nucleic Acids Research e122, pp. 1-8 (2002). Marras et al. also discuss the selection of reporter/quencher pairs for use in the application of Q-PCR. Nucleic Acids The terms "polynucleotide", "oligonucleotide", "probe", "primer" or "nucleotide primer" or "oligonucleotide primer", "template" or "template nucleic acid" or "template DNA" are used herein according to their ordinary meaning to one of ordinary skill in the molecular biological arts. For a detailed explanation of each, see for example PCR Primer: A Laboratory Manual (Carl W. Dieffenbach & Gabriela S. Dveksler eds., 1995)

As used herein, "amplicon" refers to a DNA product resulting from the amplification of a template nucleic acid sequence through PCR. As PCR proceeds and template is amplified, newly formed DNA amplicons serve as templates for subsequent rounds of DNA synthesis.

Cell Cultures

The invention is directed to an improved Q-PCR method for detecting biological contaminants in a cell culture. Cell cultures are often used to produce complex biological molecules for therapeutic use, such as antibodies, trap molecules and Fc fusion proteins. These cultures should remain free of biological contaminants. The detection of contaminants is important to determine whether a particular batch is to be discarded or subject to remediation.

Cell cultures include culture media and cells usually derived from a single cell line. Here, the cell line comprises cells capable of producing a biotherapeutic protein. Examples of cell lines that are routinely used to produce protein biotherapeutics include inter alfa primary cells, BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, 3T3 cells, 293 cells, Per.C6 cells and chicken embryo cells. A Chinese hamster ovary (CHO) cell line or one or more of several specific CHO cell variants, such as the CHO-K1 cell line are optimized for large-scale protein production. The EESYR® cell line is a specialized CHO cell line optimized for enhanced production of proteins of interest. For a detailed description of EESYR® cells, see U.S. Pat. No. 7,771,997 (issued Aug. 10, 2010).

"Cell culture" or "culture" means the growth and propagation of cells outside of a multicellular organism or tissue. Suitable culture conditions for mammalian cells are known in the art. See for example *Animal cell culture: A Practical Approach* (D. Rickwood, ed., 1992). Mammalian cells may be cultured in suspension or attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture. Cell culture media or concentrated feed media may be added to the culture continuously or at intervals during the culture (i.e., batch fed). For example, a culture may be fed once per day, every other day, every three days, or may be fed when the concentration of a specific medium component, which is being directly or indirectly monitored, falls outside a desired range.

Animal cells, such as CHO cells or EESYR® cells, may be cultured in small scale cultures, such as in 125 ml containers having about 25 ml of media, 250 ml containers having about 50 to 100 ml of media, 500 ml containers having about 100 to 200 ml of media. Alternatively, cultures may be large scale such as for example 1000 ml containers having about 300 to 1000 ml of media, 3000 ml containers having about 500 ml to 3000 ml of media, 8000 ml containers having about 2000 ml to 8000 ml of media, and 15000 ml containers having about 4000 ml to 15000 ml of media. Cultures for manufacturing can contain 10,000 L of media or more. Large scale cell cultures, such as for clinical manufacturing of protein therapeutics, are typically maintained for days or weeks while the cells produce the desired protein(s). During this time, samples of the culture may be removed and tested for the presence of biological contaminants.

Production of Therapeutic Proteins

The cell culture which is monitored for biological contamination may be used to produce a protein or other biological molecule of interest, such as a therapeutically effective antibody or other biopharmaceutical drug substance. The protein product (protein of interest) can be inter alfa an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgA antibody, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody.

The protein of interest can be a recombinant protein that contains an Fc moiety and another domain, (e.g., an Fc-fusion protein). An Fc-fusion protein can be a receptor Fc-fusion protein, which contains one or more of one or more extracellular domain(s) of a receptor coupled to an Fc moiety. In some case, the Fc moiety comprises a hinge region followed by a CH2 and CH3 domain of an IgG. In some cases, the receptor Fc-fusion protein contains two or more distinct receptor chains that bind to either a single ligand or multiple ligands. For example, an Fc-fusion protein is a trap, such as for example an IL-1 trap (e.g., rilonacept, which contains the IL-1RAcP ligand-binding region fused to the Il-1R1 extracellular region fused to an Fc domain of hIgG1; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to an Fc domain of hIgG1; see U.S. Pat. Nos. 7,087,411 and 7,279,159).

The present invention is not limited to any particular type of cell or cell line for protein production. Examples of cell types suitable for protein production include mammalian cells, such as a CHO-derived cell like EESYR®, insect cells, avian cells, bacterial cells, and yeast cells. The cells may be stem cells or recombinant cells transformed with a vector for recombinant gene expression, or cells transfected with a virus for producing viral products. The cells may contain a recombinant heterologous polynucleotide construct that encodes a protein of interest. That construct may be an episomal (such as an extrachromosomal plasmid or fragment) or it may be physically integrated into the genome of the cell. The cells may also produce a protein of interest without having that protein encoded on a heterologous polypeptide construct. In other words, the cell may naturally encode the protein of interest, such as a B-cell producing an antibody. Methods and vectors for genetically engineering cells or cell lines to express a protein of interest are well known to those of ordinary skill in the art. For example, various techniques are illustrated in *Current Protocols in*

Molecular Biology, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69. A wide variety of cell lines suitable for growth in culture are available from the American Type Culture Collection (Manassas, Va.) and commercial vendors.

The cells may also be primary cells, such as chicken embryo cells, or primary cell lines. Examples of useful cells include BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, chicken embryo cells, NS-1 cells, MRC-5 cells, WI-38 cells, BHK cells, 293 cells, Per.C6 cells and CHO cells. In various embodiments, the cell line is a CHO cell derivative, such as CHO-K1, CHO DUX B-11, CHO DG-44, Veggie-CHO, GS-CHO, S-CHO, CHO lec mutant lines, or an EESYR® cell line.

In one particular scenario, the cell is a CHO cell derivative such as a EESYR® cell that ectopically (heterologously) expresses a protein. That protein comprises an immunoglobulin heavy chain region, such as a CH1, CH2, or CH3 region. In one embodiment, the protein comprises a human or rodent immunoglobulin CH2 and CH3 region. In one embodiment, the protein comprises a human or rodent immunoglobulin CH1, CH2, and CH3 region. In one embodiment, the protein comprises a hinge region and a CH1, CH2, and CH3 region. In a specific embodiment, the protein comprises an immunoglobulin heavy chain variable domain. In a specific embodiment, the protein comprises an immunoglobulin light chain variable domain. In a specific embodiment, the protein comprises an immunoglobulin heavy chain variable domain and an immunoglobulin light chain variable domain. In a specific embodiment, the protein is an antibody, such as a human antibody, a rodent antibody, or a chimeric human/rodent antibody (e.g., human/mouse, human/rat, or human hamster).

A protein production phase of a cell culture can be conducted at any scale of culture, from individual flasks and shaker flasks or wave bags, to one-liter bioreactors, and to large scale industrial bioreactors. A large scale process can be conducted in a volume of about 100 liters to 20,000 liters or more. One or more of several means may be used to control protein production, such as temperature shift or chemical induction. The growth phase of the cell may occur at a higher temperature than the production phase during which protein is expressed and/or secreted. For example, the growth phase may occur at a first temperature of about 35° C. to 38° C., and the production phase may occur at a second temperature of about 29° C. to 37° C., optionally from about 30° C. to 36° C. or from about 30° C. to 34° C. In addition, chemical inducers of protein production, such as caffeine, butyrate, tamoxifen, estrogen, tetracycline, doxycycline, and hexamethylene bisacetamide (HMBA), may be added concurrently, before, or after a temperature shift. If inducers are added after a temperature shift, they can be added from one hour to five days after the temperature shift, such as from one to two days after the temperature shift. Production cell cultures may be run as continuous feed culture system, as in a chemostat (see C. Altamirano et al., Biotechnol. Prog. 2001 November-December; 17(6):1032-41), or according to a fed-batch (batch-fed) process (Huang, 2010).

Therapeutic Protein Products

As used herein "peptide," "polypeptide" and "protein" are used interchangeably throughout and refer to a molecule comprising two or more amino acid residues joined to each other by a peptide bond. Peptides, polypeptides and proteins may also include modifications such as glycosylation, lipid attachment, sulfation, gamma-carboxylation of glutamic acid residues, alkylation, hydroxylation and ADP-ribosylation. Peptides, polypeptides, and proteins can be of scientific or commercial interest, including protein-based drugs. Peptides, polypeptides, and proteins include, among other things, antibodies and chimeric or fusion proteins. Peptides, polypeptides, and proteins are produced by recombinant animal cell lines using cell culture methods.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region.

The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one epitope. Bispecific antibodies are generally described in US Patent Application Publication No. 2010/0331527, which is incorporated herein by reference.

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) Structure 2:1121-1123).

An antibody or antigen-binding portion thereof may be part of a larger immunoadhesion molecule, formed by covalent or noncovalent association of the antibody or an antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab')2 fragments, can be prepared from whole antibodies using conventional techniques, such as by papain or pepsin digestion of whole antibodies. Moreover, antibodies, antibody portions and immunoadhesion molecules can be obtained using standard recombinant DNA techniques (see Sambrook et al., 1989).

The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, does not include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc-fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s). For example, an Fc-fusion protein is a trap, such as for example an IL-1 trap (e.g., rilonacept, which contains the IL-1RAcP ligand binding region fused to the IL-1R1 extracellular region fused to Fc of hIgG1; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

Biological Contaminants

As used herein, the term "biological contaminant" means any unwanted, undesirable, harmful or potentially harmful biological entity. Those entities include inter alfa prions (the etiological cause of bovine/transmissible spongiform encephalopathy), virions, viruses, mycoplasma, other bacteria, contaminating metazoan cells, DNAs, RNAs, transposons, other transposable elements, yeast, other fungi, algae, protists, and other adventitious and endogenous agents. Of particular concern to biotherapeutic production processes that use rodent cells (like CHO cells and derivatives of CHO cells) are adventitious viruses associated with cells or media or manufacturing raw materials. Contamination of cell culture bulk process materials and the resultant drug product poses a direct risk top the patient as well as the indirect risk of interrupting the supply of medicine.

A non-exhaustive list of adventitious and/or endogenous agents that can infect CHO cells cultures includes: single stranded (−) RNA viruses such as cache valley virus, influenza AB virus, parainfluenza 1/2/3, simian virus 5, mumps virus, bovine respiratory syncytial virus, and vesicular stomatitis virus; single stranded (+) RNA viruses such as bovine coronavirus, vesivirus 2117, encephalomyocarditis virus, coxsackie virus B-3, semliki forest virus, and sindbis virus; double stranded RNA viruses such as bluetongue virus, epizootic hemorrhagic disease virus, and reovirus 1/2/3; single stranded DNA viruses, such as porcine circovirus 1, and the particularly problematic parvoviruses that include mice minute virus (also known as minute virus of mice); and double stranded DNA viruses such as adenovirus and pseudorabies virus. Of these potential adventitious agents, four viruses dominate bulk harvest samples from CHO cell cultures across various manufacturers. Those viruses are reovirus type 2, cache valley virus, epizootic disease hemorrhagic virus, and the rodent parvovirus mouse minute virus. For a detailed review of adventitious viral contaminations of CHO cell cultures, see Andreas Berting et al., Virus Susceptibility of Chinese Hamster Ovary (CHO) Cells and Detection of Viral Contaminations by Adventitious Agent Testing, 106(4) Biotechnology and Bioengineering 598-607 (2010), and Andrew Kerr & Raymond Nims, Adventitious Viruses Detected in Biopharmaceutical Bulk Harvest Samples over a 10 Year Period, 64(5) PDA Journal of Pharmaceutical Science & Technology 481-485 (2010).

Adventitious agent testing falls into two general categories. The first is a classical virology approach using an in vitro virus assay. Here, the test sample is applied to an indicator cell line, the cells are incubated and passaged for 14 to 28 days, and then end-points, such as cytopathic effect or hemagglutination, are measured (Berting, 2010). The second is a PCR-based assay, which measures in real-time the presence of nucleic acids associated with adventitious or endogenous agents. For example, see Zhan et al., Detection of Minute Virus of Mice Using Real Time Quantitative PCR in Assessment of Virus Clearance during the Purification of Mammalian Cell Substrate Derived Biotherapeutics, 30(4) Biologicals 259-270 (2002).

Mouse minute virus (a.k.a. MMV, minute virus of mouse, or MVM) poses a special problem for biotherapeutic manufacturing. Both the U.S. Food and Drug Administration (FDA) and the European Medicines require testing specifically for MVM. This virus is a member of the parvoviridae family (parvovirus) and common in mice. It is excreted in urine and feces, is robust, and is persistent in the environment. It easily can be introduced into biotherapeutic manufacturing processes. See Moody et al., Mouse Minute Virus (MMV) Contamination—A Case Study: Detection, Root Cause Determination, and Corrective Actions, 65(6) PDA Journal of Pharmaceutical Science and Technology 580-288 (2011). Other rodent parvoviruses may negatively impact cell culture-based biopharmaceutical production. In addition to the prototype MVM strain, those rodent parvoviruses include inter alia the MVM immunosuppressive strain and cutter strain, mouse parvovirus 1a (MPV-1a), MPV-1b, MPV-1c, hamster parvovirus, toolan's parvovirus (parvovirus H-1), kilham rat virus, rat parvovirus 1a, rat minute virus, and the Umass strain of rat virus L. See S.F. Cotmore & P. Tattersal, The Autonomously Replicating Parvoviruses of Vertebrates, 33 Advances in Virus Research 91-174 (1987), and Jacoby et al., Rodent Parvovirus Infections, 46(4) Lab Anim Sci. 370-80 (1996).

These parvoviruses share a conserved nucleic acid sequence called NS-1 (NS1), which encodes a large non-structural protein involved in the amplification of the viral genome. The conserved NS1 nucleotide sequence from MVM is depicted in SEQ ID NO:9. Nucleotides 875-956 of that sequence are at least 97% conserved across a wide array of rodent parvovirus NS1 sequences, and therefore serve as good target sequences for PCR-based adventitious and endogenous agent testing. PCR-based testing for rodent parvoviruses (and other adventitious and endogenous agents) can be performed on raw materials, pre-harvested culture media, at various points along the bulk process purification of the biotherapeutic molecule, and at the formulation and packaging stages. The detection of a contaminant may require remediation steps such as disposal of contaminated material, replacement of raw material, and decontamination of the facility.

In addition to testing for adventitious agents, endogenous agents, and other biological contaminants, which enables corrective and preventative actions (CAPAs) during manufacturing, special manufacturing and bulk process steps (i.e., unit operations) may be employed to eliminate, reduce, or inactivate viral contaminants. Chemical inactivation, virus retentive filtration, and chromatography have been shown to be effective in reducing herpesvirus, retrovirus, and parvovirus in harvested or partially purified cell culture fluid. The chemical inactivation step most frequently used is a low pH treatment, which some of ordinary skill in the art believe is due to the denaturation of virus envelope proteins. Protein A, hydroxyapatite, cation exchange and anion exchange chromatography steps have all been shown to remove virus to some extent. See for example Miesegaes et al., Analysis of Viral Clearance Unit Operations for Monoclonal Antibodies, 106(2) Biotechnology and Bioengineering 238-246 (2010), and Liu et al., Recovery and Purification Process Development for Monoclonal Antibody production, 2(5) mAbs 480-499 (2010).

Q-PCR Testing: Positive and Negative Controls

Tests for biological contaminants should be properly controlled to ensure accuracy, reliability, and believability. As used herein, a "negative control" incorporates most or all experimental reagents and conditions, but without the test sample. The test sample may be replaced with a buffer or sham culture media known not to contain the biological contaminant-of-interest. Further as used herein, the "negative control" should generate a negative result for the biological contaminant. If the negative control generates a positive biological contaminant result, then the skilled technician or scientist can assume that a positive result from the parallel test sample might not accurately reflect whether the test sample contains the biological contaminant.

As used herein, one or more "positive controls" are employed assess whether the experimental conditions are adequately operable to detect the biological contaminant. Positive controls can be used at any step along the experimental process to ensure that each step is operating, and to determine at which step the process breaks down.

In some embodiments, a positive control is employed at the nucleic acid extraction step to assess whether the intended extraction of any biological contaminant nucleic acid was efficient enough to detect the biological contaminant. Such a positive control is called a "nucleic acid extraction control" or "NEC". In some cases, the NEC is selected to mimic the target biological contaminant in terms of protein-nucleic acid structure. If the NEC is extracted in a manner sufficient to be detected, then the technician may assume that the target biological nucleic acid was also extracted in a manner sufficient to be detected. In one embodiment, the NEC is a single stranded DNA phage, not altogether unlike parvoviruses.

In a specific embodiment, the NEC is an M13 bacteriophage, which is composed of a circular single stranded DNA of about 6407 nucleotides. In a more specific embodiment, the NEC is the M13K07 strain, which is a generally available molecular biology reagent used for cloning and other laboratory purposes. See van Wezenbeek et al., *Nucleotide Sequence of the Filamentous Bacteriophage M13 DNA Genome: Comparison with Phage fd,* 11(1-2) Gene 129-148 (1980). A nucleotide sequence of the M13K07 phage is depicted in SEQ ID NO:8. While the M13 bacteriophage, or the M13K07 bacteriophage strain can be used as the NEC in specific embodiments, the invention is in no way limited to using that particular reagent as an NEC. One of ordinary skill in the art may substitute another reagent as an NEC in the practice of this invention without departing from the scope of the invention (e.g., MS2 phage for Reverse Transcriptase-PCR assays; see Kothapalli et al., Problems associated with product enhancement reverse transcriptase assay using bacteriophage MS2 RNA as a template, 109(2) J. Virol. Methods 203-207 (2003)).

In some embodiments of the invention, a positive control is employed at the PCR amplification step to assess whether the PCR reagents (including primers) and PCR steps are/ were sufficient to detect the biological contaminant template nucleic acids. Such a positive control is called a "plasmid amplification control" or "PAC". In some cases, the PAC is selected or designed to match the target biological contaminant nucleic acid sequence, and exactly match the test sample forward and reverse oligonucleotide primers. In a specific embodiment, the PAC additionally contains a "unique sequence" that is not found in the target biological contaminant nucleic acid. In a more specific embodiment, the unique sequence is not found in nature. A "unique" nucleic acid polymer is designed to specifically anneal to this unique sequence and incorporate into amplicon copies of the unique sequence during PCR. The "unique" nucleic acid polymer is designed to not recognize or anneal to any naturally occurring parvovirus under hybridization conditions employed in the operation of the subject assay. In one embodiment, the "unique" nucleic acid polymer comprises from 17 to 20 nucleotides, wherein no more than seven (7) to 10 internal consecutive nucleotides and no more than six (6) consecutive three-prime nucleotides are identical to any parvovirus sequence. In one embodiment, the "unique" nucleotide polymer comprises from 17 to 20 nucleotides, wherein no more than 7 to 10 consecutive nucleotides and no more than six (6) consecutive three-prime nucleotides are identical to any parvovirus sequence set forth in SEQ ID NOs: 9 and 12-37.

This unique sequence enables the skilled technician to distinguish between a bona fide target biological contaminant sequence, and cross-contamination of the test Q-PCR reaction with the PAC plasmid.

In one embodiment, the PAC (as a plasmid, a.k.a. PAC plasmid) is included in an identical but separate Q-PCR reaction to control for PCR amplification. The PAC reaction use the exact same oligonucleotide primers and probes as is used in the test sample Q-PCR reaction to accurately reflect amplification of an actual target biological contaminant nucleic acid. The test sample Q-PCR reaction and the separate PAC plasmid Q-PCR reaction include a target detection probe and a unique sequence probe. The PAC reaction, if properly functioning, is expected to generate a positive target signal and a positive unique sequence signal. Obtaining a positive target signal and a positive unique sequence signal in the PAC plasmid-containing reaction indicates that the test sample Q-PCR reagents and conditions are adequately working to produce a positive target signal in the test sample whenever a target biological contaminant nucleic acid is present.

Therefore, the PAC acts as a control for proper PCR amplification. If a negative target signal is obtained in the test sample, but the PAC shows a positive target signal, then the skilled technician can assume that no detectable target contaminant DNA is present in the test sample. Conversely, if a positive target sequence signal and a positive unique sequence signal are obtained in the test sample, then the technician can assume that the PAC plasmid cross-contaminated the test sample, and therefore the positive target sequence signal may be a false positive.

DETAILED DESCRIPTION OF SEVERAL EMBODIMENTS

In some embodiments, an improved positive control system (i.e., compositions and methods) is provided for detecting biological contaminants by the use of polymerase chain reaction, more specifically, Q-PCR.

In one aspect, the invention provides a unique sequence probe (USP) to detect the positive amplification control plasmid (PAC plasmid). The USP contains an artificial nucleotide sequence capable of hybridizing to the unique artificial plasmid-specific sequence (a.k.a. unique sequence, or PACP unique sequence, or UAPS), a fluorophore, and a quencher. In a specific embodiment, the artificial nucleotide sequence capable of hybridizing to the UAPS comprises the nucleic acid sequence of SEQ ID NO:3 (5'-TGTC-GATGGCGAATGGCTA-3'), which is the anti-sense to the UAPS sense strand sequence (e.g., i.e., SEQ ID NO:10-5'-TAGCCATTCGCC ATCGACA-3'.)

As described above, Q-PCR detection probes contain a fluorophore and a quencher. Quenching may be by contact quenching or by FRET, depending on the fluorophore/quencher pair. Here, a fluorophore and a quencher are covalently attached the USP oligonucleotide. In one embodiment, the fluorophore has an excitation wavelength of 495 nm to 680 nm and an emission wavelength of 515 nm to 710 nm. In some embodiments, the fluorophore has an excitation wavelength of 495 nm, 538 nm, or 646 nm and an emission wavelength of 520 nm, 554 nm, or 669 nm, respectively. In some embodiments, the quencher is a dye with an absorbance peak of 430 nm to 672 nm. Examples of useful quenchers include DDQ®-I, Dabcyl, Eclipse®, Iowa Black FQ®, BHQ®-1, QSY®-7, BHQ®-2, DDQ®-II, Iowa Black RQ®, QSY®-21, and DHQ®-3. In a specific embodiment, the fluorophore is fluorescein amidite (FAM; described in U.S. Pat. No. 5,583,236 (issued Dec. 10, 1996), which has an absorbance maximum of about 495 nm and an emission maximum of about 520 nm, and the quencher is Black Hole Quencher®-1 (BHQ®-1, Biosearch Technologies, Inc., Petaluma, Calif.), which absorbs at 480 nm to 580 nm. BHQ®-1 quenches via FRET and contact quenching. Generally, but not always, the quencher is attached via an ether bond to the 3-prime hydroxyl group of the oligonucleotide, and the fluorophore is attached via an ester bond to the 5-prime phosphate group of the oligonucleotide.

In another aspect, the invention provides a mixture of Q-PCR reagents comprising multiple oligonucleotides and probes, useful for the detection of a biological contaminant in cell cultures, raw materials, partially purified and purified biological molecules, and the like. In one embodiment, the biological contaminant is a DNA virus, more specifically a parvovirus, and more specifically still, a rodent parvovirus, such as MVM. The parvovirus contains an NS1 gene having a nucleic acid sequence that is at least 88% identical to any sequence listed in Table 1. In another embodiment, the parvovirus contains an NS1 gene having a nucleic acid sequence that is at least 97% identical to the sequence set forth in SEQ ID NO:9 (i.e., Mouse Minute Virus (MVM) NS1 gene). In yet another embodiment, the parvovirus contains an NS1 gene comprising the consensus sequence of SEQ ID NO:37.

TABLE 1

Parvoviridae NS1 Sequences

| Gene Name | SEQ ID NO: | Identity to SEQ ID NO: 9 |
| --- | --- | --- |
| MVM lymphotropic variant | 12 | 97% |
| Mouse parvovirus 4b | 13 | 96% |
| Mouse parvovirus 4a | 14 | 96% |
| Mouse parvovirus 1b | 15 | 96% |
| MVM immune-suppressive variant | 16 | 96% |
| Mouse parvovirus 1 | 17 | 96% |
| Mouse parvovirus 5a | 18 | 96% |
| Mouse parvovirus UT | 19 | 96% |
| Mouse parvovirus 1e | 20 | 96% |
| Mouse parvovirus 1c | 21 | 95% |
| Hamster parvovirus | 22 | 95% |
| Mouse parvovirus 3 | 23 | 95% |
| Mouse minute virus | 24 | 95% |
| MVM, strain M | 25 | 95% |
| Parvovirus LuIII | 26 | 90% |
| Rat parvovirus UT | 27 | 89% |
| Kilham rat virus | 28 | 89% |
| Rat minute virus 1c | 29 | 89% |
| Rat minute virus 1b | 30 | 89% |
| Rat minute virus 1a | 31 | 89% |
| H-1 parvovirus | 32 | 89% |
| Rat minute virus isolate NTU1 | 33 | 89% |
| Parvovirus h-1 | 34 | 89% |
| Rat minute virus isolate NTU2 | 35 | 88% |
| Rat minute virus 2a | 36 | 88% |
| Consensus NS1 | 37 | 100% |

In a specific embodiment, the mixture contains (1) a rodent parvovirus specific forward oligonucleotide primer; (2) a rodent parvovirus specific oligonucleotide detection probe; (3) an artificial oligonucleotide detection probe, such as the USP; and (4) a rodent parvovirus specific reverse oligonucleotide primer. Such a mixture may be used in both the test sample and the positive control sample. In a more specific embodiment, the oligonucleotide primers and parvovirus specific oligonucleotide detection probe hybridize to an NS1 sequence, such as for example the NS1 sequence set forth in SEQ ID NO:9. In a more specific embodiment, the (1) forward primer comprises the sequence of SEQ ID NO:1; (2) the parvovirus specific oligonucleotide detection probe comprises the sequence of SEQ ID NO:2; (3) the artificial probe is a USP and comprises the sequence of SEQ ID NO:3; and (4) the reverse primer comprises the sequence of SEQ ID NO:4.

As described above, the USP contains a fluorophore and a quencher, so that amplicons containing that sequence, i.e., PAC DNA, can be detected in real time as Q-PCR proceeds. In a similar manner, the parvovirus specific detection probe contains an oligonucleotide with a fluorophore and quencher covalently attached. In practice, the fluorophore emission wavelength of the parvovirus detection probe should be different than the emission wavelength of the USP to differentiate between a true parvovirus positive signal and a false positive due to contamination of the test sample with a PAC plasmid or other PACP (e.g., a PACP contaminating amplicon). Thus, in those embodiments in which the USP fluorophore is FAM, the fluorophore attached to the parvovirus detection probe oligonucleotide should have an emission wavelength other than about 520 nm. In a specific embodiment, the fluorophore attached to the rodent parvovirus specific oligonucleotide detection probe is VIC® Dye (Life Technologies, Inc., Carlsbad, Calif.), which has an absorbance maximum at 538 nm and an emission maximum of about 554 nm. Here, the quencher can be a FRET quencher or a contact quencher. In one embodiment the quencher is a minor groove binding non-fluorescent quencher (MGBNFQ) (see Sylvain et al., Rapid Screening for HLA-B2 7 by a TaqMan-PCR Assay Using Sequence-Specific Primers and a Minor Groove Binder Probe, a Novel Type of TaqMan™ Probe, 287(1-2) Journal of Immunological Methods 179-186 (2004)).

The mixture of primers and probes described above is used to test and distinguish a positive amplification control construct from a bona fide parvovirus contaminant. In some embodiments, the mixture of primers also includes a set of primers and a probe to detect a nucleic acid extraction control (NEC). In a particular embodiment, the NEC is an M13 bacteriophage, for example the M13K07 strain (SEQ ID NO:8). Thus, in some embodiments, in addition to the parvovirus primers and probe and the UPS probe, the mixture of primers and probes contains (5) an M13 specific forward oligonucleotide primer; (6) an M13 specific oligonucleotide detection probe; and (7) an M13 specific reverse oligonucleotide primer.

In some embodiments, the M13 primers and probe hybridize to the sequence of SEQ ID NO:8. In a specific embodiment, the M13 specific forward oligonucleotide primer comprises the nucleic acid sequence of SEQ ID NO:5; the M13 specific oligonucleotide detection probe comprises the nucleic acid sequence of SEQ ID NO:6; and the M13 specific reverse oligonucleotide primer comprises the nucleic acid sequence of SEQ ID NO:7. As in the case of the non-overlapping fluorophore emission spectra for the parvovirus probe and the USP, the NEC probe contains a fluorophore that emits light at a non-overlapping spectrum. In a specific embodiment, the fluorophore attached to the M13 specific oligonucleotide detection probe is Cy5, a cyanine dye having an absorbance maximum of about 650 nm and an emission maximum of about 670 nm (see Southwick et al., Cyanine Dye Labeling Reagents: Carboxymethylindocyanine Succinimidyl Esters, 11 Cytometry, 418-430 (1990)). Here, the quencher may operate via FRET or contact quenching. In one embodiment, the quencher is Black Hole Quencher®-2 (BHQ®-2, Biosearch Technologies, Inc., Petaluma, Calif.), which absorbs at a maximum of about 579 nm, and quenches in the range of about 550 nm to about 650 nm.

In another aspect, the invention provides a method of detecting a biological contaminant in a biological molecule production process. The biological contaminant more specifically comprises a parvovirus, more specifically a rodent parvovirus, and most specifically those parvoviruses sharing at least 97% identity to the MVM NS1 gene. In some embodiments, the NS1 gene comprises the sequence of SEQ ID NO:9. In one embodiment, the biological molecule production process is a mammalian cell culture process for manufacturing an antibody, a trap molecule, or other therapeutic antibody. A test sample is taken from the cell culture (or bulk ingredients) and extracted for nucleic acids. In some cases, the test sample is spiked with an NEC, such as M13 (e.g., SEQ ID NO:8), to serve as a control for proper extraction of nucleic acids prior to Q-PCR. The method comprises the steps of (1) combining (a) the nucleic acid sample extracted from the test sample, (b) oligonucleotide primers and probes (as described above), and (c) a DNA polymerase, preferably a thermostable DNA polymerase with 5' exonuclease activity, such as Taq polymerase; (2) subjecting that combination to polymerase chain reaction (PCR); and (3) monitoring the production of various amplicons via fluorescence emission amplitude.

Formation of specific amplicons is correlated to the presence and amount of various template nucleic acids in the test sample. The specific amplicons include (1) target amplification polynucleotides (TAPs), such as for example rodent parvovirus sequences (e.g., those biological contaminants containing NS1 sequences), (2) nucleic acid extraction control (NEC), such as for example an M13 (e.g., M13K07) polynucleotides (NECPs), and (3) plasmid amplification control polynucleotides (PACPs), such as the unique artificial plasmid-specific sequence (UAPS). If TAPs and NECPs are produced, and PACPs are not produced, then it can be concluded that the test sample contains a biological contaminant and does not contain a cross-contaminating positive amplification control plasmid. However, if both TAPs and PACPs (i.e., UAPs) are produced in the test sample Q-PCR reaction, then it may be concluded that the test sample was cross-contaminated with the PAC plasmid and the TAP result may be a false positive.

In a specific embodiment—in which the primers and probes comprise (1) a rodent parvovirus specific forward oligonucleotide primer comprising the sequence of SEQ ID NO:1, (2) a rodent parvovirus specific oligonucleotide detection probe comprising the sequence of SEQ ID NO:2, a VIC fluorophore, and an MGBNFQ quencher, (3) an artificial oligonucleotide detection probe, such as the USP comprising the sequence of SEQ ID NO:3 and labeled with 6-FAM and BHQ®-1, (4) a rodent parvovirus specific reverse oligonucleotide primer comprising the sequence of SEQ ID NO:4, (5) an M13 specific forward oligonucleotide primer comprising the sequence of SEQ ID NO:5, (6) an M13 specific oligonucleotide detection probe comprising the sequence of SEQ ID NO:6 and labeled with Cy5 and BHQ®-2, and (7) an M13 specific reverse oligonucleotide primer comprising the sequence of SEQ ID NO:7—the production of TAP is monitored at about 533 nm to about 580 nm, the production of PACP is monitored at about 465 nm to about 510 nm, and the production of NECP is monitored at about 618 nm to about 660 nm.

In one embodiment, the test sample is taken from a production CHO cell culture, e.g., a production culture of EESYR® cells transformed with nucleic acids encoding a protein-of-interest, 96 to 72 hours before the time of harvesting the culture. If a TAP and an NECP is detected in the test sample, but no PACP is detected in the test sample, then a confirmation test may be performed on a second test sample obtained from the same production cell culture 48 hours before the time of harvest. If a TAP and an NECP again are detected in the second test sample, but no PACP is detected in the test sample the cell culture is deemed to be contaminated and may not be processed further. Alternatively, a second test may not be performed, yet the cell culture may be deemed to be contaminated and the culture not processed further.

In one embodiment, nucleic acid is extracted from the test sample taken from the production cell culture. Here, one milliliter of the test sample is subjected to cell lysis, proteolysis, and heat denaturation, followed by combining the sample with a nucleic acid extraction control (NEC) sample and then extracting the nucleic acids from the sample. In one embodiment, the nucleic acids are extracted from the test sample (or NEC-spiked test sample) using an automated nucleic acid extraction system, such as a QIAsymphony® instrument (Qiagen, Inc., Valencia, Calif.) (see Lee et al., Comparative evaluation of the QIAGEN QIAsymphony® SP system and bioMérieux NucliSens easyMAG automated extraction platforms in a clinical virology laboratory, 52(4) J. Clin. Virol. 339-43 (2011)).

In one embodiment, the enzyme uracil-N-glycosylase (UNG) is added to the Q-PCR reaction mixture prior to performing the PCR to selectively degrade contaminating amplicons (see Taggart et al., Use of heat labile UNG in an RT-PCR assay for enterovirus detection, 105(1) J. Virol. Methods. 57-65 (2002)). The reaction mixture is incubated at 50° C. for at least 2 minutes, more specifically in some cases for 2 minutes or 5 minutes.

In a specific embodiment, after the optional UNG treatment the reaction mixture is incubated at 95° C. for 2 minutes, followed by eight cycles of (1) denaturation at 95° C. for 10 seconds, followed by (2) annealing and extension for 30 seconds, such that the first annealing temperature is 70° C., then the annealing temperature is decreased by 1° C. at each cycle, such that the eighth annealing is 62° C. After the initial eight cycles, 40 cycles of DNA amplification is performed comprising the steps of (1) denaturation at 95° C. for 10 seconds, followed by (2) annealing and extension at 62° C. for 30 seconds. In a particular embodiment, the temperature change rate from the denaturation temperature to the annealing temperature is about 4.4° C. per second, and from the annealing temperature to the denaturation temperature is about 2.2° C. per second.

In some embodiments, the method of detecting a biological contaminant in a production cell culture medium or product thereof includes performing an external positive amplification control (PAC) assay run separately from the test sample assay, and performing an external negative control assay run separately from the test sample assay and PAC assay. If either the negative control or the positive control fails, then the result obtained from the test sample assay is rejected.

In one embodiment, the external positive control comprises the steps of (1) combining inter alfa and without a test sample (a) a positive amplification control (PAC) plasmid, which in a specific embodiment comprises the sequence of SEQ ID NO:11, (b) a rodent parvovirus specific forward oligonucleotide primer comprising the sequence of SEQ ID NO:1, (c) a rodent parvovirus specific oligonucleotide detection probe comprising the sequence of SEQ ID NO:2 labeled with VIC and MGBNFQ, (d) an artificial oligonucleotide detection probe, such as the USP comprising the sequence of SEQ ID NO:3 labeled with 6-FAM and BHQ®-1, (e) a rodent parvovirus specific reverse oligonucleotide primer comprising the sequence of SEQ ID NO:4, and (f) a DNA polymerase, preferably a thermostable DNA polymerase with 5' exonuclease activity, such as Taq polymerase; (2) subjecting the positive control mixture to positive control polymerase chain reaction (PCR); and (3) monitoring the production of (a) target amplification polynucleotides (TAPs), (b) nucleic acid extraction control amplification polynucleotides (NECPs), and (c) plasmid amplification control polynucleotides (PACPs) during the PCR. The production of TAP is monitored at about 533 nm to about 580 nm, the production of PACPs is monitored at about 465 nm to about 510 nm, and the production of NECP is monitored at about 618 nm to about 660 nm.

The positive amplification control PCR reaction is run identically to the test sample PCR reaction (as described above). If TAPs and PACPs are produced in the positive control reaction, then it can be concluded that the PCR amplification procedure is operating properly. If TAPs are not produced in the positive amplification control reaction, then any negative TAP in the test sample may be discounted as a failed PCR reaction. In one embodiment, the NEC (i.e., e.g., M13K07) is included in the positive amplification control. A properly functioning control should also reveal a positive NECP signal (see Table 1).

In one embodiment, the external negative control comprises the steps of (1) combining inter alfa and without a test sample and without a PAC plasmid (a) a blank, which can be a buffer that mimics the test sample buffer system, or simply water, (b) a rodent parvovirus specific forward oligonucleotide primer comprising the sequence of SEQ ID NO:1, (c) a rodent parvovirus specific oligonucleotide detection probe comprising the sequence of SEQ ID NO:2 labeled with VIC and MGBNFQ, (d) an artificial oligonucleotide detection probe, such as the USP comprising the sequence of SEQ ID NO:3 labeled with 6-FAM and BHQ®-1, (e) a rodent parvovirus specific reverse oligonucleotide primer comprising the sequence of SEQ ID NO:4, and (f) a DNA polymerase, preferably a thermostable DNA polymerase with 5' exonuclease activity, such as Taq polymerase; (2) subjecting the positive control mixture to positive control polymerase chain reaction (PCR); and (3) monitoring the production of (a) target amplification polynucleotides (TAP), (b) nucleic acid extraction control amplification polynucleotides (NECP), and (c) plasmid amplification control polynucleotides (PACP) during the PCR. The production of TAP is monitored at about 533 nm to about 580 nm, and the production of PACP is monitored at about 465 nm to about 510 nm.

The negative control PCR reaction is run identically to the test sample PCR reaction (as described above). If TAPs and PACPs are produced in the negative control reaction, then it can be concluded that the PCR reagents are contaminated with the PAC plasmid. If TAPs, but no PACPs are produced in the negative control reaction, then it can be concluded that the PCR reagents are contaminated with a parvovirus. In both cases, the test sample results are discarded. However, if both TAP and PACP production is negative in the negative control reaction, TAP and PACP production is positive in the positive amplification control, and TAP (and optionally NECP) production is positive, and PACP production is negative in the test sample reaction, then the technician may conclude that the test sample is contaminated (see Table 2 and Table 3).

In other aspects, the invention provides a positive amplification control plasmid (PAC plasmid), and a mixture of positive control reagents including the positive control plasmid. In one embodiment, the PAC plasmid comprises (1) a parvovirus nucleic acid sequence, (2) an M13K07 nucleic acid sequence, and (3) an artificial nucleic acid sequence unique to the plasmid (a.k.a. UAPS or "unique" sequence). In a specific embodiment, the parvovirus nucleic acid sequence comprises the sequences of SEQ ID NO:1, SEQ ID NO:2, and SEQ ID NO:4; the M13K07 nucleic acid sequence comprises the sequences of SEQ ID NO:5, SEQ ID NO:6, and SEQ ID NO:7, and the unique sequence comprises the antisense sequence of SEQ ID NO:3. In a more specific embodiment, the nucleotide sequence of the PAC plasmid consists of the sequence set forth in SEQ ID NO:11.

In some embodiments, the mixture of positive control reagents includes inter alfa the PAC plasmid described above, a rodent parvovirus specific forward oligonucleotide primer, a rodent parvovirus specific oligonucleotide detection probe, an artificial oligonucleotide detection probe (i.e., the USP), a rodent parvovirus specific reverse oligonucleotide primer, an M13 specific forward oligonucleotide primer, an M13 specific oligonucleotide detection probe, and an M13 specific reverse oligonucleotide primer, and a buffer. The mixture optionally contains dNTPs and Taq polymerase.

TABLE 2

Assay Controls and Test Session Status

| Assay Controls | Parvovirus Signal (TAP) | UAP Signal (PACP) | M13K07 Signal (NECP) |
|---|---|---|---|
| NEC | 0 | 0 | + |
| PAC | + | + | + |
| Negative control (buffer or water) | 0 | 0 | 0 |
| Test session status | ☐VALID | | ☐ INVALID |

TABLE 3

Test Session Status

| Sample Description | Parvovirus | UAP Signal | M13K07 | Is test sample suitable? |
|---|---|---|---|---|
| Negative test sample | 0 | 0 | + | Yes |
| False negative test sample | 0 | 0 | 0 | No |
| Positive test sample | + | 0 | + | Yes |
| False positive test sample | + | + | + | Yes |

In a specific embodiment, the rodent parvovirus specific forward oligonucleotide primer comprises the nucleic acid sequence of SEQ ID NO:1, the rodent parvovirus specific oligonucleotide detection probe comprises a VIC fluorophore, a minor groove binding quencher (MGBNFQ), and the nucleic acid sequence of SEQ ID NO:2, the USP comprises a VIC fluorophore, a non-fluorescent quencher BHQ, and the nucleic acid sequence of SEQ ID NO:3, the rodent parvovirus specific reverse oligonucleotide primer comprises the nucleic acid sequence of SEQ ID NO:4, the M13 specific forward oligonucleotide primer comprises the nucleic acid sequence of SEQ ID NO:5, the M13 specific oligonucleotide detection probe comprises a Cy5 fluorophore, a BHQ-2 quencher, and the nucleic acid sequence of SEQ ID NO:6, and the M13 specific reverse oligonucleotide primer comprises the nucleic acid sequence of SEQ ID NO:7.

EXAMPLE 1

Oligonucleotides and Nucleic Acid Reagents

Rodent parvovirus, M13K07, and artificial unique oligonucleotides (Oligos) were obtained from various vendors at various scales and in various formats, which are described in Table 4. All oligos were assigned a three-year expiration date upon receipt from the vendor.

The oligonucleotides were reconstituted in water to a concentration of 100 μM to produce master stocks. The master stocks were further diluted to produce 10× stock solutions prior to setting up the qPCR reactions. Table 5 depicts the 10× and 1× concentrations of the qPCR oligonucleotides (primers and probes).

TABLE 4

Parvovirus, M13, and unique artificial sequence primers and probes

| Type of Oligo | Name | Sequence (5'-3') | Vendor/Scale/Purification/Format |
|---|---|---|---|
| Forward Oligonucleotide Primer | MVM-FWD | 5'/TGC ATA AAA GAG TAA CCT CAC CAG/3' (SEQ ID NO: 1) | IDT/1 μM/HPLC/lyophilized or Lab Ready Life Technologies/80 KpMol/HPLC/dry or liquid |
| Sequence Detection Probe | MVM-MGB1 | 5'/VIC/ACT GGA TGA TGA TGC AGC/MGBNFQ/3' (SEQ ID NO: 2) | Life Technologies/50 K/HPLC/liquid; 100 pmol/μL |
| Sequence Detection Probe | parvovirus Anti Sense Flag | 5'/6-FAM/TGT CGA TGG CGA ATG GCT A/BHQ ®-1/3' (SEQ ID NO: 3) | IDT/1 μM/HPLC/lyophilized or Lab Ready |
| Reverse Oligonucleotide Primer | MVM-REV | 5'/CCA CCT GGT TGA GCC ATC/3' (SEQ ID NO: 4) | IDT/1 μM/HPLC/lyophilized or Lab Ready Life Technologies/80 KpMol/HPLC/dry or liquid |

TABLE 4-continued

Parvovirus, M13, and unique artificial sequence primers and probes

| Type of Oligo | Name | Sequence (5'-3') | Vendor/Scale/Purification/Format |
|---|---|---|---|
| Forward Oligonucleotide Primer | M13-FWD | 5'/AAG CCT CAG CGA CCG AAT AT/3' (SEQ ID NO: 5) | IDT/1 µM/HPLC/lyophilized or Lab Ready |
| Sequence Detection Probe | M13-probe | /5'/CY5/TAT GCG TGG GCG ATG GTT GTT GTC A /BHQ2/3' (SEQ ID NO: 6) | IDT/1 µM/HPLC/lyophilized or Lab Ready |
| Reverse Oligonucleotide Primer | M13-REV | 5'/TCA GCT TGC TTT CGA GGT GAA T/3' (SEQ ID NO: 7) | IDT/1 µM/HPLC/lyophilized or Lab Ready |

TABLE 5

Oligonucleotide Concentrations

| Oligo name | 1X oligo concentration per PCR reaction | 10X concentration | Volume of Oligo Master Stock for 1 mL 10X concentration |
|---|---|---|---|
| MVM-fwd | 0.15 µM | 1.5 µM | 15 µL |
| MVM-MGB1 | 0.15 µM | 1.5 µM | 15 µL |
| parvovirus AntiSense Flag | 0.15 µM | 1.5 µM | 15 µL |
| MVM-rev | 0.15 µM | 1.5 µM | 15 µL |
| M13-Fwd | 0.1 µM | 1.0 µM | 10 µL |
| M13-Probe | 0.1 µM | 1.0 µM | 10 µL |
| M13-Rev | 0.1 µM | 1.0 µM | 10 µL |

EXAMPLE 2

Positive Amplification Control Plasmid

The parvo-M13 positive amplification control (PAC) plasmid was prepared in pUC57-Kan plasmid (GeneWiz, Inc., South Plainfield, N.J.). This PAC plasmid consists of the sequence set forth in SEQ ID NO:11. The parvovirus-M13 PAC plasmid contains $2.1 \times 10^8$ copies/ng calculated using the following formula: [number=(amount*number/mole)/(bp*ng/g*g/mole of bp)]; where amount=ng, number/mole=$6.022 \times 10^{23}$, bp=4372, ng/g=$1 \times 10^9$, and g/mole of bp=650. The concentration of the plasmid was calculated and expressed as ng/µL and diluted serially to a 10× concentration of $10^2$ copies/µL. From the $10^2$ copies/µL dilution, 50 µL aliquots were prepared and stored in 2 mL sterile screw-cap tubes. All aliquots were stored at <minus 60° C.

EXAMPLE 3

Preparation of M13K07 Phage

Ten-fold serial dilutions of M13K07 phage were performed using MEM as a diluent to obtain M13K07 at a titer of 100 pfu/µL. 200 µL aliquots were prepared and stored at ≤minus 60° C. and assigned a three-year expiration date.

EXAMPLE 4

Q-PCR Reaction Reagent Preparation

The Rodent Parvovirus Real-Time PCR Detection assay is a fully automated TaqMan® PCR process consisting of an automated DNA purification using QIAsymphony® (Qiagen) followed by nucleic acid amplification and real-time PCR product detection on the LightCycler® 480 instrument (Roche Diagnostic). Each test article was automatically spiked with the phage M13K07 as an internal control (IC) in order to assess for presence of PCR inhibitors. The rodent parvovirus primer oligonucleotides were designed to hybridize within a highly conserved region of the rodent parvovirus genome (NS-1 region) in order to ensure broad range detection. The assay was run in a duplex (i.e. two targets) format and the rodent parvovirus and the M13K07 primers respectively generated PCR products of approximately 110 and 97 bp. The PCR product was detected in real-time through cleavage of two probes labeled with different reporter dyes: VIC fluorophore for rodent parvovirus and Cy5 fluorophore for M13K07 phage. A positive amplification control (PAC) plasmid was used at a concentration of 100 copies/uL. This plasmid contains a unique (Flag) sequence (USP) differentiating it from the wild type parvovirus using a specific probe labeled with the fluorophore FAM.

Master Mix was assembled in a 2 mL tube according to Table 6 in amounts sufficient for at least three times the number of test articles including the controls. The tubes were stored at 2-8° C. The negative amplification control (NAC) vial was prepared by adding 50 uL of water to a 2 mL tube.

TABLE 6

Reaction Mixtures

| | Reagent Stock Concentration | Reagent Concentration for One Reaction | Reagent Stock Concentration for One Reaction |
|---|---|---|---|
| qPCR 2X Master Mix (TaqMan or VeriQuest) | 2X | 1X | 12.5 µL |
| Parvo-qPCR-Oligo Mix | 10X | 1X | 2.5 µL |
| Mix Volume per each well | | | 15 µL |
| Sample volume per well (extracted DNA) | | | 10 µL |

EXAMPLE 5

Test Sample Preparation

Since all samples have the potential to contain or be contaminated with adventitious agent, aseptic practices were adhered to for all sample pre-processing steps. The following steps were performed in a clean biosafety cabinet. Test articles (samples) were obtained from antibody or trap molecule producing EESYR® cell cultures and frozen or used directly.

1000 µL of PBS was aliquoted into appropriate 2 mL-tubes to serve as negative extraction controls (NEC). When the PCR is used as an end-point to a cell culture step, the positive and negative controls of the cell culture were used as positive extraction control and negative extraction control, respectively.

Each test article was thawed at room temperature. Those samples in 60 mL bags were transferred to 50 mL-Falcon tubes and then aliquoted. 1000 µL of each sample was pipetted into 2 mL-tubes for pre-processing. 400 µL of lysis buffer (ChargeSwitch® Lysis Buffer L13, (Invitrogen, Cat# CS11202 or equivalent, Carlsbad, Calif.) was added into each tube and vortexed for at least 10 seconds. 20 µL of Proteinase K (≥10 mg/mL, ≥800 units/mL in 40% glycerol (v/v) containing 10 mM Tris-HCl, pH 7.5, with 1 mM calcium acetate; SAFC, Cat# P4850-5ML, Sigma Aldrich, St. Louis, Mo.) was then added into each sample and vortexed for at least 10 seconds. Samples were then incubated at 65° C. for 30 minutes. After incubation, the samples were vortexed and centrifuged at 17,000×g for 10 minutes.

Concurrently, the positive amplification control (PAC; minimum 50 uL of $10^2$ copies/µL plasmid in 2 mL tube) and M13K07 ($10^2$ PFU/mL) Internal Control (IC; minimum 150 µL/12 samples) were thawed.

EXAMPLE 6

Nucleic Acid Extraction

Internal Control (IC) was required for the programmed extraction protocol on the QIASymphony® Instrument (Qiagen, Valencia, Calif.). The instrument automatically added 120 µL of reconstituted IC to each sample. For every 12 samples, 1.8 mL of IC (i.e., 1 vial) was required by the instrument. Vials of IC were prepared by adding 1650 µL AVE buffer (RNase-free water containing 0.04% sodium azide) to 150 µL of M13K07 IC.

1000101j Each prepared sample was loaded into the Sample Carrier of the instrument within the biosafety cabinet (BSC). The vial(s) of IC were loaded into a separated (dedicated) Sample Carrier within the BSC at a ratio of one vial of IC per 12 samples. All drawers were closed and the instrument was run according to manufacturer's recommended protocol (see QIAsymphony DNA Handbook, 09/2010, available at http://www.algimed.by/download/EN-QIAsymphony-DNA-Handbool.pdf).

The Reagent Prep Cartridge was prepared with the QIAsymphony® DSP Virus/Pathogen reagent kit, which contained all reagents required for performing an extraction (see QIAsymphony® DSP Virus/Pathogen Kit Instructions for Use (Handbook, April 2013, available at https://www.qiagen.com/us/resources/download.aspx?id=f8bc0b3c-0aff-46ee-8807-5ed145f9e969&lang=en). The reagent prep cartridge contained proteinase K and had a shelf-life of about two weeks.

The nucleic acid extraction was performed in a 96-well format reaction plate to facilitate integration with the Q-PCR. After the automated nucleic acid extraction procedure was completed and passed the status check, the reaction plate was cooled and sealed with LightCycler® 480 Sealing Foil (Roche, Branchburg, N.J.). The 96-well plate was placed in a plate spinner balanced with a suitable counterweight (e.g., another 96-well plate) and spun for 30 to 60 seconds. The wells were checked for bubbles and the spin was repeated if necessary.

EXAMPLE 7

Q-PCR

Q-PCR was performed on the LightCycler® 480 Instrument (Roche, Branchburg, N.J.) using any one of two programs—TaqMan Triplex, and/or Veriquest Triplex. The TaqMan Triplex protocol used the TaqMan Fast Advance Custom Master Mix without the reference dye (ROX). Three fluorescence channels (FAM, VIC, and CY5) were selected and a UNG step time of 2 minutes. The reaction parameters that were used are outlined in Table 7.

When using VeriQuest® Master Mix, also without ROX, a UNG step time of 5 minutes was used. The reaction parameters that were used are outlined in Table 8.

TABLE 7

Rodent Parvovirus PCR TaqMan Triplex Program Steps

| Step Name | # of Cycles | Analysis mode | Temperature (° C.) | Time | Block ramp rate (° C./Sec) | Step Size |
|---|---|---|---|---|---|---|
| UNG | 1 | None | 50 | 2 min | 4.4 | |
| Pre-Incubation | 1 | None | 95 | 2 min | 4.4 | |
| TD | 8 | None | 95 | 10 sec | 4.4 | 1° C./step |
| | | | 70 --> 62 | 30 sec | 2.2 | |
| Amplification | 40 | Quantification | 95 | 10 sec | 4.4 | |
| | | | 62 | 30 sec | 2.2 | |
| Cooling | 1 | None | 40 | 30 sec | 2.2 | |

The crossing point (Cp) fluorescence signal for each of the M13 internal control, rodent parvovirus, and positive amplification control plasmid was determined by one or both of two algorithms. The first algorithm is the Automated Second Derivative method. This method does not require user input and generally resulted in greater consistency, and therefore was considered to be the preferred method. The second algorithm is the Fit Points method. This method allows the user to set the threshold line, in cases of divergent background. The point where the log-linear curve crosses that threshold line becomes the crossing point. The following filter combs were used to monitor fluorescent signals: 533-580 nm (VIC signal) for Rodent parvovirus (subset "Sample-Parvo"); 618-660 nm (Cy5 signal) for the internal control M13K07 (subset "Sample-M13"); and 465-510 nm (FAM signal) for the positive amplification control plasmid (subset "Sample-FAM"). The fluorescence background level was determined using the Fit Point analysis in case of ambiguous fluorescence signal. Acceptable background fluorescence signal was considered to be ≤1 unit on the amplification plot scale. Any fluorescence signal ≤1 unit was considered within acceptable background, and thus negative.

TABLE 8

Rodent Parvovirus PCR VeriQuest Triplex Program Steps

| Step Name | # of Cycles | Analysis mode | Temperature (° C.) | Time | Block ramp rate (° C./Sec) | Step Size |
|---|---|---|---|---|---|---|
| UNG | 1 | None | 50 | 5 min | 4.4 | |
| Pre-Incubation | 1 | None | 95 | 2 min | 4.4 | |
| TD | 8 | None | 95 | 10 sec | 4.4 | 1° C./step |
| | | | 70 --> 62 | 30 sec | 2.2 | |
| Amplification | 40 | Quantification | 95 | 10 sec | 4.4 | |
| | | | 62 | 30 sec | 2.2 | |
| Cooling | 1 | None | 40 | 30 sec | 2.2 | |

EXAMPLE 8

Conditions for a Valid Test Session

For the test session to be considered valid, the following conditions must be met. The Negative Amplification Control (NAC, i.e. water) must be negative for fluorescence signal in all three channels. The Negative Extraction Control (NEC, i.e. PBS) or the cell Culture Negative Control flask must be negative for fluorescence signal in the [533-580] channel (i.e. rodent parvovirus probe VIC signal), negative for fluorescence signal in the [465-510] channel (i.e. positive amplification control [PAC] Antisense Flag probe-FAM signal), and positive for fluorescence signal in the [618-660] channel (i.e. M13K07 probe-CY5 signal). The PAC should be positive for fluorescence signals all three channels. The M13K07 Cp value in the NEC was used as a reference for assessing the presence of inhibitory substance in the samples.

If the PCR was used as an end-point for a test article from a cell culture step with a rodent parvovirus positive control, the Positive Virus Control must be positive for fluorescence signal in the [533-580] channel (i.e. rodent parvovirus probe VIC signal), positive for fluorescence signal in the [618-660] channel (i.e., M13K07 probe-CY5 signal), and negative for fluorescence signal in the [465-510] channel (i.e., PAC Antisense Flag probe-FAM signal). The M13K07 Cp value in the cell culture positive control sample was expected to be within ±4 cycles range of the NEC-M13 Cp value.

For all PAC plasmid-containing control reactions, the fluorescent signals must be positive in all three channels.

EXAMPLE 9

Conditions for an Invalid Test Session

An assay was considered invalid when any one or more of the following conditions was met: (1) a very low amplification curve (<1 unit on the fluorescence scale) for the PAC, (2) a determinant error (machine, software, or human error) was confirmed, (3) the NAC was positive for amplification in any of the three channels, (4) the NEC was positive for amplification in the [533-580] VIC channel, positive for amplification in the [465-510] FAM channel, or negative for amplification in the [618-660] Cy5 channel, and (5) the PAC was negative for amplification signal in any of the three channels. Investigation and retesting of the test sample was performed whenever the assay was determined to be invalid.

EXAMPLE 10

Conditions for Negative Sample Result in Valid Test

All of the following conditions must be met for a valid negative parvovirus test result. The sample must be positive for M13K07 DNA amplification signal in the M13 [618-660] channel within an expected Cp value range of NEC-M13 Cp ±4 cycles, suggesting the absence of PCR inhibitors. The sample must be negative for parvovirus DNA amplification signal in the parvovirus [533-580] channel. A fluorescence signal below 1 unit on the fluorescence scale, regardless the Cp value was considered within the acceptable fluorescence background level, and was reported as negative for parvovirus DNA amplification. The sample must be negative for PAC amplification signal in the Antisense Flag [465-510] channel. Note that a fluorescence signal below 1 unit on the fluorescence scale, regardless the Cp value (automatically generated by the instrument), was considered within the acceptable fluorescence background level, and was reported as negative for PAC-plasmid DNA amplification.

EXAMPLE 11

Conditions for "No Sample" Result in a Valid Test Session

A "No Sample" result occurred when any one or more of the following conditions was met. Whenever the sample was negative for M13K07 DNA amplification signal in the Cy5 channel [618-660], negative for parvovirus DNA amplification signal in the parvovirus channel [533-580], and negative for PAC amplification in the antisense Flag FAM channel [465-510], the sample or PCR reagents were investigated per standard operating procedure. This condition suggests the presence of PCR inhibitors or a failure of proper nucleic acid extraction. Samples could be diluted (1:2, 1:5, 1:10) to overcome inhibition. A Cp value for the fluorescence signal in the M13 channel [618 660] that was out of range (NEC M13 Cp ±4 cycles), indicated partial inhibition of the PCR or error in phage spiking and warranted a repeat test. Sample dilution (1:2, 1:5, 1:10) could be considered to overcome any inhibition of PCR. Any evidence of determinant error or unexpected very low fluorescence signal (<1 unit on the fluorescence scale) observed in the M13 channel [618-660] that did not allow a conclusive evaluation of the sample suitability was considered to be a "no sample result", and suggested failure during amplification or DNA extraction. This warranted a repeat test.

EXAMPLE 12

Condition for Initial Out of Specification (iOOS) Sample Result in a Valid Test Session A sample was considered to be iOOS when it was (i) positive for parvovirus DNA amplification signal in the parvovirus channel [533-580] (i.e., rodent parvovirus probe VIC signal) with a fluorescence signal above 1 unit on the fluorescence scale (for at least one of the two replicate wells), and (ii) negative for PAC amplification in the antisense Flag FAM channel [465-510], indicating that there was no cross-contamination from the PAC. As a result, the technician must (i) initiate a GLIF (General Laboratory Investigation Form), (ii) notify the department that submitted the sample to QC Virology for testing, (iii) initiated an NOE, (iv) preserve the amplification tube (freeze at −20° C.) for further investigation (e.g. Flag sequence screening or sequencing), and (v) repeat the assay and retest the sample.

EXAMPLE 13

Repeat and Retest Plan

A repeat test was initiated whenever the assay was invalid or a sample result was considered a "no result." A retest was performed for confirmation of an iOOS event (i.e. the first time a sample result was positive for DNA amplification signal in the parvovirus channel [533-580]). Retests or repeat tests must be executed using fresh reagent aliquots (i.e., master mix reagents, extraction kit).

If NAC was positive for fluorescence in any channel; the entire test session would be repeated starting from the amplification (PCR) step using the already purified DNA samples with freshly made master mix. If NEC was negative for fluorescence in the M13 channel [618-660], the entire test session would be repeated starting from the DNA extraction step. If NEC was positive for fluorescence in the parvovirus channel [533-580] or the Antisense Flag channel [465-510], the entire test session would be repeated starting from the DNA extraction step. If PAC was negative for fluorescence in any channel, the test session would be repeated from the amplification (PCR step), using the same purified DNA samples with freshly made master mix For those samples with a "no sample" result, the test session would be repeated for the impacted sample starting from the DNA extraction step. Samples could be diluted (1:2, 1:5, or 1:10) (in addition to the non-diluted sample) before DNA extraction as part of the investigation and issue resolution process in order to demonstrate the presence of inhibitors.

The retest to confirm an initial positive result (iOOS) was performed using four separate aliquots as follows: two aliquots of test article from the original sampling event (e.g., one day after final feed), and two aliquots of test article from a different sampling event (e.g., two days after final feed, if possible) or different sample bag. If any of the additional testing of the 4 aliquots resulted in a positive signal with no evidence of determinate error (demonstrated via the investigation), the lot was considered as failing the requirement of absence of rodent parvovirus virus genomic material. An infectivity assay was warranted for final disposition for such a positive Q-PCR result. CHO-K1 cells are used as the indicator cell line to determine the infection state of the detected nucleic acid.

Whenever the retest results are negative, a confirmatory test is required at a different sampling event (e.g., three days after final feed) to confirm absence of rodent parvovirus genomic material.

EXAMPLE 14

Retest Plan for Other Sample Types with iOOS

Other sample types including, e.g., unprocessed bulk material, end-of-production cells, cells at the limit of in vitro age, and soy material, which had an initial positive result (iOOS), were retested as follows using four separate aliquots:

Two aliquots of test article from the original sample container (i.e., e.g., bag) and two aliquots from a different sample container were retested according to standard operating procedures. The CHO-K1 indicator cell was inoculated with one sample aliquot of the test article from the original sample container. The inoculated indicator cell CHO-K1 was harvested after 1-3 days in culture per standard operating procedure to determine the infectious status of the detected nucleic acid. A standard curve for quantification of the re-extracted nucleic acid may be used.

Whenever any of the additional PCR testing of the four aliquots was positive with no evidence of determinate error (demonstrated via the investigation), the infectivity assay determines the final disposition of the article. Upon confirmation of the initial OOS, sequencing of the nucleic acid and transmission electron microscopy (TEM) could be considered in order to identify the microorganism and rule out any laboratory error.

The infectivity assay using CHO-K1 as an indicator cell for the suspected contaminated material is required to determine the infectious state of the nucleic acid detected. Whenever the investigation fails to support the possibility of parvovirus virus contamination and the additional PCR tests of the four aliquots of test article and the CHOK1 culture are all negative, the lot was considered as meeting the requirements for absence of infectious rodent parvovirus virus.

EXAMPLE 15

Parvovirus Testing During Recombinant Protein Production

The Q-PCR procedure described above was performed as a critical in-process control for the testing of cell culture fluid, i.e., the unprocessed bulk material from the production bioreactor containing a CHO cell derivative containing heterologous antibody heavy chain and light chain constructs. Each heterologous monoclonal antibody (mAb) binds to a different target or epitope. Good manufacturing process (GMP) tests were performed by QC virology scientists at a large-scale bioprocess production facility. Sixteen (16) of those tests are listed in Table 9. In each case, the test sessions were valid, the assay system suitability criteria had been met, and false positive detection was not observed. In test sessions #13 and #14, false negative detection did occur, which suggested the presence of PCR inhibitors or a failure of nucleic acid extraction.

TABLE 9

Rodent Parvovirus PCR Tests

| Test # | Type of Sample | Product | Lot Testing |
|---|---|---|---|
| 1 | UPB EA | mAb1 | '51 Rodent Parvo PCR |
| 2 | UPB | mAb1 | '52 Rodent Parvo PCR |
| 3 | UPB | mAb3 | '07 Rodent Parvo PCR |
| 4 | UPB | mAb1 | '51 Rodent Parvo PCR |
| 5 | UPB EA | mAb2 | '35 Rodent Parvo PCR |
| 6 | UPB EA | mAb4 | '05 Rodent Parvo PCR |
| 7 | UPB | mAb2 | '36 Rodent Parvo PCR |
| 8 | UPB | mAb1 | '53 Rodent Parvo PCR |
| 9 | UPB | mAb1 | '53 Rodent Parvo PCR |
| 10 | UPB EA | mAb3 | '08 Rodent Parvo PCR |
| 11 | UPB EA | mAb5 | '01 Rodent Parvo PCR |
| 12 | UPB EA | mAb1 | '54 Rodent Parvo PCR |
| 13 | UPB | mAb6 | '01 Rodent Parvo PCR |
| 14 | UPB | mAb4 | '05 Rodent Parvo PCR Qualification |
| 15 | UPB | mAb2 | '35 Rodent Parvo PCR Qualification |
| 16 | UPB | mAb2 | '36 Rodent Parvo PCR Qualification |

UPB = Unprocessed Bulk Material; EA = Early Alert; Rodent Parvo PCR = Q-PCR Procedure described above.

The invention claimed is:

1. A positive amplification control (PAC) plasmid comprising:
   a unique artificial plasmid-specific sequence (UAPS), wherein said UAPS comprises SEQ ID NO: 10;
   a target amplification polynucleotide (TAP) sequence, wherein said TAP comprises all or part of a parvovirus NS-1 sequence, and
   a nucleic acid extraction control (NEC) nucleotide sequence, wherein said NEC comprises an M13 bacteriophage nucleotide sequence.

2. The PAC plasmid of claim 1, wherein the parvovirus NS-1 sequence comprises SEQ ID NO: 9 or any one of SEQ ID NOs: 12-37.

3. The PAC plasmid of claim 1, wherein the parvovirus NS-1 sequence comprises SEQ ID NO: 37.

4. The PAC plasmid of claim 1, wherein said M13 bacteriophage nucleotide sequence is a M13K07 nucleotide sequence.

5. The PAC plasmid of claim 4, wherein said M13K07 nucleotide sequence comprises SEQ ID NO. 8.

6. The PAC plasmid of claim 1, further comprising binding sites that hybridize to one or more oligonucleotide primers.

7. The PAC plasmid of claim 6, wherein said one or more oligonucleotide primers is selected from the group consisting of a forward oligonucleotide primer, a reverse oligonucleotide primer, and a combination thereof.

8. The PAC plasmid of claim 6, wherein said one or more oligonucleotide primers are rodent parvovirus oligonucleotide primers.

9. The PAC plasmid of claim 8, wherein said rodent parvovirus oligonucleotide primers are selected from the group consisting of a forward oligonucleotide primer, a reverse oligonucleotide primer, and a combination thereof.

10. The PAC plasmid of claim 1, further comprising binding sites that hybridize to M13 oligonucleotide primers.

11. The PAC plasmid of claim 10, wherein said M13 oligonucleotide primers are selected from the group consisting of a forward oligonucleotide primer, a reverse oligonucleotide primer, and a combination thereof.

12. The PAC plasmid of claim 1, wherein said NS-1 sequence is selected from the group consisting of minute virus of mice prototype strain (MVMp), minute virus of mouse immunosuppressive strain (MVMi), minute virus of mouse Cutter strain (MVMc); mouse parvovirus 1b (MPV-1b), mouse parvovirus 1a (MPV-1a), mouse parvovirus 1c (MPV-1c), hamster parvovirus (HaPV), Toolan's parvovirus (H-1), Kilham rat virus (KRV), rat parvovirus 1a, rat minute virus, and Umass strain of Rat virus L (RV-Umass).

13. The PAC plasmid of claim 1, wherein
   the unique artificial plasmid-specific sequence (UAPS) comprises SEQ ID NO: 10;
   the parvovirus nucleic acid sequence comprises SEQ ID NO: 37; and
   the M13 bacteriophage nucleotide sequence comprises SEQ ID NO: 8.

14. The PAC plasmid of claim 1, wherein the plasmid sequence comprises SEQ ID NO: 11.

* * * * *

SEQUENCE LISTING

<160> NUMBER OF SEQ ID NOS: 37

<210> SEQ ID NO 1
<211> LENGTH: 24
<212> TYPE: DNA
<213> ORGANISM: Parvovirus

<400> SEQUENCE: 1
tgcataaaag agtaacctca ccag              24

<210> SEQ ID NO 2
<211> LENGTH: 18
<212> TYPE: DNA
<213> ORGANISM: Parvovirus

<400> SEQUENCE: 2
actggatgat gatgcagc                     18

<210> SEQ ID NO 3
<211> LENGTH: 19
<212> TYPE: DNA
<213> ORGANISM: Parvovirus

<400> SEQUENCE: 3
tgtcgatggc gaatggcta                    19

<210> SEQ ID NO 4
<211> LENGTH: 18
<212> TYPE: DNA
<213> ORGANISM: Parvovirus

<400> SEQUENCE: 4
ccacctggtt gagccatc                     18

<210> SEQ ID NO 5
<211> LENGTH: 20
<212> TYPE: DNA
<213> ORGANISM: Bacteriophage M13

<400> SEQUENCE: 5
aagcctcagc gaccgaatat                   20

```
<210> SEQ ID NO 6
<211> LENGTH: 24
<212> TYPE: DNA
<213> ORGANISM: Bacteriophage M13

<400> SEQUENCE: 6
tatgcgtggg cgatggttgt tgtc                                          24

<210> SEQ ID NO 7
<211> LENGTH: 22
<212> TYPE: DNA
<213> ORGANISM: Bacteriophage M13

<400> SEQUENCE: 7
tcagcttgct ttcgaggtga at                                            22

<210> SEQ ID NO 8
<211> LENGTH: 6407
<212> TYPE: DNA
<213> ORGANISM: Bacteriophage M13

<400> SEQUENCE: 8
aacgctacta ctattagtag aattgatgcc accttttcag ctcgcgcccc aaatgaaaat     60
atagctaaac aggttattga ccatttgcga aatgtatcta atggtcaaac taaatctact    120
cgttcgcaga attgggaatc aactgttaca tggaatgaaa cttccagaca ccgtacttta    180
gttgcatatt taaaacatgt tgagctacag caccagattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttttcg cctctttcgt tttaggttgg tgccttcgta   1260
gtggcattac gtatttttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactcccc tgcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
```

```
tttttggaga ttttcaacat gaaaaaatta ttattcgcaa ttcctttagt tgttcctttc   1620
tattctcact ccgctgaaac tgttgaaagt tgtttagcaa accccatac agaaaattca    1680 tttactaacg tctggaaaga cgacaaaact ttagatcgtt acgctaacta tgagggttgt   1740
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg acccgttaa aacttattac cagtacactc ctgtatcatc aaaagccatg    2160
tatgacgctt actggaacgg taaattcaga gactgcgctt tccattctgg ctttaatgag   2220
gatccattcg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataagggg ctatgaccga aaatgccgat    2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtcttta gcgctggtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttacttttc   2940
ttaaaaaggg cttcggtaag atagctattg ctatttcatt gtttcttgct cttattattg   3000
ggcttaactc aattcttgtg ggttatctct ctgatattag cgctcaatta ccctctgact   3060
ttgttcaggg tgttcagtta attctcccgt ctaatgcgct tccctgtttt tatgttattc   3120
tctctgtaaa ggctgctatt ttcattttg acgttaaaca aaaaatcgtt tcttatttgg    3180
attgggataa ataatatggc tgtttatttt gtaactggca aattaggctc tggaaagacg   3240
ctcgttagcg ttggtaagat tcaggataaa attgtagctg ggtgcaaaat agcaactaat   3300
cttgatttaa ggcttcaaaa cctcccgcaa gtcgggaggt tcgctaaaac gcctcgcgtt   3360
cttagaatac cggataagcc ttctatatct gatttgcttg ctattgggcg cggtaatgat   3420
tcctacgatg aaaataaaaa cggcttgctt gttctcgatg agtgcggtac ttggtttaat   3480
acccgttctt ggaatgataa ggaaagacag ccgattattg attggtttct acatgctcgt   3540
aaattaggat gggatattat ttttcttgtt caggacttat ctattgttga taaacaggcg   3600
cgttctgcat tagctgaaca tgttgtttat tgtcgtcgtc tggacagaat tactttacct   3660
tttgtcggta cttatattc tcttattact ggctcgaaaa tgcctctgcc taaattacat    3720
gttggcgttg ttaaatatgg cgattctcaa ttaagcccta ctgttgagcg ttggctttat   3780
actggtaaga atttgtataa cgcatatgat actaaacagg ctttttctag taattatgat   3840
tccggtgttt attcttattt aacgccttat ttatcacacg gtcggtattt caaaccatta   3900
```

```
aatttaggtc agaagatgaa attaactaaa atatatttga aaaagttttc tcgcgttctt    3960
tgtcttgcga ttggatttgc atcagcattt acatatagtt atataaccca acctaagccg    4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttctttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gctaataatt ttgatatggt tggttcaatt ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atctattgac ggctctaatc tattagttgt    4740
tagtgcacct aaagatattt tagataacct tcctcaattc ctttctactg ttgatttgcc    4800
aactgaccag atattgattg agggtttgat atttgaggtt cagcaaggtg atgctttaga    4860
tttttcattt gctgctggct ctcagcgtgg cactgttgca ggcggtgtta atactgaccg    4920
cctcacctct gttttatctt ctgctggtgg ttcgttcggt atttttaatg gcgatgtttt    4980
agggctatca gttcgcgcat taagactaa tagccattca aaatattgt ctgtgccacg    5040 tattcttacg ctttcaggtc agaagggttc tatctgtgtt ggccagaatg tccctttat    5100 tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctcttttact    5340
cggtggcctc actgattata aaacacttc tcaagattct ggcgtaccgt tcctgtctaa    5400
aatcccttta atcggcctcc tgtttagctc ccgctctgat tccaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
gggggctccc tttagggttc cgatttagtg ctttacggca cctcgacccc aaaaaacttg    5700
atttgggtga tggttcacgt agtgggccat cgccctgata dacggttttt cgccctttga    5760
cgttggagtc cacgttcttt aatagtggac tcttgttcca aactggaaca cactcaacc    5820 ctatctcggg ctattctttt gatttataag ggattttgcc gatttcggcc tattggttaa    5880
aaaatgagct gatttaacaa aaatttaacg cgaattttaa caaatatatta acgtttacaa    5940 tttaaatatt tgcttataca atcttcctgt ttttgggget tttctgatta tcaaccgggg    6000
tacatatgat tgacatgcta gttttacgat taccgttcat cgattctctt gtttgctcca    6060
gactctcagg caatgacctg atagcctttg tagacctctc aaaaatagct accctctccg    6120
gcatgaattt atcagctaga acggttgaat atcatattga tggtgatttg actgtctccg    6180
gcctttctca ccctttgaa tctttaccta cacattactc aggcattgca tttaaaatat    6240
atgagggttc taaaaatttt tatccttgcg ttgaaataaa ggcttctccc gcaaaagtat    6300
```

```
tacagggtca taatgttttt ggtacaaccg atttagcttt atgctctgag gctttattgc    6360
ttaattttgc taattctttg ccttgcctgt atgatttatt ggatgtt                  6407

<210> SEQ ID NO 9
<211> LENGTH: 2019
<212> TYPE: DNA
<213> ORGANISM: Minute virus of mouse

<400> SEQUENCE: 9
atggctggaa atgcttactc tgatgaagtt ttgggagcaa ccaactggtt aaaggaaaaa      60
agtaaccagg aagtgttctc atttgttttt aaaaatgaaa atgttcaact gaatggaaaa     120
gatatcggat ggaatagtta caaaaaagag ctgcaggagg acgagctgaa atctttacaa     180
cgaggagcgg aaactacttg ggaccaaagc gaggacatgg aatgggaaac cacagtggat     240
gaaatgacca aaaagcaagt attcattttt gattctttgg ttaaaaaatg tttatttgaa     300
gtgcttaaca caaagaatat atttcctggt gatgttaatt ggtttgtgca acatgaatgg     360
ggaaaagacc aaggctggca ctgccatgta ctaattggag gaaaggactt tagtcaagct     420
caagggaaat ggtggagaag gcaactaaat gtttactgga gcagatggtt ggtaacagcc     480
tgtaatgtgc aactaacacc agctgaaaga attaaactaa gagaaatagc agaagacaat     540
gagtgggtta ctctacttac ttataagcat aagcaaacca aaaagactaa taccaagtgt     600
gttctttttg gaaacatgat tgcttactat tttttaacta aaaagaaaat aagcactagt     660
ccaccaagag acggaggcta ttttcttagc agtgactctg gctggaaaac taactttttta    720 aaagaaggcg agcgccatct agtgagcaaa ctatacactg atgacatgcg gccagaaacg     780
gttgaaacca cagtaaccac tgcgcaggaa actaagcgcg gcagaattca aactaaaaaa     840
gaagtttcta ttaaaactac acttaaagag ctggtgcata aagagtaac ctcaccagag      900 gactggatga tgatgcagcc agacagttac attgaaatga tggctcaacc aggtggagaa     960
aacctgctga aaaatacgct agagatttgt acactaactc tagccagaac caaaacagca    1020
tttgacttaa ttttagaaaa agctgaaacc agcaaactaa ccaacttttc actgcctgac    1080
acaagaacct gcagaatttt tgcttttcat ggctggaact atgttaaagt ttgccatgct    1140
atttgctgtg ttttaaacag acaaggaggc aaaagaaata ctgttttatt tcatggacca    1200
gccagcacag gcaaatctat tattgcacaa gccatagcac aagcagttgg caatgttggt    1260
tgctataatg cagccaatgt aaactttcca tttaatgact gtaccaacaa gaacttgatt    1320
tgggtagaag aagctggtaa ctttggacag caagtaaacc agtttaaagc catttgctct    1380
ggtcaaacta ttcgcattga tcaaaaagga aaaggcagca acagattga accaacacca     1440 gtcatcatga ccacaaatga gaacattaca gtggtcagaa taggctgcga agaaagacca    1500
gaacacactc aaccaatcag agacagaatg cttaacattc atctaacaca taccttgcct    1560
ggtgactttg gtttggttga caaaaatgaa tggcccatga tttgtgcttg gttggtaaag    1620
aatggttacc aatctaccat ggcaagctac tgtgctaaat ggggcaaagt tcctgattgg    1680
tcagaaaact gggcggagcc aaaggtgcca actcctataa atttactagg ttcggcacgc    1740
tcaccattca cgacaccgaa aagtacgcct ctcagccaga actatgcact aactccactt    1800
gcatcggatc tcgaggacct ggctttagag ccttggagca caccaaatac tcctgttgcg    1860
ggcactgcag aaacccagaa cactgggaa gctggttcca aagcctgcca agatggtcaa     1920
ctgagcccaa cttggtcaga gatcgaggag gatttgagag cgtgcttcgg tgcggaaccg    1980
```
ttgaagaaag acttcagcga gccgctgaac ttggactaa                           2019

<210> SEQ ID NO 10
<211> LENGTH: 19
<212> TYPE: DNA
<213> ORGANISM: Artificial
<220> FEATURE:
<223> OTHER INFORMATION: synthetic

<400> SEQUENCE: 10
tagccattcg ccatcgaca                                                  19

<210> SEQ ID NO 11
<211> LENGTH: 1707
<212> TYPE: DNA
<213> ORGANISM: Artificial
<220> FEATURE:
<223> OTHER INFORMATION: synthetic

<400> SEQUENCE: 11
aagcctcagc gaccgaatat atcggttatg cgtgggcgat ggttgttgtc attgtcggcg     60
caactatcgg tatcaagctg tttaagaaat tcacctcgaa agcaagctga cacgcctacc    120
gcgatgctga atgacccgga ctagagtggc gaaatttatg gcgtgtgacc cgttatgctc    180
catttcggtc agtgggtcat tgctagtagt cgattgcatt gccattctcc gagtgattta    240
gcgtgacagc cgcagggaac ccataaaatg caatcgtagt ccacctgatc gtacttagaa    300
atgagggtcc ccttttgccc acgcacctgt tcgctcgtcg tttgctttta agaaccgcac    360
gaaccacaga gcataaagag aacctctagc tcctttacaa ggtactggtt ccctttccag    420
cgggatgcct tatctaaacg caatgacaga cgtattcctc aggccacatc gcttcctact    480
tccgctggga tccatcattg gcggccgaag ccgccattcc atagtgagtc cttcgtctgt    540
gtctttctgt gccagatcgt ctagcaaatt gccgatccag tttatctcac gaaactatag    600
tcgtacagac cgaaatctta agtcaaatca cgcgactagg ctcagctcta ttttagtggt    660
catgggtttt ggtccgcccg agcggtgcaa ccgattagga ccatgtaaaa catttgttac    720
aagtcttctt ttaaacacaa tcttcctgct cagtggcgca tgattatcgt tgttgctagc    780
cagcgtggta agtaacagca ccactgcgag cctaatgtgc cctttccacg aacacagggc    840
tgtccgatcc tatattagga ctccgcaatg gggttagcaa gtcgcaccct aaacgatgtt    900
gaagactcgc gatgtacatg ctctggtaca atacatacgt gttccggctg ttatcctgca    960
tcggaacctc aatcatgcat cgcaccagcg tattcgtgtc atctaggagg ggcgcgtagg   1020
ataaataatt caattaagat gtcgttatgc tagtatacgc ctaccgtca ccggccatct    1080 gtgtgcagat ggggcgacga gttactggcc ctgatttctc cgcttctaat accacacact   1140
gggcaatacg agctcaagcc agtctcgcag taacgctcat cagctaacga aagagttaga   1200
ggctcgctaa cggagacgag ttaaagacac gagttcccaa aaccaggcgg gctcgccacg   1260
acggctaatc ctggtagttt acgtgaacaa tgttctgaag aaaatttgtg aaagaaggac   1320
ccgtcaccgc ctacaattac ctacaacggt cggccgcacc ttcgattgtc gtggccaccc   1380
tcggattaca cggcagaggt ggttgtgtcc cgacaggcca gcatattatc ctgaggcgtt   1440
accccaatcg ttctccgtcg gatttgctac agccctgag cgctacatgc acgaaaccaa    1500
gttatgtatg cactgggccg tcaataggac gtagccttgt agttagcacg tagcccggcc   1560
gcattagtac agtagagcct ccgccggcat cctgtttatt aagttatttc tgcataaaag   1620
agtaacctca ccagaggact ggatgatgat gcagccagac agttagccat cgccatcga    1680 cattgaaatg atggctcaac caggtgg         1707

<210> SEQ ID NO 12
<211> LENGTH: 2019
<212> TYPE: DNA
<213> ORGANISM: Mouse parvovirus minute virus
<220> FEATURE:
<223> OTHER INFORMATION: lymphotropic variant sequence

<400> SEQUENCE: 12

| | |
|---|---|
| atggctggaa atgcttactc tgatgaagtt ttgggaacaa ccaactggtt aaaggaaaaa | 60 |
| agtaaccagg aagtgttctc atttgttttt aaaactgagg atgttcaact aaatggaaaa | 120 |
| gatatcggat ggaataatta caaaaaggag ctgcaggagg acgagctgaa atctttacaa | 180 |
| cgaggagcgg aaactacctg ggaccaaagc gaggacatgg aatgggaatc tacagtggat | 240 |
| gaaatgacca aaaagcaagt attcatttat gactctttag ttaaaaaatg tttgtttgaa | 300 |
| gtgcttagca caaaaatat agctcctgct gatgttactt ggtttgtgca gcatgaatgg | 360 |
| gggaaagacc aaggctggca ctgccatgta ctaattggag gcaaggactt tagtcaagct | 420 |
| caaggaaaat ggtggagaag gcagctaaat gtttactgga gcagatggtt ggtaacagcc | 480 |
| tgtaatgtgc agctaacacc agctgaaaga attaaactaa gagaaatagc agaagacagt | 540 |
| gagtgggtta ctttactcac ttataaacat aagcaaacca aaaaggacta tactaaatgt | 600 |
| gttcttttg gaaatatgat tgcttactac tttttaacca aaagaaaat aagcaccagt | 660 |
| ccgccaaggg acggaggcta ttttctaagc agtgactctg gctggaaaac taactttta | 720 |
| aaagagggcg aacgccatct agtgagcaaa ttatacactg atgacatgcg gccagaaacg | 780 |
| gttgaaacca cagtaaccac tgcgcaggaa actaagcgcg gcagaattca aactaaaaaa | 840 |
| gaggtttcta ttaaaaccac acttaaagag ctagtgcata aagagtaac ctcaccagaa | 900 |
| gactggatga tgatgcagcc agacagttac attgaaatga tggctcaacc aggtggagaa | 960 |
| aacctgctga aaaatacgct agagatttgt acgctaactc tagccagaac aaaaacagca | 1020 |
| tttgacttga ttttagaaaa agctgaaacc agcaaactaa ccaactttc actgcctgac | 1080 |
| acaagaacct gcaagatttt tgcttttcat ggctggaact atgttaaagt ttgccatgct | 1140 |
| atttgctgtg ttctaaacag acaaggaggc aaaagaaata ctgttttatt tcacggacca | 1200 |
| gccagtacag gcaaatctat tattgcacaa gccatagcac aggcagttgg taatgttggt | 1260 |
| tgctataatg cagctaatgt gaactttcca tttaatgact gtaccaacaa gaacttgatt | 1320 |
| tgggtagaag aagctggtaa cttggacag caagtaaacc agtttaaagc catttgctct | 1380 |
| ggtcaaacta ttcgcattga tcaaaaagga aaggcagca acaaattga ccaacacca | 1440 |
| gtcatcatga ccacaaatga aacattaca gtggtcagaa taggctgcga agagagacca | 1500 |
| gaacacactc aaccaattag agacagaatg ctcaacattc atctaacaca tacattgcct | 1560 |
| ggtgactttg gtttggttga caagaatgaa tggcccatga tttgtgcttg gttggtaaag | 1620 |
| aatggttacc aatctaccat ggcaagctac tgcgctaaat ggggcaaagt tcctgattgg | 1680 |
| tcagaaaact gggcggagcc aaaggtgccg actcctataa attcactagg ttcggcacgc | 1740 |
| tcaccattca cgacaccgaa aagtacgcct ctcagccaga actatgcaat aactccactt | 1800 |
| gcatcggatc tcgaggacct ggctttagag ccttggagca caccaaatac tcctgttgcg | 1860 |
| ggcactgcag aaacccagaa cactgggaa gctggttcca aagcctgcca agatggtcaa | 1920 |
| ctgagcccaa cttggtcaga gatcgaggag gatttgagag cgtgcttcgg tgcggaaccg | 1980 |

```
ttgaagagag acttcagcga gccgctgaac ttggactaa              2019
```

<210> SEQ ID NO 13
<211> LENGTH: 2019
<212> TYPE: DNA
<213> ORGANISM: Mouse parvovirus 4b

<400> SEQUENCE: 13

```
atggctggaa atgcttactc tgatgaagtt tgggagcaa ccaactggtt aaaggaaaaa    60
agtaaccagg aagtattctc atttgttttt aaaaatgagg atgttcaact gaatggaaaa   120
gatattggat ggaatagcta caaaaaagag ctacaggagg acgagctgaa atctttacaa   180
cgaggagcgg aaactacctg ggaccaaagc gaggacatgg aatgggaatc tacagtggat   240
gaagtaacca aaaagcaagt attcattttt gactctttag ttaaaaaatg tttgtttgaa   300
gtgcttaaca caaagaacat agctcctagt gatgttaatt ggtttgtaca gcatgaatgg   360
ggaaaagacc aaggctggca ttgccatgta ctaattggag caaagactt tagtcaagct   420
caaggaaagt ggtggagaag gcagctaaat gtttactgga gcagatggtt ggtaacagcc   480
tgtaatgtgc agctatcacc agctgaaaga attaaactaa gagaaatagc agaagacaat   540
gagtgggtta gcttgctcac ttataagcat aagcaaacca aaaaggacta tactaagtgt   600
gttcttttg gcaacatgat tgcttactac ttttaacca aaagaaaat aagcactagt   660
ccaccaaggg acgaggcta ttttctaagc agtgactctg gctggaaaac taacttttta   720
aaagaaggcg aacgccatct agtgagcaaa ctatacactg atgacatgcg ccagaaacg   780
gttgaaacca cagtaaccac tgcacaggaa actaagcgcg gcagaattca aactaaaaaa   840
gaggtttcta ttaaaaccac acttaaagag ctggtgcata aagagtaac ctcaccagaa   900
gactggatga tgatgcagcc agacagttat attgaaatga tggctcaacc aggtggagaa   960
aacctgctga aaaatacgct agagatttgt acactaactc tagctagaac caaaacagca  1020
tttgacttga ttttagaaaa agctgaaacc agcaaactaa ctaacttttc actgccggac  1080
acaagaacct gcaagatttt tgcttttcat ggctggaact acattaaagt ttgccatgct  1140
atttgctgtg ttttaaacag acaaggaggc aaaagaaata ctgttttatt tcatggacca  1200
gccagtacag gcaaatccat tattgcacaa gccatagcac aggcagttgg taatgttggt  1260
tgctataatg cagcaaatgt aaactttcca ttcaatgact gtaccaacaa gaacttgatt  1320
tgggtggaag aagctggtaa cttttggacag caagtaaacc agttcaaagc catttgctct  1380
ggtcaaacta ttcgcattga tcaaaaagga aaaggcagca aacagattga accaacacca  1440
gtcatcatga ccacaaatga aaacattaca gtggtcagaa taggctgtga agaaagacca  1500
gagcacactc aaccaatcag agacagaatg cttaacattc atctaacaca tacattgcct  1560
ggtgactttg gtttggttga caaaaatgag tggcccatga tttgtgcttg gttggtaaag  1620
aatggttacc aatctaccat ggcaagctac tgtgctaaat gggcaaagt tcctgattgg  1680
acggaaaact gggcggagcc gaaggtgccg actcctataa attcactagg ttcggcacgc  1740
tcaccattca cgacaccgaa aagtacgcct ctcagccaga actatgcact aactccactt  1800
gcatcggatc tcgaggacct ggctttagag ccttggagca caccaaatac tcctgttgtg  1860
ggcactgcag aaacccagaa cactggggaa gctggttcca aagcctgcca agatggtcaa  1920
ctgagcccaa cttggtcaga gatcgaggag gatttgagag cgtgcttcgg tgcggaaccg  1980
ttgaagaaag acttcagcga gccgctgaac ttggactaa               2019
```

```
<210> SEQ ID NO 14
<211> LENGTH: 2042
<212> TYPE: DNA
<213> ORGANISM: Mouse parvovirus 4a

<400> SEQUENCE: 14
atggctggaa atgcttactc tgatgaagtt ttgggagcaa ccaactggtt aaaggaaaaa        60
aataatcagg aagtgttctc atttgttttt aaaaatgagg atgttcaact gaatggaaaa       120
gatatcggat ggaatagtta caaaaaggag ctgcaggagg acgagctgaa atctttacaa       180
cgaggagcgg aaactacctg ggaccaaagc gaggacatgg aatgggaatc tgcagtggat       240
gaagtgacca aaaagcaagt attcattttt gactctttag ttaaaaaatg tttgtttgaa       300
gtgcttaaca caagaacat agctcctgct gatgttaatt ggtttgtgca gcatgaatgg        360
ggaaaagacc aaggctggca ctgccatgta ctaattggag caaggacttt tagtcaagct       420
caaggaaagt ggtggagaag gcagctaaat gtttactgga gcagatggtt agtaacagcc       480
tgtaatgtac agctatcacc agctgaaaga attaaactaa gagaaatagc agaagacaat       540
gagtgggtta ccttgctcac ttataagcat aagcaaacca aaaggacta tactaagtgt        600 gttctttttg caacatgat tgcttactac tttttaacca aaaagaaaat aagcactagt        660
ccaccaaggg acggaggcta ttttctgagc agtgactctg gctggaaaac taacttttta       720
aaagagggcg aacgccatct agtgagcaaa ctatatactg atgacatgcg gccagaaacg       780
gttgaaacca cagtaaccac tgcgcaggaa actaagcgcg gcagaattca actaaaaaa        840 gaggtttcaa ttaaaaccac acttaaagag ctggtgcata aaagagtaac ctcaccagaa       900
gactggatga tgatgcagcc agacagttac attgaaatga tggctcaacc aggtggagaa       960
aacctgctga aaaatacgct agagatttgt acactaactc tagccagaac caaaacagca      1020
tttgacttga ttttagaaaa agctgaaacc agcaaactaa caaactttc actgcctgat       1080 acaagaacct gcaagatttt tgcttttcat ggctggaact acattaaagt ttgccatgct      1140
atttgctgtg ttttaaacag acaaggaggc aaaagaaata ctgttttatt tcatggacca      1200
gccagtacag gcaaatctat cattgcacaa gccatagcac aggcagttgg taatgttggt      1260
tgctataatg cagcaaatgt gaactttcca ttcaatgact gtaccaacaa gaacttaatt      1320
tgggtggaag aagctggtaa cttttggacaa caagtaaacc agtttaaagc catttgctct      1380
ggtcaaacta ttcgcattga tcaaaaagga aaaggcagca agcagattga accaacacca      1440
gtcatcatga ccacaaatga aaacatcaca gtggtcagaa taggctgcga agagagacca      1500
gaacacactc aaccaatcag agacagaatg cttaacattc atctaacaca tacattgcct      1560
ggtgactttg gtttggttga caaaaatgag tggcccatga tttgtgcttg gttggtaaag      1620
aatggttacc aatctaccat ggcaagctac tgtgctaaat gggcaaagt tcctgattgg      1680 acagaaaact gggcggagcc gaaggtgccg actcctataa attcactagg ttcggcacgc      1740
tcaccattca cgacaccgaa aagtacgcct ctcagccaga actatgcact aactccactt      1800
gcatcggatc tcgaggacct ggctttagag ccttggagca caccaaatac tcctgttgcg      1860
ggcactgcag aaacccagaa cactggggaa gctggttcca aagcctgcca agatggtcaa      1920
ctgagcccaa cttggtcaga gatcgaggag gatttgagag cgtgcttcgg tgcggaaccg      1980
ttgaagaaag acttcaacga gccgctgaac ttggactaag gtacgatggc gcctccagct      2040
aa                                                                      2042

<210> SEQ ID NO 15
<211> LENGTH: 2019
<212> TYPE: DNA
<213> ORGANISM: Mouse parvovirus 1b
```

<400> SEQUENCE: 15

```
atggctggaa atgcttactc tgatgaagtt ttgggaacaa ccaactggtt aaaggaaaaa      60
agtaaccagg aagtgttctc atttgttttt aaaactgagg atgttcaact aaatggaaaa     120
gatatcggat ggaataatta caaaaaggag ctgcaggagg acgagctgaa atctttacaa     180
cgaggagcgg aaactacctg gaccaaagc gaggacatgg aatgggaatc tacagtggat      240
gaaatgacca aaaagcaagt attcatttat gactctttag ttaaaaaatg tttgtttgaa     300
gtgcttagca caaagaatat agctcctgct gatgttactt ggtttgtgca gcatgaatgg     360
gggaaagacc aaggctggca ctgccatgta ctaattggag caaggactt tagtcaagct      420
caaggaaaat ggtggagaag gcagctaaat gtttactgga gcagatggtt ggtaacagcc     480
tgtaatgtgc agctaacacc agctgaaaga attaaactaa gagaaatagc agaagacagt     540
gagtgggtta ctttgctcac ttataagcat aagcaaacca aaaaggacta taccaagtgt     600
gttcttttg aaacatgat tgcttactac tttttaacca agaagaaaat aagcactagt       660
ccgccaaggg acggaggcta ttttctgagc agtgactctg ctggaaaac taactttta       720
aaagagggcg aacgccatct agtgagcaaa ctatacactg atgacatgcg ccagaaacg      780
gttgaaacca cagtaaccac tgcgcaggaa actaagcgcg gcagaattca aactaaaaaa     840
gaggtttcta ttaaaaccac acttaaagag ctggtgcata aaagagtaac ctcaccagaa     900
gactggatga tgatgcagcc agacagttac attgaaatga tggctcaacc aggtggagaa     960
aacctgctga aaaatacgct agagatctgt acactaactc tagctagaac caaaacagca    1020
tttgacttga ttttagaaaa agctgaaacc agcaaactaa ccaacttttc actgcctgac    1080
acaagaaacct gcaagatctt tgcttttcat ggctggaact acattaaagt ttgccatgct   1140
atttgctgtg ttctaaacag acaaggaggc aaaagaaata ctgttttatt tcatggacca    1200
gccagtacag gcaaatccat tattgcacaa gccatagcac aggcagttgg taatgttggt    1260
tgctataatg cagcaaatgt gaactttcca ttcaatgact gtaccaacaa gaacttgatt    1320
tgggtggaag aagctggtaa cttttggacag caagtaaacc agtttaaagc catttgctct    1380
ggtcaaacaa ttcgcattga tcaaaaagga aaaggcagca agcagattga accaacacca    1440
gtcatcatga ccacaaatga aacattaca gtggtcaaaa taggctgcga ggagagacca     1500
gaacacactc aaccaatcag agacagaatg cttaacattc atctaacaca tacattgcct    1560
ggtgactttg gtttggttga caaaagtgag tggcccatga tctgtgcttg gttggtaaag    1620
aatggttacc aatctaccat ggcaagctac tgtgctaaat ggggcaaagt tcctgattgg    1680
acagaaaact gggcggagcc gaaggtgccg actcctataa attcactagg ttcggcacgc    1740
tcaccattca cgacaccgaa aagtacgcct ctcagccaga actatgcact aactccactt    1800
gcatcggatc tcgaggacct ggctttagag ccttggagca caccaaatac tcctgttgcg    1860
ggcactgcag aaacccagaa cactggggaa gctggttcca aagcctgcca agatggtcaa    1920
ctgagcccaa cttggtcaga gatcgaggag gatttgagag cgtgcttcgg tgcggaaccg    1980
ttgaagagag acttcagcga gccgctgaac ttggactaa                           2019
```

<210> SEQ ID NO 16
<211> LENGTH: 2019
<212> TYPE: DNA
<213> ORGANISM: Mouse parvovirus minute virus
<220> FEATURE:
<223> OTHER INFORMATION: immunosuppressive variant sequence

<400> SEQUENCE: 16

| | |
|---|---|
| atggctggaa atgcttactc tgatgaagtt ttgggaacaa ccaactggtt aaaggaaaaa | 60 |
| agtaaccagg aagtgttctc atttgttttt aaaactgagg atgttcaact aaatggaaaa | 120 |
| gatatcggat ggaataatta caaaaaggag ctgcaggagg acgagctgaa atctttacaa | 180 |
| cgaggagcgg aaactacctg ggaccaaagc gaggacatgg aatgggaatc tacagtggat | 240 |
| gaaatgacca aaaagcaagt attcatttat gactctttag ttaaaaaatg tttgtttgaa | 300 |
| gtgcttagca caaaaatat agctcctgct gatgttactt ggtttgtgca gcatgaatgg | 360 |
| gggaaagacc aaggctggca ctgccatgta ctaattggag caaggactt tagtcaagct | 420 |
| caaggaaaat ggtggagaag gcagctaaat gtttactgga gcagatggtt ggtaacagcc | 480 |
| tgtaatgtgc agctaacacc agctgaaaga attaaactaa gagaaatagc agaagacagt | 540 |
| gagtgggtta ctttactcac ttataaacat aagcaaacca aaaaggacta tactaaatgt | 600 |
| gttctttttg gaaatatgat tgcttactac ttttttaacca aaaagaaaat aagcaccagt | 660 |
| ccgccaaggg acggaggcta ttttctaagc agtgactctg gctggaaaac taactttta | 720 |
| aaagagggcg aacgccatct agtgagcaaa ttatacactg atgacatgcg gccagaaacg | 780 |
| gttgaaacca cagtaaccac tgcgcaggaa actaagcgcg gcagaattca aactaaaaaa | 840 |
| gaggtttcta ttaaaaccac acttaaagag ctagtgcata aaagagtaac ctcaccagaa | 900 |
| gactggatga tgatgcagcc agacagttac attgaaatga tggctcaacc aggtggagaa | 960 |
| aacctgctga aaatacgct agagatttgt acgctaactc tagccagaac aaaaacagca | 1020 |
| tttgacttga ttttagaaaa agctgaaacc agcaaactaa ccaactttc actgcctgac | 1080 |
| acaagaacct gcaagatttt tgcttttcat ggctggaact atgttaaagt ttgccatgct | 1140 |
| atttgctgtg ttctaaacag acaaggaggc aaaagaaata ctgttttatt tcacggacca | 1200 |
| gccagtacag gcaaatctat tattgcacaa gccatagcac aggcagttgg taatgttggt | 1260 |
| tgctataatg cagctaatgt gaactttcca tttaatgact gtacgaacaa aaacttgatt | 1320 |
| tgggtagaag aagctggtaa cttttggacag caagtaaacc agtttaaagc catttgctct | 1380 |
| ggtcaaacta ttcgcattga tcaaaaagga aaaggcagca acaaattga ccaacacca | 1440 |
| gtcatcatga ccacaaatga aaacattaca gtggtcagaa taggctgcga agagagacca | 1500 |
| gaacacactc aaccaattag agacagaatg ctcaacattc atctaacaca tacattgcct | 1560 |
| ggtgactttg gtttggttga caagaatgaa tggcccatga tttgtgcttg gttggtaaag | 1620 |
| aatggttacc aatctaccat ggcaagctac tgcgctaaat ggggcaaagt tcctgattgg | 1680 |
| tcagaaaact gggcggagcc gaaggtgccg actcctataa attcactagg ttcggcacgc | 1740 |
| tcaccattca cgacaccgaa aagtacgcct ctcagccaga actatgcact aactccactt | 1800 |
| gcatcggatc tcgaggacct ggctttagag ccttggagca caccaaatac tcctgttgcg | 1860 |
| ggcactgcag aaacccagaa cactggggaa gctggttcca aagcctgcca agatggtcaa | 1920 |
| ctgagcccaa cttggtcaga gatcgaggag gatttgagag cgtgcttcgg tgcggaaccg | 1980 |
| ttgaagagag acttcagcga gccgctgaac ttggactaa | 2019 |

<210> SEQ ID NO 17
<211> LENGTH: 2019
<212> TYPE: DNA
<213> ORGANISM: Mouse parvovirus 1

<400> SEQUENCE: 17

| | |
|---|---|
| atggctggaa atgcttactc tgatgaagtt ttgggaacaa ccaactggtt aaaggaaaaa | 60 |

| | |
|---|---|
| agtaaccagg aagtgttctc atttgttttt aaaactgagg atgttcaact aaatggaaaa | 120 |
| gatatcggat ggaataatta caaaaaggag ctgcaggagg acgagctgaa atctttacaa | 180 |
| cgaggagcgg aaactacctg ggaccaaagc gaggacatgg aatgggaatc tacagtggat | 240 |
| gaaatgacca aaaagcaagt attcatttat gactctttag ttaaaaaatg tttgtttgaa | 300 |
| gtgcttagca caaagaatat agctcctgct gatgttactt ggtttgtgca gcatgaatgg | 360 |
| gggaaagacc aaggctggca ctgccatgta ctaattggag caaggactt tagtcaagct | 420 |
| caaggaaaat ggtggagaag gcagctaaat gtttactgga gcagatggtt ggtaacagcc | 480 |
| tgtaatgtgc agctaacacc agctgaaaga attaaactaa gagaaatagc agaagacagt | 540 |
| gagtgggtta ctttacttac ttataaacat aagcaaacca aaaaggacta tactaaatgt | 600 |
| gttcttttg gaaatatgat tgcttactac tttttaacca aaaaaaaaat aagcaccagt | 660 |
| ccgccaagag acggaggcta ttttctaagc agtgactctg gctggaaaac taacttttta | 720 |
| aaagaaggcg aacgccatct agtgagcaaa ctatacactg atgacatgcg accagaaacg | 780 |
| gttgaaacca cagtaaccac tgcgcaggaa actaagcgcg gcagaattca aactaaaaaa | 840 |
| gaggtttcta ttaaaaccac acttaaagag ctggtgcata aaagagtaac ctcaccagaa | 900 |
| gactggatga tgatgcagcc agacagttac attgaaatga tggctcaacc aggtggagaa | 960 |
| aacctgctga aaatacgct agagatctgt acactaactc tagctagaac caaaacagca | 1020 |
| tttgacttga ttttagaaaa agctgaaacc agcaaactaa ccaacttttc actgcctgac | 1080 |
| acaagaacct gcaagatctt tgcttttcat ggctggaact acattaaagt ttgccatgct | 1140 |
| atttgctgtg ttctaaacag acaaggaggc aaaagaaata ctgttttatt tcatggacca | 1200 |
| gccagtacag gcaaatccat tattgcacaa gccatagcac aggcagttgg taatgttggt | 1260 |
| tgctataatg cagcaaatgt gaactttcca ttcaatgact gtaccaacaa gaacttaatt | 1320 |
| tgggtggaag aagctggtaa ctttggacaa caagtaaacc agtttaaagc catttgctct | 1380 |
| ggtcaaacaa ttcgcattga tcaaaaagga aaaggcagca agcagattga accaacacca | 1440 |
| gtcatcatga ccacaaatga aaacattaca gtggtcaaaa taggctgcga ggaaagacca | 1500 |
| gaacacactc aaccaatcag agacagaatg cttaacattc atctaacaca tacattgcct | 1560 |
| ggtgactttg gtttggttga caaaaatgag tggcccatga tttgtgcttg gttggtaaag | 1620 |
| aatggttacc aatctaccat ggcaagctac tgtgctaaat ggggcaaagt tcctgattgg | 1680 |
| acggaaaact gggcggagcc gaaggtgccg actcctataa attcactagg ttcggcacgc | 1740 |
| tcaccattca cgacaccgaa aagtacgcct ctcagccaga actatgcact aactccactt | 1800 |
| gcatcggatc tcgaggacct ggctttagag ccttggagca caccaaatac tcctgttgcg | 1860 |
| ggcactgcag aaacccagaa cactgggaa gctggttcca aagcctgcca agatggtcaa | 1920 |
| ctgagcccaa cttggtcaga gatcgaggag gatttgagag cgtgcttcgg tgcggaaccg | 1980 |
| ttgaagaaag acttcagcga gccgctgaac ttggactaa | 2019 |

```
<210> SEQ ID NO 18
<211> LENGTH: 2019
<212> TYPE: DNA
<213> ORGANISM: Mouse parvovirus 5a

<400> SEQUENCE: 18
```

| | |
|---|---|
| atggctggaa atgcttactc tgatgaagtt ttgggaacaa ccaactggtt aaaggaaaaa | 60 |
| agtaaccagg aagtgttctc atttgttttt aaaactgaag atgttcaact gaatggaaaa | 120 |
| gatattggat ggaataatta cagaaaggag ctgcaagagg acgagctaaa atctttacaa | 180 |

-continued

```
cgaggagcgg aaactacctg ggaccaaagc gaggacatgg aatgggaatc tacagtggat      240
gaagtgacca aaaagcaagt attcatttat gactctttag ttaaaaaatg tttgtttgaa      300
gtacttagca caaagaacat agctcctagt gatgttaatt ggtttgtgca gcatgaatgg      360
ggaagagacc aaggctggca ttgccatgta ctaattggag gcaaagactt tagtcaagct      420
caaggaaagt ggtggagaag gcagctaagt gtttactgga gcagatggtt ggtaacagct      480
tgtaatgtac agctaacacc agctgaaaga attaaactaa gagaaatagc agaagacagt      540
gaatgggtta ccttgctcac ttataagcat aagcaaacca aaaggacta taccaagtgt       600 gttctttttg gaaacataat tgcttactac tttttaacta aaaagaaaat aagcaccagt      660
ccgccaagag acggaggcta ttttcttagc agtgactctg gctggaaaac taacttttta      720
aaagagggcg aacgccatct agtgagcaaa ctatacactg atgacatgcg gccagaaacg      780
gttgaaacca cagtaaccac tgcgcaggaa actaagcgcg gcagaattca aactaaaaaa      840
gaggtttcaa ttaaaaccac acttaaagag ctggtgcata agagtaac ctcaccagaa        900 gactggatga tgatgcagcc agacagttat attgaaatga tggctcaacc aggtggagaa      960
aacctgctaa aaaatacgct agagatttgt acactaactc tagctagaac caaaacagca     1020
tttgacttga ttttagaaaa agctgaaacc agcaaactaa ccaacttttc actgccggac     1080
acaagaacct gcaaaatttt tgcttttcat ggctggaact atgttaaagt ttgccatgct     1140
atttgctgtg ttctaaacag acaaggaggc aagagaaata ctgtttattt tcatggacca     1200
gccagcacag gcaaatccat tattgcacaa gccatagcac aggcagttgg taatgttggt     1260
tgctataatg cagcaaatgt gaactttcca ttcaatgact gtaccaacaa gaacttaatt     1320
tgggtggaag aagctggtaa cttttggacaa caagtaaacc agtttaaagc catttgctct     1380
ggtcaaacaa ttcgcattga tcaaaaagga aaaggcagca agcagattga accaacacca     1440
gtcatcatga ccacaaatga aacattaca gtggtcaaaa taggctgcga ggaaagacca      1500
gaacacactc aaccaatcag agacagaatg cttaacattc atctaacaca tacattgcct     1560
ggtgactttg gtttggttga caaaaatgag tggcccatga tttgtgcttg gttggtaaag     1620
aatggttacc aatctaccat ggcaagctac tgtgctaaat ggggcaaagt tcctgattgg     1680
acggaaaact gggcggagcc gaaggtgccg actcctataa attcactagg ttcggcacgc     1740
tcaccattca cgacaccgaa aagtacgcct ctcagccaga actatgcact aactccactt     1800
gcatcggatc tcgaggacct ggctttagag ccttggagca caccaaatac tcctgttgcg     1860
ggcactgcga aaacccagaa cactggggaa gctggttcca aagcctgcca agatggtcaa     1920
ctgagcccaa cttggtcaga gatcgaggag gatttgagag cgtgcttcgg tgcggaaccg     1980
ttgaagaaag acttcagcga gccgctgaac ttggactaa                            2019
```

<210> SEQ ID NO 19
<211> LENGTH: 2019
<212> TYPE: DNA
<213> ORGANISM: Mouse parvovirus UT

<400> SEQUENCE: 19

```
atggctggaa acgcttactc tgatgaagtt ttgggaacaa ccaactggtt aaaggaaaaa       60
agtaaccagg aagtgttctc atttgttttt aaaactgagg atgttcaact aaatggaaaa      120
gatatcggat ggaataatta cagaaaggag ctgcaggagg acgagctgaa atctttacaa      180
cgaggagcag aaactacctg ggaccaaagc gaggacatgg aatgggaatc tacagtggat      240
```

```
gaagtgacca aaaagcaagt attcatttat gactctttag ttaaaaaatg tttgtttgaa      300
gtgcttaaca caaagaacat atctcctggt gatgttaatt ggtttgtgca gcatgaatgg      360
ggaaaagacc aaggctggca ttgccatgta ctaattggag gcaaagactt tagccaagct      420
caaggaaagt ggtggagaag gcagctaagt gtttactgga gcagatggtt agtaacagcc      480
tgtaatgtgc agctatcacc agctgaaaga attaaactaa gagaaatagc agaagacagt      540
gagtgggtta ccttgctcac ttataagcat aagcaaacca aaaagacta tactaagtgt        600 gttcttttg gcaacataat tgcttactac ttttaacca agaagaaaat aagcactagt         660
ccgccaaggg acggaggcta ttttctgagc agtgactctg gctggaaaac taactttta        720 aaagagggcg aacgccatct agtgagcaaa ctatacactg atgacatgcg gccagaaacg      780
gttgaaacca cagtaaccac tgcgcaggaa actaagcgcg gcagaattca aactaaaaaa      840
gaagtttcta ttaaaccac acttaaagaa ctggtgcata aagagtaac ctcaccagaa         900 gactggatga tgatgcagcc agacagttac attgaaatga tggctcaacc aggtggagaa      960
aacctgctaa aaaatacgct agagatttgt acgctaactc tagctagaac caaaacagca     1020
tttgacttga ttttagaaaa agctgaaacc agcaaactaa ctaacttttc actgcctgac     1080
acaagaacct gcaagatttt tgcttttcat ggctggaact acattaaagt ttgccatgct     1140
atttgctgtg ttctaaacag acaaggaggc aaaagaaata ctgttttatt tcatggacca     1200
gccagtacag gcaaatccat tattgcacaa gccatagcac aggcagttgg taatgttggt     1260
tgctataatg cagcaaatgt gaactttcca ttcaatgact gtaccaacaa gaacttgatt     1320
tgggtggaag aagctggtaa ctttggacag caagtaaacc agtttaaagc catttgctct     1380
ggtcaaacaa ttcgcattga tcaaaaagga aaaggcagca agcagattga accaacacca     1440
gtcatcatga ccacaaatga gaacattaca gtggtcaaaa taggctgcga ggagagacca     1500
gaacacactc aaccaataag agacagaatg cttaacattc atctaacaca tacattgcct     1560
ggtgactttg gtttggttga caaaagtgag tggcccatga tctgtgcttg gttggtaaag     1620
aatggttacc aatctaccat ggcaagctac tgtgctaaat ggggcaaagt tcctgattgg     1680
tcagaaaact gggcggagcc gaaggtgccg actcctataa attcactagg ttcggcacgc     1740
tcaccattca cgacaccgaa agtacgcct ctcagccaga actatgcact aactccactt      1800
gcatcggatc tcgaggacct ggctttagag ccttggagca caccaaatac tcctgttgcg     1860
ggcactgcag aaacccagaa cactggggaa gctggttcca aagcctgcca agatggtcaa     1920
ctgagcccaa cttggtcaga gatcgaggag gatttgagag cgtgcttcgg tgcggaaccg     1980
ttgaagaaag acttcagcga gccgctgaac ttggactaa                             2019

<210> SEQ ID NO 20
<211> LENGTH: 2009
<212> TYPE: DNA
<213> ORGANISM: Mouse parvovirus 1e

<400> SEQUENCE: 20
atgcttactc tgatgaagtt ttgggaacaa ccaactggtt aaaggaaaaa agtaaccagg       60
aagtgttctc atttgttttt aaaactgaag atattcaact gaatgaaaaa gatattggat      120
ggaataatta cagaaaggag ctgcaagagg acgagctaaa atctttacaa cgaggagcgg      180
aaactacctg ggaccaaagc gaggacatgg aatgggaatc tacagtggat gaagtgacca      240
aaaagcaagt attcatttat gactctttag ttaaaaaatg tttgtttgaa gtgcttaaca      300
caaagaacat atctcctggt gatgttaatt ggtttgtgca gcatgaatgg ggaagagacc      360
```

-continued

```
aaggctggca ttgccatgta ctaattggag gcaaagactt tagtcaagct caaggaaagt      420
ggtggagaag gcagctaagt gtttactgga gcagatggtt ggtaacagcc tgtaatgtac      480
agctaacacc agctgaaaga attaaactaa gagaaatagc agaagacagt gaatgggtta      540
ccttgctcac ttataagcat aagcaaacca aaaaggacta taccaagtgt gttcttttg       600 gcaacataat tgcttactac ttttaacca agaagaaaat aagcaccagt ccgccaaggg       660
acggaggcta ttttcttagt agtgactctg gctggaaaac taactttta aaagagggcg       720 aacgccatct agtgagcaaa ctatacactg atgacatgcg gccagaaacg gttgaaacca      780
cagtaaccac tgcgcaggaa actaagcgcg gcagaattca aactaaaaaa gaggtttcta      840
ttaaaaccac acttaaagag ctagtgcata agagagtaac ctcaccagaa gactggatga      900
tgatgcagcc agacagttat attgaaatga tggctcaacc aggtggagaa aacctgctga      960
aaaatacgct agagatctgt acactaactc tagctagaac caaaacagca tttgacttga     1020
ttttagaaaa agctgaaacc agcaaactaa ccaactttc actgcctgac acaagaacct      1080
gcaagatctt tgcttttcat ggctggaact acattaaagt ttgccatgct atttgctgtg     1140
ttctaaacag acaaggaggc aaaagaaata ctgttttatt tcatggacca gccagtacag     1200
gcaaatccat tattgcacaa gccatagcac aggcagttgg taatgttggt tgctataatg     1260
cagcaaatgt gaactttcca ttcaatgact gtaccaacaa gaacttaatt tggggtggaag    1320 aagctggtaa ctttggacaa caagtaaacc agtttaaagc catttgctct ggtcaaacaa     1380
ttcgcattga tcaaaaagga aaaggcagca agcagattga accaacacca gtcatcatga     1440
ccacaaatga aaacattaca gtggtcaaaa taggctgcga ggaaagacca gaacacactc     1500
aaccaatcag agacagaatg cttaacattc atctaacaca tacattgcct ggtgactttg     1560
gtttggttga caaaaatgag tggcccatga tttgtgcttg gttggtaaag aatggttacc     1620
aatctaccat ggcaagctac tgtgctaaat ggggcaaagt tcctgattgg acggaaaact     1680
gggcggagcc gaaggtgccg actcctataa attcactagg ttcggcacgc tcaccattca     1740
cgacaccgaa aagtacgcct ctcagccaga actatgcact aactccactt gcatcggatc     1800
tcgaggacct ggctttagag ccttggagca caccaaatac tcctgttgcg ggcactgcag     1860
aaacccagaa cactggggaa gctggttcca aagcctgcca agatggtcaa ctgagcccaa     1920
cttggtcaga gatcgaggag gatttgagag cgtgcttcgg tgcggaaccg ttgaagagag     1980
acttcagcga gccgctgaac ttggactaa                                       2009
```

```
<210> SEQ ID NO 21
<211> LENGTH: 2019
<212> TYPE: DNA
<213> ORGANISM: Mouse parvovirus 1c
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t

<400> SEQUENCE: 21
```

```
atggctggaa atgcttactc tgatgaagtt ttgggaacaa ccaactggtt aaaggaaaaa       60
agtaaccagg aagtgttctc atttgttttt aaaactgaag atgttcaact aaatggaaaa      120
gatattggat ggaataatta cagaaaggag ctgcaagagg acgagctaaa atctttacaa      180
```

```
cgaggagcgg aaactacctg ggaccaaagc gaggacatgg aatgggaatc tacagtggat      240
gaagtgacca aaaagcaagt attcattat gactctttag ttaaaaaatg tttgtttgaa       300
gtgcttaaca caaagaacat atctcctggt gatgttaatt ggtttgtgca gcatgaatgg      360
ggaagagacc aaggctggca ttgccatgta ctaattggag caaagactt tagtcaagct       420 caaggaaagt ggtggagaag gcagctaagt gtttactgga gcagatggtt ggtaacagcc     480
tgtaatgtac agctaacacc agctgaaaga attaaactaa gagaaatagc agaagacagt     540
gaatgggtta ccttgctcac ttataagcat aagcaaacca aaaggacta taccaagtgt      600 gttcttttng gcaacataat tgcttactac ttttaacca agaagaaat aagcaccagt       660 ccgccaaggg acggaggcta ttttcttagt agtgactctg gctggaaaac taacttttta    720
aaagagggcg aacgccatct agtgagcaaa ctatacactg atgacatgcg ccagaaacg     780 gttgaaacca cagtaaccac tgcgcaggaa actaagcgcg gcagaattca aactaaaaaa    840
gaggtttcta ttaaaaccac acttaaagag ctagtgcata agagagtaac ctcaccagaa    900
gactggatga tgatgcagcc agacagttat attgaaatga tggctcaacc aggtggagaa    960
aacctgctga aaatacgct agagatctgt acactaactc tagctagaac caaaacagca    1020
tttgacttga ttttagaaaa agctgaaacc agcaaactaa ccaactttc actgcctgac     1080 acaagaacct gcaagatctt tgcttttcat ggctggaact acattaaagt ttgccatgct    1140
atttgctgtg ttctaaacag acaaggaggc aaaagaaata ctgttttatt tcatggacca    1200
gccagtacag gcaaatccat tattgcacaa gccatagcac aggcagttgg taatgttggt    1260
tgttataatg cagcaaatgt gaactttcca ttcaatgact gtaccaacaa gaacttaatt    1320
tgggtggaag aagctggtaa ctttggacaa caagtaaacc agtttaaagc catttgctct    1380
ggtcaaacaa ttcgcattga tcaaaaagga aaggcagca agcagattga accaacacca    1440
gtcatcatga ccacaaatga aaacattaca gtggtcaaaa taggctgcga ggaaagacca   1500
gaacacactc aaccaatcag agacagaatg cttaacattc atctaacaca tacattgcct    1560
ggtgactttg gtttggttga caaacatgan tggcccatga tttgtgcttg gttggtaaag   1620
aatggttacc aatctaccat ggcaagctac tgtgctaaat ggggcaaagt tcctgattgg   1680
acggaaaact gggcggagcc gaaggtgccg actcctataa attcactagg ttcggcacgc   1740
tcaccattca cgacaccgaa aagtacgcct ctcagccaga actatgcact aactccactt    1800
gcatcggatc tcgaggacct ggctttagag ccttggagca caccaaatac tcctgttgcg    1860
ggcactgcag aaacccagaa cactggggaa gctggttcca aagcctgcca agatggtcaa   1920
ctgagcccaa cttggtcaga gatcgaggag gatttgaaag cgtgcttcgg tgcggaaccg   1980
ttgaagagag acttcagcga gccgctgaac ttggactaa                          2019
```

<210> SEQ ID NO 22
<211> LENGTH: 2019
<212> TYPE: DNA
<213> ORGANISM: Hamster parvovirus

<400> SEQUENCE: 22

```
atggctggaa atgcttactc tgatgaagtt ttgggaacaa ccaactggtt aaaagagaaa      60
agtaaccagg aagtgttctc atttgttttt aaaaatgaag atgttcagct caatggaaaa    120
gatatcggat ggaatagtta caaaaaggag ctgcaagagg aagagctgaa atctttacaa    180
cgaggagcgg aaactacctg ggaccagagc gaggacatgg aatgggaatc ttcagtggat   240
gaactaacca aaaagcaagt attcattttt gactctttag ttaaaaaatg tttgtttgaa     300
```

```
gtgctgagta caaagaacat agcacctagt gatgttactt ggtttgtaca gcatgaatgg    360
ggaaaagacc aaggctggca ctgtcatgta ctaattggag gcaaggactt tagccaagct    420
caaggaaaat ggtggagaag gcagttaaat gtttactgga gcagatggtt ggtaacagcc    480
tgtagtgtgc agctattacc agctgaaaga attaagctga gagagatagc ggaagaccaa    540
gaatgggtca ctttgcttac ttataagcat aagcaaacca aaaaagacta taccaagtgt    600
gtttgctttg gaaatatagt tgcttactac tttttatcca agaagaaaat atgcaccagt    660
ccaccaaggg acggaggcta ttttcttagc agtgactctg gctggaaaac taacttttta    720
aaagaaggcg aacgccatct agtgagcaaa ctatacactg atgacatgcg gccagaaacg    780
gttgaaacca cagtaaccac tgcgcaggaa actaagcgcg gcagaattca aactaaaaaa    840
gaggtctcta ttaaaaccac acttaaagag ctggtgcata agagagtaac ctcaccagaa    900
gactggatga tgatgcagcc agacagttac attgaaatga tggctcaacc aggtggagaa    960
aacctgctga aaaatacgct agagatttgt acactaactc tagccagaac aaaaacagca   1020
tttgacttaa ttttagaaaa agctgaaacc agcaaactaa ccaacttttc actgccggac   1080
acaagaacct gcaagatctt tgcttttcat ggctggaact atattaaagt ttgccatgct   1140
atttgctgtg ttctaaacag acaaggaggc aaaagaaata ctgtttatt tcatggacca   1200 gccagtacag gcaaatccat tattgcacaa gccatagcac aggcagttgg taatgttggt   1260
tgctataatg cagcaaatgt gaactttcca tttaatgact gcaccaacaa aaacctgatt   1320
tgggtggaag aagctggtaa ctttggacag caagtaaacc agtttaaagc catttgctct   1380
ggtcaaacta ttcgcattga tcaaaaagga aaaggcagca acagattga accaacacca   1440 gtcatcatga ccacaaatga aaacattaca gtggtcaaaa taggctgtga agaaagacca   1500
gaacacactc aaccaatcag agacagaatg cttaacattc atctaacaca tacattgcct   1560
ggtgactttg gtttggttga caaacatgaa tggcccatga tttgtgcttg gttggtaaag   1620
aatggttacc aatctaccat ggcaagctac tgtgctaaat ggggcaaagt tcctgattgg   1680
acggaaaact gggcggagcc gaaggtgccg actcctataa attcactagg ttcggcacgc   1740
tcaccattca cgacaccgaa aagtacgcct ctcagccaga actatgcact aactccactt   1800
gcatcggatc tcgaggacct ggctttagag ccttggagca caccaaatac tcctgttgcg   1860
ggcactgcaa aaacccagaa cactgggaa gctggttcca aagcctgcca agatggtcaa   1920
ctgagcccaa cttggtcaga gatcgaggag gatttgagag cgtgcttcgg tgcggaaccg   1980
ttgaagagag acttcagcga gccgctgaac ttggactaa                          2019
```

<210> SEQ ID NO 23
<211> LENGTH: 2019
<212> TYPE: DNA
<213> ORGANISM: Mouse parvovirus 3

<400> SEQUENCE: 23

```
atggctggaa acgcttactc tgatgaagtt ttaggaacaa ccaactggtt aaaggaaaaa     60
agtaaccagg aagtgttctc atttgttttt aaaaatgaag atgttcaact gaatggaaaa    120
gatatcggat ggaataatta cagaaaggag ctgcaggagg acgagctgaa atctttacaa    180
cgaggagcgg aaactacctg ggaccaaagc gaggacatgg aatgggaatc tgcagtggat    240
gaactaacca aaaagcaagt attcatttat gactcttttag ttaaaaaatg tttgtttgaa    300
gtgctgagta caaagaacat agctcctagt gatgttactt ggtttgtacg gcatgaatgg    360
```

-continued

```
ggaaaagacc aaggctggca ctgtcatgtg ctcattggag gcaaggactt tagccaagct    420
caaggaaaat ggtggagaag gcagttaaat gtttactgga gcagatggtt agtaacagcc    480
tgtaatgtgc agttatcacc agctgaaaga attaagctga gagagatagc ggaagaccaa    540
gaatgggtca ctttgcttac ttataagcat aagcaaacca aaaaggacta taccaagtgt    600 gttcttttg gaaatatagt tgcttactac tttttaacca gaagaaaat aagcaccagt     660 ccaccaaggg acggagacta ttttctgagc agtgactctg gctggaaaac taactttta    720 aaagagggcg aacgccatct agtgagcaaa ctatacactg atgacatgcg accagaaacg    780
gttgaaacca cagtaaccac tgcgcaggaa actaagcgcg gcagaattca aactaagaaa    840
gaggtctcta ttaaaaccac acttaaagag ctggtgcata aaagagtaac ctcaccagaa    900
gactggatga tgatgcagcc agacagttac attgaaatga tggctcaacc aggtggagaa    960
aacctgctga aaaatacgct agagatttgt acactaactc tagccagaac aaaaacagca   1020
tttgacttga ttttagaaaa agctgaaacc agcaaactaa ccaacttttc actgccggac   1080
acaagaacct gcaagatctt tgcttttcat ggctggaact atattaaagt ttgccatgct   1140
atttgctgtg ttctaaacag acaaggaggc aaaagaaata ctgttttatt tcatggacca   1200
gccagtacag gcaaatccat tattgcacaa gccatagcac aggcagttgg taatgttggt   1260
tgctataatg cagcaaatgt gaactttcca ttcaatgact gcaccaacaa aaacctgatt   1320
tgggtagaag aagctggtaa cttggacag caagtaaacc aatttaaagc catttgctct    1380
ggtcaaacta ttcgcattga tcaaaaagga aaaggcagca acagattga accaacacca    1440 gtcatcatga ccacaaatga aaacattaca gtggtcaaaa taggctgtga agaaagacca   1500
gaacacactc aaccaatcag agatagaatg cttaacattc atctaacaca tacattgcct   1560
ggtgactttg gtttggttga caaacatgaa tggcccatga tttgtgcttg gttggtaaag   1620
aatggttacc aatctaccat ggcaagctac tgtgctaaat ggggcaaagt tcctgattgg   1680
acggaaaact gggcggagcc gaaggtgccg actcctataa attcactagg ttcggcacgc   1740
tcaccattca cgacaccgaa aagtacgcct ctcagccaga actatgcact aactccactt   1800
gcatcggatc tcgaggacct ggctttagag ccttggagca caccaaatac tcctgttgcg   1860
ggcactgcag aaacccagaa cactggggaa gctggttcca aagcctgcca agatggtcaa   1920
ctgagcccaa cttggtcaga gatcgaggag gatttgagag cgtgcttcgg tgcggaaccg   1980
ttgaagagag acttcagcga gccgctgaac ttggactaa                          2019
```

<210> SEQ ID NO 24
<211> LENGTH: 2019
<212> TYPE: DNA
<213> ORGANISM: Mouse minute virus

<400> SEQUENCE: 24

```
atggctggaa atgcttactc tgatgaggtt ttgggagcaa ccaactggtt aaaggaaaaa     60
agtaaccagt tagtattctc atttgttttt aaaaatgaag atgttcaatt gaatggaaaa    120
gatatcggat ggaatagtta cagaaaggag ctgcaagagg acgagctaaa atctttacaa    180
cgaggagcgg aaactacctg gaccagagc gaggacatgg aatgggaatc ttcagtggat    240
gaactaacca caaagcaagt attcattttt gactctttag ttaaaaagtg tttatttgaa    300
gtgctaagta caaagaacat agctcctagt gatgttaatt ggtatgtgca gcatgaatgg    360
ggaaaagacc aaggctggca ttgccatgta ctaattggag gcaaagactt tagccaagct    420
caaggaaagt ggtggagaag gcagctaaat gtttactgga gcagatggtt ggtaacagcc    480
```

```
tgcagtgtgc agctatcacc agccgaaaga attaagctga gagaaatagc ggaagaccaa    540
gaatgggtca ctttgcttac ttataagcat aagcaaacca aaaaagacta taccaaatgt    600
gtttgctttg gaaatatgat tgcttactac tttttaacca agaagaaaat atgcactagt    660
ccaccaaggg acggaggcta ttttcttagc agtgactctg gctggaaaac taacttttta    720
aaagaaggcg aacgccatct agtgagcaaa ctatacactg atgacatgcg gccagaaacg    780
gttgaaacca cagtaaccac tgcgcaggaa actaagcgcg gcagaattca aactaaaaaa    840
gaggtttcta ttaaaaccac acttaaagag ctggtgcata agagagtaac ctcaccagaa    900
gactggatga tgatgcagcc agacagttac attgaaatga tggctcagcc aggtggagaa    960
aacctgctta aaaatacgct agagatctgt acgctaactc tagctagaac caaaacagcc   1020
tttgacttga ttttagaaaa agctgaaacc agcaaactaa ccaactttc actgccggac    1080 acaagaacct gtaagatttt tgcttttcat ggctggaact acattaaagt ttgccatgct   1140
atttgctgtg ttctaaacag acaaggaggc aaaagaaata ctgttttatt tcatggacca   1200
gccagtacag gcaaatccat cattgcacaa gccatagcac aggcagttgg taatgttggt   1260
tgctataatg cagcaaatgt gaactttcca ttcaatgact gcaccaacaa aaacctgatt   1320
tgggtggaag aagctggtaa cttttggacag caagtaaacc aatttaaagc catttgctct   1380
ggtcaaacta ttcgcattga tcaaaaagga aaaggcagca agcagattga accaacacca   1440
gtcatcatga ccacaaatga aacattaca gtggtcagaa taggctgcga agagagacca    1500
gaacacactc aaccaattag agacagaatg ctcaacattc atctaacaca tacattgcct   1560
ggtgactttg gtttggttga caaaaatgaa tggcccatga tttgtgcttg gttggtaaag   1620
aatggttacc aatctaccat ggcaagctac tgtgctaaat ggggcaaagt tcctgattgg   1680
tcagaaaact gggcggagcc gaaggtgccg actcctataa attcactagg ttcggcacgc   1740
tcaccattca cgacaccgaa aagtacgcct ctcagccaga actatgcact aactccactt   1800
gcatcggatc tcgaggacct ggctttagag ccttggagca caccaaatac tcctgttgcg   1860
ggcactgcag aaacccagaa cactggggaa gctggttcca aagcctgcca agatggtcaa   1920
ctgagcccaa cttggtcaga gatcgaggag gatttgagag cgtgcttcgg tgcggaaccg   1980
ttgaagaaag acttcagcga gccgctgaac ttggactaa                          2019
```

<210> SEQ ID NO 25
<211> LENGTH: 2019
<212> TYPE: DNA
<213> ORGANISM: Mouse parvovirus minute virus
<220> FEATURE:
<223> OTHER INFORMATION: strain M sequence

<400> SEQUENCE: 25

```
atggctggaa atgcttactc tgatgaagtt ttgggaacaa ccaactggtt aaaagagaaa     60
agtaaccagg aagtgttctc atttgttttt aaaaatgaag atgttcagct caatggaaaa    120
gatatcggat ggaatagtta caaaaaggag ctgcaagagg aagagctgaa atctttacaa    180
cgaggagcgg aaactacctg ggaccagagc gaggacatgg aatgggaatc ttcagtggat    240
gaactaacca aaaagcaagt attcatttt gactctttag ttaaaaaatg tttgtttgaa     300
gtgctgagta caagaacat agctcctagt gatgttactt ggtttgtaca gcatgaatgg    360
ggaaaagacc aaagctggca ctgtcatgta ctaattggag caaggactt tagccaagct    420 caaggaaaat ggtggagaag gcagttaaat gtttactgga gcagatggtt ggtaacagcc    480
```

```
tgtagtgtgc agctatcacc agctgaaaga attaagctga gagagatagc ggaagaccaa      540
gaatgggtca ctttgcttac ttataagcat aagcaaacca aaaaagacta taccaagtgt      600
gtttgctttg gaaatatagt tgcttactac tttttatcca agaagaaaat atgcaccagt      660
ccaccaaggg acggaggcta ttttcttagc agtgactctg gctggaaaac taactttta      720
aaagaaggcg aacgccatct agtgagcaaa ctatacactg atgacatgcg ccagaaacg       780
gttgaaacca caataaccac tgcgcaggaa actaagcgcg gcagaattca aactaaaaaa      840
gaggtctcta ttaaaaccac acttaaagag ctggtacata agagagtaac ctcaccagaa      900
gactggatga tgatgcagcc agacagttac attgaaatga tggctcaacc aggtggagaa      960
aacctgctta aaaatacgct agaaatctgt acgctaactc tagctagaac caaaacagca     1020
tttgacttga ttttagaaaa agctgaaacc agcaaactaa ccaacttttc actgccggac     1080
acaagaacct gcaagatctt tgcttttcat ggctggaact atgttaaagt ttgccatgct     1140
atttgctgtg ttctaaacag acaaggaggc aaaagaaata ctgttttatt tcatggacca     1200
gccagtacag gcaaatccat tattgcacaa gccatagcac aggcagttgg taatgttggt     1260
tgctataatg cagcaaatgt gaactttcca tttaatgact gcaccaacaa aaacctgatt     1320
tgggtggaag aagctggtaa cttggacag caagtaaacc agtttaaagc catttgctct      1380
ggtcaaacta tccgcattga tcaaaaagga aaaggcagca agcagattga accaacacca     1440
gtcatcatga ccacaaatga aaacattaca gtggtcagaa taggctgcga ggagagacca     1500
gagcacactc aaccaatcag agacagaatg ctcaacattc atctgacaca tacattgcct     1560
ggtgactttg gtttggttga caagaatgaa tggcccatga tttgtgcttg gttggtaaag     1620
aatggttacc aatctaccat ggcaagctac tgtgctaaat ggggcaaagt acctgattgg     1680
tcagaaaact gggcagagcc gaaggtaccg actcctataa attcactagg ttcagcacgc     1740
tcaccattca cgacaccgaa aagtacgcct ctcagccaga actatgcact aactccactt     1800
gcatcggatc tcgaggacct ggctttagag ccttggagca caccaaatac tcctgttgcg     1860
ggcactgcag aaacccagaa cactggggaa gctggttcca aagcctgcca agatggtcaa     1920
ctgagcccaa cttggtcaga gatcgaggag gatttgagag cgtgcttcgg tgcggaaccg     1980
ttgaagaaag acttcagcga gccgctgaac ttggactaa                            2019
```

<210> SEQ ID NO 26
<211> LENGTH: 1966
<212> TYPE: DNA
<213> ORGANISM: Parvovirus LuII

<400> SEQUENCE: 26

```
atggctggaa acgcgtactc tgatgaagtt ttgggaacaa ctaactggtt gaaggataag      60
agcaaccagg aagtattctc atttgttttt aaaaatgagg atgttcagct caatggaaaa     120
aatatcggat ggaacagtta cagaaaggag ctgcaagagg aggagctgaa atctttacaa     180
cgaggagctg aaactacctg gaccagagc gaggacatgg aatgggaatc ttcagtggat     240
gaactgacca aaaagcaagt attcattttt gactctttag ttaaaaagtg tctctttgaa     300
gtactgagca caaagaacat agctcctagt gatgttactt ggtttgtaca gcatgaatgg     360
ggaaaagacc aaggctggca ctgtcatgtg ctcattggag gcaagaactt tagccaggct     420
caaggaaaat ggtggaggag acaattaaat gtttactgga gtagatggtt ggtaacagcc     480
tgtagcgtgc agctatcacc agctgaaaga attaaactaa gagaaatagc agaagaccaa     540
gaatgggtta ctctgcttac ttataagcat aagcaaacca aaaaagacta tactaagtgt     600
```

```
gtttgctttg gaaatatggt tgcttactac tttttaacca aaaagaaaat atgtaccagt    660
ccaccaaggg acggaggcta ttttctcagt agtgactctg gctggaaaac taacttttg     720 aaagaaggcg aacgccatct agtgagcaaa ctatatactg atgacatgcg gccagaaacg    780
gttgagacca cagtaaccac agcgcaggaa actaagcgcg gcagaattca aactaagaag    840
gaagtctcta ttaagactac acttaaagag ctggtacata agagagtaac ctcaccagaa    900
gactggatga tgatgcagcc agacagttac attgaaatga tggctcaacc aggggagaa     960 aacctactta agaatacgct agagatctgt acgctgactc tagccagaac caaaacagcc   1020
tttgacttga ttttagaaaa agctgaaacc agcaaactaa ccaattttt actggctgat    1080 acaagaacct gtagaatctt tgcttttcat ggctggaact acatcaaagt ctgtcatgct   1140
atttgttgtg tcttgaacag acagggaggc aaaagaaata ctgttctgtt tcatggacca   1200
gccagtacag gcaaatcaat cattgcacag gccatagcac aggcagttgg taatgttggt   1260
tgttataacg cagccaatgt gaactttcca tttaatgact gtaccaacaa gaacttaatc   1320
tgggtggaag aagctggtaa cttggacag caagtaaacc agtttaaagc catttgttct    1380
ggtcagacca ttcgcattga ccaaaaagga aaggcagca acagattga accaacacca    1440 gtgatcatga ccacaaatga aaacatcaca gtggtcaaaa tagggtgtga agagagacca   1500
gaacacactc aaccaatcag agacagaatg ttaaacattc atctgacaca tacattgcct   1560
ggtgactttg gtttggttga taaaaacgaa tggcctatga tatgtgcttg gttggtaaag   1620
aacggttacc aatcgaccat ggcaagttac tgtgctaaat ggggcaaagt tcctgattgg   1680
acagaaaact gggcggagcc aaaagtaacg actgaaataa attcggtagg ttcaaccaac   1740
tcaccatctc cgaaaagtac gcctctcagc cagaactacg cactaactcc gtcggatctc   1800
gaggacctgg ctctggagcc ttggagcaca ccaagtactc ctgttgtggg cactgtcaaa   1860
accccgaaca ctggggaaac tggttcaaca gcctgtcaag aagctcaacg gagcccaact   1920
tggtccgaga tcgaggagga tttgagagcg tgcttcagtt cggaac                  1966

<210> SEQ ID NO 27
<211> LENGTH: 2019
<212> TYPE: DNA
<213> ORGANISM: Rat parvovirus UT

<400> SEQUENCE: 27
atggctggaa acgcttactc cgatgaggtt ttgggagcaa ccaactggct aaaggacaaa     60
agtagccaag aggtgttctc atttgttttt aaaaatgaga acgtccagct aaatgggaag    120
gacatcggtt ggaatagtta cagaaggag ctacaagatg acgagctgaa gtctctacaa     180
cgaggagcgg aaaccacttg gaccaaagc gaggacatgg aatgggagag cgcagtggat    240
gacatgacca aaaagcaagt attcattttt gattctttgg ttaagaaatg tttgtttgaa    300
gtgctcagca caaagaacat aactcctagt gatgttactt ggttcgtgca gcatgaatgg    360
ggaaaggacc aaggctggca ctgtcatgtg ctaattggag gcaaagactt tagtcaagct    420
caaggaaaat ggtggagaag gcagctaaat gtgtactgga gtagatggtt ggtgactgcc    480
tgtaatgttc aactaacacc agctgaaaga ataaaactga gagaaatagc agaggacagt    540
gaatgggtca ctttgcttac ctataagcat aagcacacca agaaggacta taccaagtgt    600 gttcttttg gaaacatgat tgcttattac tttttaagca aaaagaaaat atgtaccagt     660
ccaccaaggg acggaggcta ttttcttagc agtgactctg gctggaaaac taacttttg    720
```

```
aaagagggcg agcgccatct agtgagcaag ctgtatactg atgagatgaa accagaaacg    780
gttgagacca cagtgaccac agcacaggaa gctaagcgcg gcagaattca aactagaaag    840
gaggtctcta ttaaaaccac acttaaagag ttggtacata aaagagtaac ctcaccagaa    900
gactggatga tgatgcagcc agacagttac attgaaatga tggctcaacc aggtggagaa    960
aacttgctta aaatacact agagatctgt acactgactc tagcaagaac caaaacagca   1020
tttgacttga ttctggaaaa agctgaaacc agcaaactag ccaactttc catggctaac   1080 accagaacct gtagaatctt tgctgaacat ggctggaact atattaaagt ctgtcatgcc   1140
atctgttgtg tgctaaatag acaaggaggc aaaaggaaca ctgtgctctt tcatggacca   1200
gccagcacag gcaaatctat tattgcacaa gccatagcac aagcagttgg taatgttggt   1260
tgttataatg ctgccaatgt gaactttcca tttaatgact gcaccaacaa aaacttgatt   1320
tgggtggaag aagctggtaa ctttggccag caagtaaacc aattcaaagc tatttgttct   1380
ggccaaacca tacgcattga tcaaaaagga aaaggcagca acagattga accaacacca   1440 gttatcatga ccaccaacga gaacattacc gtggtcagaa taggctgtga ggaaagacca   1500
gaacacactc aaccaatcag agacagaatg ctcaacattc acctgacacg tacactgcct   1560
ggtgactttg gtctggtgga taagcacgaa tggcctctga tctgtgcttg gttggtgaag   1620
aatggttacc aatctaccat ggcttgttac tgtgctaaat ggggcaaagt tcctgattgg   1680
tcagaagact gggcggagcc gaagctagag actcctataa attcactagg ttcaatgcgc   1740
tcaccatctc tgactccgag aagtacgcct ctcagccaga actacgctct tactccactt   1800
gcatcggacc ttgcggacct agctctagag ccttggagca caccaaatac tcctgttgtg   1860
ggcactgcag caagccagaa cactggggag gctggttca cagcctgcca aggtgctcaa   1920
cggagcccaa cctggtccga gatcgaggcg gatctgagag cgtgcttcag ccaggaacag   1980
ctggagaaag acttcagcga ttcactgacc ttggactaa                          2019

<210> SEQ ID NO 28
<211> LENGTH: 2019
<212> TYPE: DNA
<213> ORGANISM: Kilham rat virus

<400> SEQUENCE: 28
atggctggaa acgcttactc cgatgaggtt ttgggagcaa ccaactggct aaaggacaaa     60
agtagccagg aggtgttctc atttgttttt aaaaatgaga acgtccaact aaatggaag    120 gacatcggtt ggaatagtta cagaaaggag ctacaagatg acgagctgaa gtctctacaa    180
cgaggggcgg agaccacttg ggaccaaagc gaggacatgg aatgggagag cgcagtggat    240
gacatgacca aaaagcaagt attcattttt gattctttgg ttaagaagtg tttgtttgaa    300
gtgctcagca caaagaacat agctcctagt gatgttactt ggttcgtgca gcatgaatgg    360
ggaaaggacc aaggctggca ctgtcatgtg ctgattggag caaggactt tagtcaagct    420 caaggaaaat ggtggagaag gcagctaaat gtgtactgga gtagatggtt ggtgactgcc    480
tgtaatgttc aactaacacc agctgaaaga attaaactga gagaaatagc agaagacagt    540
gaatgggtca ctttgcttac ctataagcat aagcacacca agaaggacta taccaagtgt    600 gttcttttg aaacatgat tgcttattac tttctaagca aaagaaaat atgtaccagt    660 ccaccaaggg acgaggcta ttttcttage agtgactctg gctggaaaac taacttttg    720 aaagagggcg agcgccatct agtgagcaaa ctatatactg atgagatgaa accagaaacg    780
gtcgagacca cagtgaccac tgcgcaggaa gctaagcgcg gcagaattca aactagaaag    840
```

```
gaggtctcga ttaaaaccac actcaaagag ttggtgcata aaagagtaac ctcaccagaa    900
gactggatga tgatgcagcc agacagttac attgaaatga tggctcaacc aggtggagaa    960
aacttgctta aaatacact agagatctgt acactgactc tagcaagaac caaaacagcc    1020
tttgacttga ttctggaaaa agctgaaacc agcaaactag ccaacttttc catggctagc    1080
accagaacct gtagaatctt tgctgagcat ggctggaact atattaaagt ctgccatgcc    1140
atctgttgtg tgctaaatag acaaggaggc aaaaggaaca ctgtgctctt tcacggacca    1200
gccagcacag gcaaatctat cattgcacaa gccatagcac aaggagttgg taatgttggt    1260
tgttataatg ctgccaatgt gaactttcca tttaatgact gtaccaacaa aaacttgatt    1320
tgggtggaag aagctggtaa ctttggccag caagtaaacc aattcaaagc tatttgttct    1380
ggccaaacca tacgcattga tcaaaaagga aaaggcagca acagattga accaacacca    1440 gttatcatga ccaccaacga gaacattacc gtggtcagaa taggctgtga ggaaagacca    1500
gaacacactc aaccaatcag agacagaatg ctcaacattc acctgacacg tacactgcct    1560
ggtgactttg gtctggtgga taagcacgaa tggcctctga tctgtgcttg gttggtgaag    1620
aatggttacc aatctaccat ggcttgttac tgtgctaaat gggcaaagt tcctgattgg    1680 tcagaggact gggcggagcc gaagctagag actcctataa tttcgctagg ttcaatgcgc    1740
tcaccatctc tgactccgag aagtacgcct ctcagccaga actacgctct tactccactt    1800
gcatcggacc ttgcggacct agctctagag ccttggagca caccaaatac tcctgttgcg    1860
ggcactgcag caagccagaa cactggggag gctggtttca cagcctgcca aggtgctcaa    1920
cggagcccaa cctggtccga gatcgaggcg gatctgagag cgtgcttcag ccaggaacag    1980
ctggagaaag acttcagcga ttcactgaca ttggactaa              2019

<210> SEQ ID NO 29
<211> LENGTH: 2024
<212> TYPE: DNA
<213> ORGANISM: Rat minute virus 1c

<400> SEQUENCE: 29
atggctggaa acgcttactc cgatgaagtt ttgggagcaa ccaactggct aaaggacaaa     60
agtagccagg aagtgttctc atttgttttt aaaaatgaga acgtccaact aaatgggaag    120
gacatcggtt ggaatagtta cagaaaagag ctacaagatg acgagctgaa gtctctacaa    180
cgaggggcgg agaccacttg ggaccaaagc gaggacatgg aatgggagag cgcagtggat    240
gacatgacca aaaagcaagt attcattttt gattctttgg ttaagaagtg tctgtttgaa    300
gtgctcagca caaagaacat agctcctagt gatgttactt ggttcgtgca gcatgaatgg    360
ggaaaggacc aaggctggca ctgtcatgtg ctgattggag caaggactt tagtcaagct    420 caaggaaaat ggtggagaag gcagctaaat gtgtactgga gtagatggtt agtgactgcc    480
tgtaatgttc aactaacacc agctgaaaga attaaactga gagaaatagc agaggacagt    540
gaatgggtca ctttgcttac ctataagcat aagcacacca gaaggacta taccaagtgt    600 gttctttttg gaaacatgat tgcttattac tttctaagca aaaagaaaat atgtaccagt    660
ccaccaaggg acggaggcta ttttcttagc agtgactctg ctggaaaac taacttttg    720 aaagagggcg agcgccatct agtgagcaaa ctgtatactg atgagatgaa accagaaacg    780
gtcgagacca cagtgaccac tgcgcaggaa gctaagcgcg gcagaattca aactagaaag    840
gaggtctcga ttaaaaccac actcaaagag ttggtacata aaagagtaac ctcaccagaa    900
```

```
gactggatga tgatgcagcc agacagttac attgaaatga tggctcaacc aggtggagaa    960
aacttgctta aaaatacact agagatttgt acactgactc tagcaagaac caaaacagcc   1020
tttgacttga ttctggaaaa agctgaaacc agcaaactag ccaactttc catggctagc    1080 accagaacct gtagaatctt tgctgagcat ggctggaact atattaaagt ctgccatgcc   1140
atctgttgtg tactaaatag acaaggaggc aaaaggaaca ctgtgctctt tcacggacca   1200
gccagcacag gcaaatctat cattgcacaa gccatagcac aaggagttgg taatgttggt   1260
tgttacaatg ctgccaatgt gaactttcca tttaatgact gtaccaacaa aaacttgatt   1320
tgggtggaag aagctggtaa ctttggccag caagtaaacc aattcaaagc tatttgttct   1380
ggccaaacca tacgcattga tcaaaaagga aaggcagca aacagattga accaacacca    1440
gttatcatga ccaccaacga gaacattaca gtggtcagaa taggctgtga ggaaagacca   1500
gaacacactc aaccaatcag agacagaatg ctcaacattc acctgacacg tacactgcct   1560
ggtgactttg gtctggtgga taagcacgaa tggcctctaa tctgtgcttg gttggtgaag   1620
aatggttacc aatctaccat ggcttgttac tgtgctaaat ggggcaaagt tcctgattgg   1680
tcagaggact gggcggagcc gaagctagag actcctataa attcgctagg ttcaatgcgc   1740
tcaccatctc tgactccgag aagtacgcct ctcagccaga actacgctct tactccactt   1800
gcatcggacc ttgcggacct agccctagag ccttggagca caccaaatac tcctgttgcg   1860
ggcactgcag caagccagaa cactggggag ctggtttca cagcctgtca aggtgctcaa    1920
cggagcccaa cctggtccga gatcgaggcg gatctgagag cgtgcttcag ccaggaacag   1980
ctggagaaag acttcagcga ttcactgacc ttggactaag gtac                    2024

<210> SEQ ID NO 30
<211> LENGTH: 2019
<212> TYPE: DNA
<213> ORGANISM: Rat minute virus 1b

<400> SEQUENCE: 30
atggctggaa acgcttactc cgatgaggtt ttgggagcaa ccaactggct aaaggacaaa     60
agtagccagg aggtgttctc atttgttttt aaaaatgaga acgtccaact aaatgggaag   120
gacatcggtt ggaatagtta cagaaaggag ctacaagatg acgagctgaa gtctctgcaa    180
cgaggggcgg agaccacttg ggaccaaaagc gaggacatgg aatggagag cgcagtggat    240 gacatgacca aaaagcaagt attcattttt gattctttgg ttaagaagtg tctgtttgaa   300
gtgctcagca caaagaacat agctcctagt gatgttactt ggtttgtgca gcatgaatgg   360
ggaaaagacc aaggctggca ctgtcatgtg ctgattggag gcaaggactt tagtcaagct   420
caaggaaaat ggtggagaag gcagctaaat gtgtactgga gtagatggtt ggtgactgcc    480
tgtaatgttc aactaacacc agctgaaaga attaaactga gagaaatagc agaggacagt   540
gaatgggtga ctttgcttac ctataagcat aagcacacca agaaggacta taccaagtgt   600
gttctttttg gaaacatgat tgcttattac tttctaagca aaagaaaat atgtaccagt    660 ccaccaaggg acggaggcta ttttcttagc agtgactctg gctggaaaac taactttttg   720
aaagagggcg agcgccatct agtgagcaaa ctgtatactg atgagatgaa accagaaacg   780
gtcgagacca cagtgaccac tgcgcaggaa gctaagcgcg cagaattca actagaaag    840 gaggtctcga ttaaaaccac actcaaagag ttggtgcata aaagagtaac ctcaccagaa   900
gactggatga tgatgcagcc agacagttac attgaaatga tggctcaacc aggtggagaa   960
aacttgctta aaatacact agagatctgt acactgactc tagcaagaac caaaacagcc    1020
```

```
tttgacttga ttctggaaaa agctgaaacc agcaaactag ccaactttt catggctaac    1080 accagaacct gtagaatctt tgctgagcat ggctggaact atattaaagt ctgtcatgcc    1140
atctgttgtg tgctaaatag acaaggaggc aaaaggaaca ctgtgctctt cacggacca     1200 gccagcacag gcaaatctat cattgcacaa gccatagcac aaggagttgg taatgttggt    1260
tgttataatg ctgccaatgt gaactttcca tttaatgact gtaccaacaa aaacttgatt    1320
tgggtggaag aagctggtaa ctttggccag caagtaaacc aattcaaagc tatttgttct    1380
ggccaaacca tacgcattga tcaaaaagga aaaggcagca acagattga accaacacca     1440 gttatcatga ccaccaacga gaacattacc gtggtcaaaa taggctgtga ggaaagacca    1500
gaacacactc aaccaatcag agacagaatg ctcaacattc acctgacacg tacactgcct    1560
ggtgactttg gtctggtgga taagcacgaa tggcctctga tctgtgcttg gttggtaaag    1620
aatggttacc aatctaccat ggcttgttac tgtgctaaat ggggcaaagt tcctgattgg    1680
tcagaggact gggcggagcc gaagctagag actcctataa attcgctagg ttcaatgcgc    1740
tcaccatctc tgactccgag aagtacgcct ctcagccaga actacgctct tactccactt    1800
gcatcggatc tcgcggacct ggcactggaa ccttggagca caccaaatac tcctgttgtg    1860
gacactgtac aaaccccgaa cactggggag ctggtttca cagcctgcca aggtgctcaa     1920
cggagcccaa cctggtccga gatcgaggcg gatctgagag cgtgcttcag ccaggaacag    1980
ctggagaaag acttcagcga ttcactgacc ttggactaa                           2019

<210> SEQ ID NO 31
<211> LENGTH: 1997
<212> TYPE: DNA
<213> ORGANISM: Rat minute virus 1a

<400> SEQUENCE: 31
atgaggtttt gggagcaacc aactggctaa aggacaaaag tagccaggag gtgttctcat      60
ttgtttttaa aaatgagaac gtccaactaa atgggaagga catcggttgg aatagttaca    120
gaaaggagct acaagatgac gagctgaagt ctttgcaacg aggggcggag accacttggg    180
accaaagcga ggacatggaa tgggagagcg cagtggatga catgaccaaa aagcaagtat    240 tcattttga ttctttggtt aaaaagtgtc tgtttgaagt gctcagcaca agaacatag       300 ctcctagtga tgttacttgg ttcgtgcagc atgaatgggg aaaggaccaa ggctggcact    360
gtcatgtgct gattggaggc aaggactta gtcaacctca aggaaagtgg tggagaaggc     420
agctaaatgt gtactggagt agatggttgg tgactgcctg taatgttcaa ctaacaccag    480
ctgaaagaat taaactgaga gaaatagcag aggacagtga atgggtcact ttgcttacct    540
ataagcataa acacaccaag aaggactata ccaagtgtgt ttttttgga aacatgattg      600 cttattactt tctaagcaaa agaaaatat gtaccagtcc accaagggac ggaggctatt     660
ttcttagcag tgactctggc tggaaaacta acttttgaa agagggcgag cgccatctag     720
tgagcaaact gtatactgat gagatgaaac agaaacggt cgagaccaca gtgaccactg     780
cgcaggaagc taagcgcggc agaattcaaa ctagaaagga ggtctcgatt aaaccacac     840 tcaaagagtt ggtgcataaa agagtaacct caccagaaga ctggatgatg atgcagccag    900
acagttacat tgaaatgatg gctcaaccag gtggagaaaa cttgcttaaa aatacactag    960
agatctgtac actgactcta gcaagaacca aaacagcctt tgacttgatt ctagaaaaag   1020
ctgaaaccag caaactagcc aacttttcca tggctaacac cagaacctgt agaatctttg   1080
```

| | |
|---|---|
| ctgagcatgg ctggaactat attaaagtct gccatgccat ctgttgtgtg ctgaatagac | 1140 |
| aaggaggcaa aaggaacact gtgctctttc acggaccagc cagcacaggc aaatctatca | 1200 |
| ttgcacaagc catagcacaa ggagttggta atgttggttg ttacaatgct gccaatgtga | 1260 |
| actttccatt taatgactgt accaacaaaa acttgatttg ggtggaagaa gctggtaact | 1320 |
| ttggccagca agtaaaccaa ttcaaagcta tttgttctgg ccaaaccata cgcattgatc | 1380 |
| aaaaaggaaa aggcagcaaa cagattgaac caacaccagt tatcatgacc accaacgaga | 1440 |
| acattaccgt ggtcagaata ggctgtgagg aaaggccaga acacactcaa ccaatcagag | 1500 |
| acagaatgct caacattcac ctgacacgta cactgcctgg tgactttggt ctggtggata | 1560 |
| agcacgaatg gcctctgatc tgtgcttggt tggtgaagaa tggttaccaa tctaccatgg | 1620 |
| cttgttactg tgctaaatgg ggcaaagttc ctgattggtc agaggactgg gcggagccga | 1680 |
| agctagagac tcctataaat tcgctaggtt caatgcgctc accatctctg actccgagaa | 1740 |
| gtacgcctct cagccagaac tacgctctta ctccacttgc atcggacctt gcggacctag | 1800 |
| ctctagagcc ttggagcaca ccaaatactc ctgttgcggg cactgcagca agccagaaca | 1860 |
| ctggggaggc tggtttcaca gcctcccaag gtgctcaacg gagcccaacc tggtccgaga | 1920 |
| tcgaggcgga tctgagagcg tgcttcagcc aggaacagct ggagaaagac ttcagcgatt | 1980 |
| cactgacctt ggactaa | 1997 |

<210> SEQ ID NO 32
<211> LENGTH: 2019
<212> TYPE: DNA
<213> ORGANISM: H-1 parvovirus

<400> SEQUENCE: 32

| | |
|---|---|
| atggctggaa acgcttactc cgatgaggtt ttgggagtaa ccaactggct gaaggacaaa | 60 |
| agtagccagg aggtgttctc atttgttttt aaaaatgaaa acgtccaact aaatggaaag | 120 |
| gacatcggtt ggaatagtta cagaaaggag ctacaagatg acgagctgaa gtctctacaa | 180 |
| cgaggggcgg agaccacttg ggaccaaagc gaggacatgg aatgggagag cgcagtggat | 240 |
| gacatgacca aaaagcaagt atttattttt gattctttgg ttaagaagtg tttgtttgaa | 300 |
| gtgctcagca caagaacat agctcctagt aatgttactt ggttcgtgca gcatgaatgg | 360 |
| ggaaaggacc aaggctggca ctgtcatgtg ctgattggag caaggacttt agtcaacct | 420 |
| caaggaaaat ggtggagaag gcagctaaat gtgtactgga gtagatggtt ggtgactgcc | 480 |
| tgtaatgttc aactaacacc agctgaaaga attaaactga gagaaatagc agaggacagt | 540 |
| gaatgggtca ctttgcttac ctataagcat aagcacacca agaaggacta taccaagtgt | 600 |
| gttcttttg aaacatgat tgcttattac ttttttaagca aaaagaaaat atgtaccagt | 660 |
| ccaccaaggg acggaggcta ttttcttagc agtgactctg gctggaaaac taacttttg | 720 |
| aaagagggcg agcgccatct agtgagcaaa ctgtatactg atgagatgaa accagaaacg | 780 |
| gtcgagacca cagtgaccac tgcacaggaa gctaagcgcg gcagaattca aactagaaag | 840 |
| gaggtctcga ttaaaaccac actcaaagag ttggtacata aagagtaac ctcaccagaa | 900 |
| gactggatga tgatgcagcc agacagttac attgaaatga tggctcaacc aggtggagaa | 960 |
| aacttgctta aaatacact agagatctgt acactgactc tagcaagaac caaaacagcc | 1020 |
| tttgacttga ttctggaaaa agctgaaacc agcaaactag ccaactttc catggctagc | 1080 |
| accagaacct gtgaatctt tgctgagcat ggctggaact atattaaagt ctgccatgcc | 1140 |
| atctgttgtg tgctgaatag acaaggaggc aaaaggaaca ctgtgctctt tcacggacca | 1200 |

```
gccagcacag gcaaatctat tattgcacaa gccatagcac aagcagttgg taatgttggt    1260
tgttacaatg ctgccaatgt gaactttcca tttaatgact gtaccaacaa aaacttgatt    1320
tgggtggaag aagctggtaa cttttggcca caagtaaacc aattcaaagc tatttgttct    1380
ggccaaacca tacgcattga tcaaaaagga aaaggcagca acagattga accaacacca     1440 gttattatga ccaccaacga gaacattacc gtggttagaa taggctgtga ggaaagacca    1500
gaacacactc aaccaatcag agacagaatg ctcaacattc acctgacacg tacactacct    1560
ggtgactttg gtttggtgga taagcacgaa tggcctctga tctgtgcttg gttggtgaag    1620
aatggttacc aatctaccat ggcttgttac tgtgctaaat ggggcaaagt tcctgattgg    1680
tcagaggact gggcggagcc gaagctagac actcctataa attcgctagg ttcaatgcgc    1740
tcaccatctc tgactccgag aagtacgcct ctcagccaaa actacgctct tactccactt    1800
gcatcggacc ttgcggacct agctctagag ccttggagca caccaaatac tcctgttgcg    1860
ggcactgcag caagccaaaa cactggggag gctggttcca cagcctgcca aggtgctcaa    1920
cggagcccaa cctggtccga gatcgaggcg gatttgagag cttgcttcag tcaagaacag    1980
ttggagagcg acttcaacga ggagctgacc ttggactaa                          2019

<210> SEQ ID NO 33
<211> LENGTH: 2019
<212> TYPE: DNA
<213> ORGANISM: Rat minute virus isolate NTU1

<400> SEQUENCE: 33
atggctggaa acgcttactc cgatgaagtt ttgggagcaa ccaactggct aaaggacaaa      60
agtagccagg aggtgttctc atttgttttt aaaaatgaga acgtccaact aaatgggaag     120
gacatcggtt ggaatagtta cagaaaggag ctacaagatg acgagctgaa gtctctacaa     180
cgaggggcgg agaccacttg ggaccaaagc gaggacatgg aatgggagag cgcagtggat     240
gacatgacca aaaagcaagt attcattttt gattctttgg ttaagaagtg tttgtttgaa     300
gtgctcagca caaagaacat agctcctagt gatgttactt ggttcgtgca gcatgaatgg     360
ggaaaggacc aaggctggca ctgtcatgtg ttgattggag caaggacttt tagtcaagct     420
caaggaaaat ggtggagaag gcagctaaat gtgtactgga gtagatggtt ggtgactgcc     480
tgtaatgttc aactaacacc agctgaaaga attaaactga gagaaatagc agaggacagt     540
gaatgggtca ctttgcttac ctataagcat aagcacacca agaaggacta taccaagtgt     600 gttcttttg gaaacatgat tgcttattac tttctaagca aaaagaaaat atgtaccagt     660
ccaccaaggg acggaggcta ttttcttagc agtgactctg gctggaaaac taacttttg      720 aaagagggcg agcgccatct agtgagcaaa ctgtatactg atgagatgaa accagaaacg     780
gtcgagacca cagtgaccac tgcacaggaa gctaagcgcg gcagaattca aactagaaag     840
gaggtctcga ttaaaaccac actcaaagag ttggtacata aaagagtaac ctcaccagaa     900
gactggatga tgatgcagcc agacagttat attgaaatga tggctcaacc aggtggagaa     960
aacttgctta aaaatacact agagatatgt acactgactc tagcaagaac caaaacagcc    1020
tttgacttga ttctggaaaa agctgaaacc agcaaactag ccaacttttc tatggctaac    1080
accagaacct gtagaatctt tgctgagcat ggctggaact atattaaagt ctgccatgcc    1140
atctgttgtg tgctaaatag acaaggaggc aaaaggaaca ctgtgctctt tcacggacca    1200
gccagcacag gcaaatctat cattgcacaa gccatagcac aagcagttgg taatgttggt    1260
```

| | |
|---|---|
| tgttacaatg ctgccaatgt gaactttcca tttaatgact gtaccaacaa aaacttgatt | 1320 |
| tgggtggaag aagctggtaa ctttggccag caagtaaacc aattcaaagc tatttgttct | 1380 |
| ggccaaacca tacgcattga tcaaaaagga aaaggcagca aacagattga accaacacca | 1440 |
| gttatcatga ccaccaacga gaacattacc gtggtcagaa taggctgtga ggaaagacca | 1500 |
| gaacacactc aaccaatcag agacagaatg ctcaacattc acctgacacg tacactgcct | 1560 |
| ggtgactttg gtctggtgga taagcacgaa tggcctctga tctgtgcttg gttggtgaag | 1620 |
| aatggttacc aatctacaat ggcttgttac tgtgctaaat ggggcaaagt tcctgattgg | 1680 |
| tcagaagact gggcggagcc gaagctagag actcctataa attcgctagg ttcaatgcgc | 1740 |
| tcaccatctc tgactccgag aagtacgcct ctcagccaga actacgctct tactccactt | 1800 |
| gcatcggacc ttgcggacct agctctggag ccttggagca caccaaatac tcctgttgcg | 1860 |
| ggcactgcag caagccagaa cactggggag ctggtttcg cagcctgcca aggtgctcaa | 1920 |
| cggagcccaa cctggtccga gatagaagca gacttgagag cttgcttcag tcaagaacag | 1980 |
| ttggagagcg acttcaacga ggaactgacc ttggactaa | 2019 |

<210> SEQ ID NO 34
<211> LENGTH: 2019
<212> TYPE: DNA
<213> ORGANISM: Parvovirus h-1

<400> SEQUENCE: 34

| | |
|---|---|
| atggctggaa acgcttactc cgatgaggtt ttgggagtaa caaactggct gaaggacaaa | 60 |
| agtagccagg aggtgttctc atttgttttt aaaaatgaaa acgtccaact aaatggaaag | 120 |
| gacatcggtt ggaatagtta cagaaaggag ctacaagatg acgagctgaa gtctctacaa | 180 |
| cgaggggcgg agaccacttg ggaccaaagc gaggacatgg aatgggagag cgcagtggat | 240 |
| gacatgacca aaaagcaagt atttattttt gattctttgg ttaagaagtg tttgtttgaa | 300 |
| gtgctcagca caagaacat agctcctagt aatgttactt ggttcgtgca gcatgaatgg | 360 |
| ggaaaggacc caggctggca ctgtcatgtg ctgattggag gcaaggactt tagtcaacct | 420 |
| caaggaaaat ggtggagaag gcagctaaat gtgtactgga gtagatggtt ggtgactgcc | 480 |
| tgtaatgttc aactaacacc agctgaaaga attaaactga gagaaatagc agaggacagt | 540 |
| gaatgggtca ctttgcttac ctataagcat aagcacacca agaaggacta taccaagtgt | 600 |
| gttcttttg gaaacatgat tgcttattac ttttaagca aaagaaaat atgtaccagt | 660 |
| ccaccaaggg acggaggcta ttttcttagc agtgactctg gctggaaaac taacttttg | 720 |
| aaagagggcg agcgccatct agtgagcaaa ctgtatactg atgagatgaa accagaaacg | 780 |
| gtcgagacca cagtgaccac tgcacaggaa gctaagcgcg gcagaattca actagagag | 840 |
| gaggtctcga ttaaaaccac actcaaagag ttggtacata aagagtaac ctcaccagaa | 900 |
| gactggatga tgatgcagcc agacagttac attgaaatga tggctcaacc aggtggagaa | 960 |
| aacttgctta aaaatacact agagatctgt acactgactc tagcaagaac caaaacagcc | 1020 |
| tttgacttga ttctggaaaa agctgaaacc agcaaactag ccaactttc catggctagc | 1080 |
| accagaacct gtagaatctt tgctgagcat ggctggaact atattaaagt ctgccatgcc | 1140 |
| atctgttgtg tgctgaatag acaaggaggc aaaaggaaca ctgtgctctt tcacggacca | 1200 |
| gccagcacag gcaaatctat tattgcacaa gccatagcac aagcagttgg taatgttggt | 1260 |
| tgttacaatg ctgccaatgt gaactttcca tttaatgact gtaccaacaa aaacttgatt | 1320 |
| tgggtggaag aagctggtaa ctttggccag caagtaaacc aattcaaagc tatttgttct | 1380 |

```
ggccaaacca tacgcattga tcaaaaagga aaaggcagca aacagattga accaacacca      1440
gttattatga ccaccaacga gaacattacc gtggttagaa taggctgtga ggaaagacca      1500
gaacacactc aaccaatcag agacagaatg ctcaacattc acctgacacg tacactacct      1560
ggtgactttg gtttggtgga taagcacgaa tggcctctga tctgtgcttg gttggtgaag      1620
aatggttacc aatctaccat ggcttgttac tgtgctaaat ggggcaaagt tcctgattgg      1680
tcagaggact gggcggagcc gaagctagac actcctataa attcgctagg ttcaatgcgc      1740
tcaccatctc tgactccgag aagtacgcct ctcagccaaa actacgctct tactccactt      1800
gcatcggacc ttgcggacct agctctagag ccttggagca caccaaatac tcctgttgcg      1860
ggcactgcag caagccaaaa cactggggag gctggttcca cagcctgcca aggtgctcaa      1920
cggagcccaa cctggtccga gatcgaggcg gatttgagag cttgcttcag tcaagaacag      1980
ttggagagcg acttcaacga ggagctgacc ttggactaa                             2019

<210> SEQ ID NO 35
<211> LENGTH: 1997
<212> TYPE: DNA
<213> ORGANISM: Rat minute virus isolate NTU2

<400> SEQUENCE: 35
atgaggtttt gggagcaacc aactggctaa aggacaaaag tagccaggag gtattctcat        60 ttgttttttaa aaatgagaac gtccaactaa atgggaagga catcggttgg aatagttaca      120
gaaaggagct acaagatgac gagctgaagt ctctacaacg aggggcggag accacttggg      180
accaaagcga ggacatggaa tgggagagcg cagtggatga catgaccaaa aagcaagtat      240 tcattttttga ttctttggtt aagaagtgtc tgtttgaagt gctcagcaca agaacatag      300 ctcctagtga tgttacttgg ttcgtgcagc atgaatgggg aaaggaccaa ggctggcact      360
gtcatgtgct gattggaggc aaggacttta gtcaagctca aggaaaatgg tggagaaggc      420
agctaaatgt gtactggagt agatggttgg tgactgcctg taatgttcaa ctaacaccag      480
ctgaaagaat taaactaaga gaaatagcag aggacagtga atgggtcact ttgcttacct      540
ataagcataa gcacaccaag aaggactata ccaagtgtgt tcttttttgga aacatgattg      600 cttattactt tctaagcaaa aagaaaatat gtaccagtcc accaagggac ggaggctatt      660
ttcttagcag tgactctggc tggaaaacta acttttttgaa agagggcgag cgccatctag      720
tgagcaaact gtatactgat gagatgaaac cagaaacggt cgagaccaca gtgaccactg      780
cacaggaagc taagcgcggc agaattcaaa ctagaaagga ggtctcgatt aaaaccacac      840
tcaaagagtt ggtacataaa gagtaacct caccagaaga ctggatgatg atgcagccag      900
acagttatat tgaaatgatg gctcaaccag gtggagaaaa cttgcttaaa aatacactag      960
agatatgtac actgactcta gcaagaacca aaacagcctt tgacttgatt ctggaaaaag     1020
ctgaaaccag caaactagcc aacttttcta tggctagcac cagaacctgt agaatctttg     1080
ctgagcatgg ctggaactat attaaagtct gccatgccat ctgttgtgtg ctaaatagac     1140
aaggaggcaa aaggaacact gtgctctttc acggaccagc cagcacaggc aaatctatca     1200
ttgcacaagc catagcacaa gcagttggta atgttggttg ttacaatgct gccaatgtga     1260
actttccatt taatgactgt accaacaaaa acttgatttg ggtggaagaa gctggtaact     1320
ttggccagca agtaaaccaa ttcaaagcta tttgttctgg ccaaaccata cgcattgatc     1380
aaaaaggaaa aggcagcaaa cagattgaac caacaccagt tatcatgacc accaacgaga     1440
```

| | | |
|---|---|---|
| acattaccgt ggtcagaata ggctgtgagg aaagaccaga acacactcaa ccaatcagag | 1500 | |
| acagaatgct caacattcac ctgacacgta cactgcctgg tgactttggt ctggtggata | 1560 | |
| agcacgaatg gcctctgatc tgtgcttggt tggtgaagaa tggttaccaa tctaccatgg | 1620 | |
| cttgttactg tgctaaatgg ggcaaagttc ctgattggtc agaagactgg gcggagccga | 1680 | |
| agctagagac tcctataaat tcgctaggtt caatgcgctc accatctctg actccgagaa | 1740 | |
| gtacgcctct cagccagaac tacgctctta ctccacttgt atcggacctt gcggacctag | 1800 | |
| ctctggagcc ttggagcaca ccaaatactc ctgttgcggg cactgcagca agccagaaca | 1860 | |
| ctggggaggc tggtttcgca gcctgtcaag gtgctcaacg gagcccaacc tggtccgaga | 1920 | |
| tagaagcaga cttgagagct tgcttcagtc aagaacagtt ggagagcgac ttcaacgagg | 1980 | |
| agctgacctt ggactaa | 1997 | |

<210> SEQ ID NO 36
<211> LENGTH: 2019
<212> TYPE: DNA
<213> ORGANISM: Rat minute virus 2a

<400> SEQUENCE: 36

| | | |
|---|---|---|
| atggctggaa acgcttactc cgatgaggtt ttgggagcaa ccaactggct aaaggacaaa | 60 | |
| agtagccagg aggtgttctc atttgttttt aaaaatgaga acgtccaact aaatgggaag | 120 | |
| gacatcggtt ggaatagtta cagaaaggag ctacaagatg acgagctgaa gtctctacaa | 180 | |
| cgaggggcgg agaccacttg ggaccaaagc gaggacatgg aatgggagag cgcagtggat | 240 | |
| gacatgacca aaaagcaagt attcattttt gattctttgg ttaagaagtg tctgtttgaa | 300 | |
| gtgctcagca caaagaacat agctcctagt gatgttactt ggttcgtgca gcatgaatgg | 360 | |
| ggaaaggacc aaggctggca ctgtcatgtg ctgattggag caaggactt tagtcaagct | 420 | |
| caaggaaaat ggtggagaag gcagctaaat gtgtactgga gtagatggtt ggtgactgcc | 480 | |
| tgtaatgttc aactaacacc agctgaaaga attaaactga gagaaatagc agaggacagt | 540 | |
| gaatgggtca cttgcttac ctataagcat aagcacacca agaaggacta taccaagtgt | 600 | |
| gttcttttg aaacatgat tgcttattac tttctaagca aaaagaaaat atgtaccagt | 660 | |
| ccaccaaggg acggaggcta ttttcttagc agtgactctg gctgaaaaac taacttcttg | 720 | |
| aaagagggcg agcgccatct agtgagcaaa ctgtatactg atgagatgaa accagaaacg | 780 | |
| gtcgagacca cagtgaccac tgcgcaggaa gctaagcgcg gcagaattca aactagaaag | 840 | |
| gaggtctcga ttaaaaccac actcaaagag ttggtgcata aaagagtaac ctcaccagaa | 900 | |
| gactggatga tgatgcagcc agacagttac attgaaatga tggctcaacc aggtggagaa | 960 | |
| aacttgctta aaaatacact agagatatgt acactgactc tagcaagaac caaaacagcc | 1020 | |
| tttgacttga ttctggaaaa agctgaaacc agcaaactag ccaactttc catggctagc | 1080 | |
| accagaacct gtagaatctt tgttgagcat ggctggaact atattaaagt ctgccatgcc | 1140 | |
| atctgttgtg tactaaatag acaaggaggc aaaaggaaca ctgtgctctt tcacggacca | 1200 | |
| gccagcacag gcaaatctat cattgcacaa gccatagcac aagcagttgg taatgttggt | 1260 | |
| tgttacaatg ctgccaatgt gaactttcca tttaatgact gtaccaacaa aaacttgatt | 1320 | |
| tgggtggaag aagctggtaa cttttggccag caagtaaacc aattcaaagc tatttgttct | 1380 | |
| ggccaaacca tacgcattga tcaaaaagga aaaggcagca acagattga accaacacca | 1440 | |
| gttatcatga ccaccaacga aaacattacc gtggtcagaa taggctgtga ggaaagacca | 1500 | |
| gaacacactc aaccaatcag agacagaatg ctcaacattc acctgacacg tacactgcct | 1560 | |

-continued

```
ggtgactttg gtctggtgga taagcacgaa tggcctctga tctgtgcttg gttggtgaag    1620
aatggttacc aatctacaat ggcttgttac tgtgctaaat ggggcaaagt tcctgattgg    1680
tcagaagact gggcggagcc gaagctagag actcctataa attcgctagg ttcaatgcgc    1740
tcaccatctc tgactccgag aagtacgcct ctcagccaga actacgctct tactccactt    1800
gcatcggacc ttgcggacct agctctggag ccttggagca caccaaatac tcctgttgcg    1860
ggcactgtag caagccagaa cactggggag gctggtttcg cagcctgcca aggtgctcaa    1920
cggagcccaa cctggtccga gatagaagca gacttgagag cttgcttcag tcaagaacag    1980
ttggagagcg acttcaacga ggaactgacc ttggactaa                           2019

<210> SEQ ID NO 37
<211> LENGTH: 192
<212> TYPE: DNA
<213> ORGANISM: Artificial
<220> FEATURE:
<223> OTHER INFORMATION: consensus sequence

<400> SEQUENCE: 37
ctarrrarga rgtytcdatt aaaacyacac tyaaagaryt rgtrcataar agagtaacct      60
caccagarga ctggatgatg atgcagccag acagttayat tgaaatgatg gctcarccag     120
gkggagaaaa cytrctdaar aatacrctag aratytgtac rctractcta gchagaacma    180
aaacagcmtt tg                                                        192
```